(12) United States Patent
Fujiyama et al.

(10) Patent No.: US 7,763,727 B2
(45) Date of Patent: Jul. 27, 2010

(54) COMPOUND AND ORGANIC ELECTRONIC DEVICE USING THE SAME

(75) Inventors: Takahiro Fujiyama, Kisarazu (JP); Kenichi Sugimoto, Yokohama (JP); Michiru Sekiguchi, Kawasaki (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 825 days.

(21) Appl. No.: 10/594,156

(22) PCT Filed: Mar. 29, 2005

(86) PCT No.: PCT/JP2005/005979
§ 371 (c)(1), (2), (4) Date: Sep. 26, 2006

(87) PCT Pub. No.: WO2005/092901
PCT Pub. Date: Oct. 6, 2005

(65) Prior Publication Data
US 2007/0219375 A1   Sep. 20, 2007

(30) Foreign Application Priority Data

| Mar. 29, 2004 | (JP) | ............................. | 2004-094088 |
| Sep. 24, 2004 | (JP) | ............................. | 2004-277461 |
| Dec. 3, 2004 | (JP) | ............................. | 2004-351088 |

(51) Int. Cl.
*C07D 401/14* (2006.01)
*H01L 51/00* (2006.01)

(52) U.S. Cl. .......................... 546/66; 313/498; 136/263; 428/917

(58) Field of Classification Search ................... 546/66; 428/917; 313/498; 136/263
See application file for complete search history.

(56) References Cited

U.S. PATENT DOCUMENTS 5,645,965 A   7/1997 Duff et al.

FOREIGN PATENT DOCUMENTS

| JP | 1-206349 | 8/1989 |
| JP | 2-216791 | 8/1990 |
| JP | 5-142812 | 6/1993 |
| JP | 10-133403 | 5/1998 |
| JP | 11-124382 | 5/1999 |
| JP | 11-212283 | 8/1999 |
| JP | 2000-214611 | 8/2000 |
| JP | 2001-0052204 | 1/2001 |
| JP | 2004-93791 | 3/2004 |
| JP | 2004-93803 | 3/2004 |
| JP | 2005-126367 | 5/2005 |
| JP | 2005-154409 | 6/2005 |

OTHER PUBLICATIONS

C.W. Tang et al., "Organic Electroluminescent Diodes", Applied Physics Letters, Sep. 21, 1987, pp. 913-915, vol. 51, No. 12, American Institute of Physics.
Rafik O. Loutfy et al., "Photovoltaic Properties of Metal-Free Phthalocyanines. I. Al/H$_2$ Pc Schottky Barrier Solar Cells", J. Chem. Phys., Aug. 1, 1979, pp. 1211-1217, vol. 71, No. 3, American Institute of Physics.
Yutaka Harima et al., "Spectral Sensitization in an Organic *p-n* Junction Photovoltaic Cell", Applied Physics Letters, Nov. 15, 1984, pp. 1144-1145, vol. 45, No. 10, American Institute of Physics.
Masahiro Hiramoto et al., "*p-i-n* Like Behavior in Three-Layered Organic Solar Cells Having a Co-Deposited Interlayer of Pigments", J. Appl. Phys., Oct. 15, 1992, pp. 3781-3787, vol. 72, No. 8, American Institute of Physics.
Aaron S. Lukas et al., "Biomimetic Electron Transfer Using Low Energy Excited States: A Green Perylene-Based Analogue of Chlorophyll *a*", The Journal of Physical Chemistry, Feb. 14, 2002, pp. 1299-1306, vol. 106, No. 6, The American Chemical Society.
Jovan M. Giaimo et al., "Excited-State Symmetry Breaking in Cofacial and Linear Dimers of a Green Perylenediimide Chlorophyll Analogue Leading to Ultrafast Charge Separation", Journal of the American Chemical Society, Jul. 24, 2002, pp. 8530-8531, vol. 124, No. 29, American Chemical Society.
Scott E. Miller et al., "Ultrafast Electron Transfer Reactions Initiated by Excited CT States of Push-Pull Perylenes", Chemical Physics, Jan. 1, 2002, pp. 167-183, vol. 275, Nos. 1-3, Elsevier Science B.V.

(Continued)

*Primary Examiner*—Charanjit S Aulakh
(74) *Attorney, Agent, or Firm*—Buchanan Ingersoll & Rooney PC

(57) ABSTRACT

Disclosed is a novel compound suitable as an electron transporting material for organic electronic devices. Also disclosed is an organic electronic device using such a compound which has higher sensitivity and longer life than conventional organic electronic devices.

Specifically disclosed is a compound having a structure wherein structural units represented by the general formula (1) below are bonded to one another without a linking group,

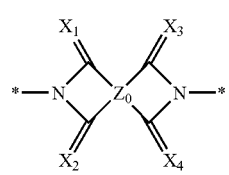

(1)

wherein, in the formula, $X_1$ to $X_4$ independently represent an oxygen atom, a sulfur atom or $NR_0$ (wherein $R_0$ represents a hydrogen atom, or a substituted or unsubstituted monovalent organic group); $Z_0$ represents a tetravalent organic group; and * represents a bonding position.

5 Claims, 1 Drawing Sheet

OTHER PUBLICATIONS

Martin P. Debreczeny et al., "Femtosecond Optical Control of Charge Shift within Electron Donor-Acceptor Arrays: An Approach to Molecular Switches", Journal of the American Chemical Society, Aug. 28, 1996, pp. 8174-8175, vol. 118, No. 34, American Chemical Society.

Aaron S. Lukas et al., "Femtosecond Optical Switching of Electron Transport Direction in Branched Donor-Acceptor Arrays", The Journal of Physical Chemistry, Feb. 10, 2000, pp. 931-940, vol. 104, No. 5, The American Chemical Society.

Ulrich Heinen et al., "High Time Resolution Q-Band EPR Study of Sequential Electron Transfer in a Triad Oriented in a Liquid Crystal", The Journal of Physical Chemistry, Mar. 14, 2002, pp. 1933-1937, vol. 106, No. 10, The American Chemical Society.

Ken Okamoto et al., "Effects of Metal Ions on Photoinduced Electron Transfer in Zinc Porphyrin-Naphthalenediimide Linked Systems", Chemistry-A European Journal, Jan. 23, 2004, pp. 474-483, vol. 10, No. 2, Wiley-VCH Verlag GmbH & Co., KGaA, Weinheim.

Yukie Mori et al., "Spin Effects on Decay Dynamics of Charge-Separated States Generated by Photoinduced Electron Transfer in Zinc Porphyrin-Naphthalenediimide Dyads", The Journal of Physical Chemistry, May 9, 2002, pp. 4453-4467, vol. 106, No. 18, The American Chemical Society.

R.A. Dine-Hart et al., "Effect of Structural Variations on the Thermo-Oxidative Stability of Aromatic Polyimides", Die Makromolekulare Chemie, Mar. 14, 1972, pp. 237-254, Hüthig & Wepf Verlag•Basel.

Heinz Langhals et al., "Intense Dyes Through Chromophore-Chromophore Interactions: Bi- and Trichromophoric Perylene-3,4:9,10-bis(dicarboximide)s", Angewandte Chemie-International Edition, Apr. 20, 1998, pp. 952-955, vol. 37, No. 7, Wiley-VCH Verlag GmbH, Weinheim.

COMPOUND AND ORGANIC ELECTRONIC DEVICE USING THE SAME

TECHNICAL FIELD

The present invention relates to a novel compound and an organic electronic device using the same. More particularly, the invention relates to an electrophotographic photoconductor, an organic transistor, an organic electroluminescent device and an organic solar cell.

BACKGROUND ART

In recent years, organic electronic materials have been paid to attention. The organic electronic material refers to those which are intended to apply organic materials as a new material in place of semiconductors using the current inorganic materials. Among practical electronic devices using organic materials, so-called active devices using active functions generated by flowing the current to materials have extremely been limited. The most typical example thereof is an organic electrophotographic photoconductor. Some examples which have currently been under development include an organic electroluminescent device, an organic solar cell, an organic transistor and the like.

As an organic electronic material, there are a hole transporting material (organic p-type semiconductor) in which a hole acts as a charge carrier and an electron transporting material (organic n-type semiconductor) in which a electron acts as a charge carrier. Since material development up to now has been mainly carried out for hole transporting materials, a large number of hole transporting materials have been known. Electron conduction hardly takes place due to formation of deep trap level resulted from oxygen molecules having a large electron affinity in electron transport so that the number of electron transporting materials is extremely small as compared to that of hole transporting materials.

The organic electronic device is used in combination of a hole transporting material and an electron transporting material in many cases. There has been no high performance electron transporting material as yet, so there have been some problems in the organic electronic device. Various devices as described above will be explained in more detail below.

An organic electrophotographic photoconductor (OPC) has been widely put to practical use from the viewpoint that characteristics of a photoconductor can be designed in many ways because of pollution-free property, low cost and some degree of freedom of material selection. As for a photosensitive layer of OPC, there have been proposed a so-called function-separated type photoconductor such as dual-layered type photoconductor in which a charge generation layer and a charge transport layer are stacked, and a so-called single-layered photoconductor in which a charge generating material and a charge transporting material are dispersed in a single photosensitive layer, and the like.

Charge transporting materials used in these photoconductors are required to have high carrier mobility. However, since most charge transporting materials with high carrier mobility have been used for transporting holes, OPC actually provided for the practical use has been limited to a dual-layered type photoconductor in a negatively charged process with a charge transport layer provided on an outermost layer from the viewpoint of mechanical strength. However, OPC in a negatively charged process uses the negative corona discharge. So, there are some problems such that it is unstable as compared with that using the positive corona discharge, and ozone, nitrogen oxide or the like is generated and adhered on a surface of the photoconductor, easily causing physical and chemical deterioration, and exerting bad influence on the use environment.

In order to solve the above problems, OPC which can be used for positively charged process is effective. For this reason, an electron transporting material is required to be used as a charge transporting material. 2,4,7-Trinitrofluorenone is known as an electron transporting material. However, such a substance is not sufficient in solubility to and compatibility with a solvent or a binder polymer, and it does not have sufficient properties to actually constitute a photosensitive layer. Further, its use has been stopped because of its carcinogenicity as well.

In late years, for example, in Patent Document 1, there has been proposed to use a compound having a diphenoquinone structure or a benzoquinone structure as an electron transporting material for an electrophotographic photoconductor. Further, in Patent Document 2, there has been proposed to use a benzenetetracarboxylic acid diimide compound as an electron transporting material for an electrophotographic photoconductor.

However, since conventional electron transporting materials such as diphenoquinone derivatives, benzoquinone derivatives, benzenetetracarboxylic acid diimide compounds and the like have low compatibility with binder polymers, there are problems such as precipitation and the like. Further, the amount capable of dispersing in a photosensitive layer is limited, thus increasing the hopping distance. So, under low electric field, the movement of electrons hardly takes place. Therefore, it is difficult to make the conventional photoconductor comprising an electron transporting material into a photoconductor with excellent electron transporting capability.

A thin film transistor has been widely used as a switching device for liquid crystal display device or the like. In the past, a thin film transistor (TFT) has been prepared by using amorphous silicon or polycrystalline silicon. However, CVD apparatus to be used for the production of TFT using this silicon is highly expensive so that there is a problem in that the production of large-sized display devices using TFT or the like is accompanied by a sharp increase in the production cost. Further, the process for making amorphous silicon or polycrystalline silicon into a film is carried out at a very high temperature, thus the kind of materials which can be used as a substrate is limited. Therefore, there is a problem that and lightweight polymer substrate or the like cannot be used.

In order to solve the above problems, TFT using an organic semiconductor has been proposed instead of using amorphous silicon or polycrystalline silicon. A thin film transistor using an organic semiconductor has been actively developed little by little since late 1980s, and in late years, basic performance has exceeded characteristics of a thin film transistor made of amorphous silicon. As a method for forming a film used for forming TFT with an organic semiconductor, there have been known a vacuum deposition method, a coating method and the like. However, according to these film-forming methods, large-sized devices can be realized while holding down an increase in cost, and a process temperature required for film-forming can be relatively low. For this reason, TFT using an organic semiconductor (hereinafter referred to as "organic TFT") is provided with an advantage in which limitation on the selection of to be used as a substrate is low, and it is expected to be put to practical use. Further, a TFT has also been paid attention to possibility of use as a smart card or a security tag.

Performance of an organic TFT mainly depends on charge mobility of an organic compound and an on/off ratio of current. Therefore, ideally, it needs to have low conductivity, along with high charge mobility, while the current is off. The on/off ratio herein refers to a ratio of the current between the source and drain when the organic TFT is on to the current between the source and drain when the organic TFT is off.

Organic substances are used in simple substance or in combination with other compounds for an organic compound layer of an organic TFT. The organic substances contain conjugated polymers, multiers of thiophene or the like, metal phthalocyanines or condensed aromatic hydrocarbons such as pentacene or the like. However, as described above, a study on an organic TFT has been actively carried out, whereas any of the conventional organic TFT was slow in its operational speed and could not have practically sufficient on/off ratio since performance of a compound in use was insufficient.

An organic electroluminescent device is excellent in impact resistance because it is a perfect solid device and its visibility is high because of its self-emission property. Therefore, at present, the organic electroluminescent device has been actively studied as a flat panel type display. This organic electroluminescent device has a structure of successively stacking a hole injecting electrode, an organic layer and an electron injecting electrode on a transparent glass substrate. As the hole injecting electrode, an electrode material having a high work function such as Au (gold) or ITO (indium tin oxide alloy) is used, while as the electron injecting electrode, an electrode material having a low work function such as Mg is used. Further, for the aforementioned hole injecting and transporting layer, an organic material having a property of a p-type semiconductor has been used, while for the electron injecting and transporting layer, an organic material having a property of an n-type semiconductor has been used.

The principle of light emission of the organic electroluminescent device is considered that excitons are generated by the recombination of holes injected from the hole injecting electrode and electrons from the electron injecting electrode at an interface between a light-emitting layer and a hole (or electron) transporting layer, and in the light-emitting layer, and the excitons serve to excite molecules of a light-emitting material constituting the light-emitting layer.

However, electroluminescent materials are classified into organic and inorganic electroluminescent materials. As an organic electrolumihescent material, single crystalline anthracene emitting blue light has been known from the past, while as an inorganic electroluminescent material, a compound semiconductor has been well known. However, an anthracene single crystal is thick, i.e., from several tens of μm to several mm. So, in order to emit light from this single crystal, a drive voltage of several hundreds of V was needed. Further, there has been a problem such that the electron injecting efficiency is low for injecting both charges of holes and electrons to this single crystal because the anthracene single crystal is an organic material of a single composition. Further, a drive voltage necessary for light emission of the crystal could be reduced by thinning this anthracene single crystal, but it was difficult to improve the electron injecting efficiency.

In Non-Patent Document 1 by Tang and VanSlyke of Kodak Company in 1987, there has been reported a device composed of two layers such as a hole transporting layer and an electron transporting light-emitting layer which emits green light with good efficiency at a lower drive voltage of approximately 10 V, as compared to the conventional organic electroluminescent device of a single-layered structure.

The reason why the light-emitting efficiency is improved due to this multi-layered structure as compared to the past is because a balance of holes and electrons injected from electrodes can be achieved. In the above devices, the hole transporting layer has the function of injecting holes from an anode to the electron transporting light-emitting layer and at the same time prevents electrons injected from a cathode from running away to the anode without the recombination with holes for playing a role of blocking electrons up in the electron transporting light-emitting layer. For this reason, by the effect of blocking electrons by this hole transporting layer, the recombination of holes and electrons takes place with much better efficiency, as compared to the conventional single layer devices, thus enabling a big reduction in the drive voltage.

Moreover, excitons generated by the recombination also have the function of preventing radiationless deactivation on a surface of a metal electrode. From this point of view, a hole blocking material has been under development. A hole blocking layer is located between the light-emitting layer and the electron injecting and transporting layer, and has the effect of blocking charges (holes or electrons) or excitons up in the light-emitting layer. The following compounds have been reported so far. Oxadiazole derivatives (Patent Document 3) have been widely used until now, but there is a problem such that crystallization easily takes place. Even when other compounds are used, there are some problems such as an increase in the drive voltage and the like. For this reason, in order to develop an organic electroluminescent device which has much higher light-emitting efficiency and longer lifetime, development of an electron injecting and transporting material has been demanded.

Solar energy has been actively studied for its use as an environment-friendly energy. An inorganic semiconductor such as silicon, CdS, CdTe, CdAs and the like has been widely used for a solar cell from the viewpoint of high solar energy conversion efficiency in the past. The conversion efficiency thereof reaches about 15%, when, for example, silicon is used. However, in the solar cell using the inorganic semiconductor, since many processes such as a process of producing a single crystal, a doping process and the like are required for the production of the cell, this causes a problem of greatly increasing the production cost.

In order to reduce the cost involved in the production of this solar cell, an organic solar cell using an organic semiconductor capable of easily producing a thin film by vapor deposition, casting or the like has been studied. A solar cell using an organic semiconductor has many advantages as compared to a solar cell using an inorganic semiconductor, but the conversion efficiency is low so that such a solar cell could not be put to practical use. For example, there has been reported a so-called Schottky barrier-type device using the contact between metal-free phthalocyanine and aluminum by Loutfy et al. (Non-Patent Document 2). However, when the intensity of irradiated light is increased, the conversion efficiency is suddenly decreased or the device becomes worsened over time. This is because aluminum in an electrode becomes oxidized by oxygen in air. There has been reported a solar cell in which a perylene derivative that is an organic n-type semiconductor is connected with phthalocyanine, in place of aluminum by Tang et al. (Non-Patent Document 3). This solar cell exhibits the conversion efficiency of 1% under an artificial sunlight, achieving the highest conversion efficiency for the present. This is because the spectrum sensitivity can be enlarged because of the solar cell capable of carrying out light irradiation from a transparent electrode and generating a photogenerated charge carrier with two kinds of materials. However, the conversion efficiency is still low as compared with that of a solar cell employing an inorganic semiconductor, so the efficiency is required to be improved about 10 times more for the practical use.

One reason of the low photoelectric conversion efficiency of the organic solar cell is a difference in carrier generating mechanisms of an inorganic semiconductor and an organic semiconductor. The interlattice interaction in the inorganic semiconductor is strong so that an electron-hole pair is created directly by the light absorption. On the other hand, since the intermolecular interaction in the organic semiconductor is weak, i.e., just about 0.1 eV, the energy perturbation due to lattice defects or impurities is small, strongly bound excitons of the Frenkel type are generated by the light absorption, and usually free carriers are not directly generated.

The second reason is that an active area for the generation of optical carriers in the organic semiconductor is narrow. In the conventional simple p-n junction type organic solar cell, the width of an area activated for the generation of carriers to be formed near the junction is very narrow, and an organic semiconductor layer other than an activated area near the junction (usually about several tens of nm) becomes a dead layer which does not generate carriers even when light is absorbed.

That is, the operational principle of the organic solar cell is that the excitons generated by light absorption reaches the activated area near the junction while diffusing, and generates free carriers.

A three layer device composed of a mixed layer of phthalocyanine of an organic p-type semiconductor and a perylene derivative of an organic n-type semiconductor inserted between a p-type layer and an n-type layer of the p-n junction type organic solar cell has been reported by Yokoyama et al. (Non-Patent Document 4). The three layer device having a mixed layer exhibits light current value of two times or more than the two layer device without having the mixed layer. However, it is not possible to effectively transport light carriers generated from the mixed layer to an electrode, so much improvement of the efficiency has been required for the practical use.

[Patent Document 1] Japanese Patent Laid-Open No. 1989-206349
[Patent Document 2] Japanese Patent Laid-Open No. 1993-142812
[Patent Document 3] Japanese Patent Laid-Open No. 1990-216791
[Non-Patent Document 1] Appl. Phys. Lett., Vol. 51, No. 12 (1987), pp. 913-915
[Non-Patent Document 2] J. Chem. Phys., Vol. 71, p. 1211
[Non-Patent Document 3] Appl. Phys. Lett., Vol. 45, p. 1144
[Non-Patent Document 4] J. Appl. Phys., Vol. 72, p. 3781

DISCLOSURE OF THE INVENTION

An object of the present invention is to solve the technical problems as described above and to provide a novel compound which is suitable as an electron transporting material in an organic electronic material and an organic electronic device using the compound which has higher sensitivity and longer lifetime than the conventional organic electronic device.

The present inventors have conducted an extensive study and, as a result, have found that a novel compound represented by the general formula (1) was excellent in thin film-forming performance and electron transporting capability, was used as an electron transporting material in an organic electronic material for enabling to produce a device with high sensitivity and high functionality. Thus, the present invention has been completed.

That is, the present invention is specified by the following matters.

[1] a compound having a structure wherein structural units represented by the general formula (1) are bonded to one another without a linking group,

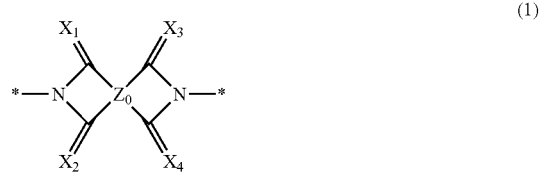

(1)

wherein, in the formula, $X_1$ to $X_4$ each independently represent an oxygen atom, a sulfur atom or $NR_0$ (wherein $R_0$ represents a hydrogen atom, or a substituted or unsubstituted monovalent organic group); $Z_0$ represents a tetravalent organic group; and * represents a bonding position;

[2] the compound as described in [1], comprising structural units represented by the general formula (2),

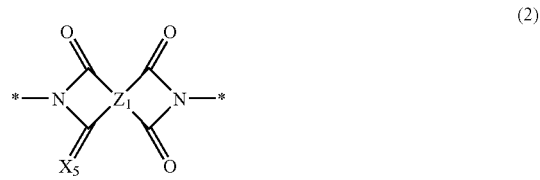

(2)

wherein, in the formula, $Z_1$ represents a tetravalent organic group; $X_5$ represents an oxygen atom, a sulfur atom or $NR_0$ (wherein $R_0$ represents a hydrogen atom, or a substituted or unsubstituted monovalent organic group); and * represents a bonding position;

[3] the compound as described in [1] or [2], represented by the general formula (3),

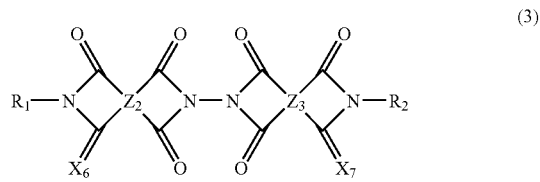

(3)

wherein, in the formula, $Z_2$ and $Z_3$ each independently represent a tetravalent organic group constituting a tetracarboxylic acid and its derivatives; $X_6$ and $X_7$ each independently represent an oxygen atom, a sulfur atom or $NR_0$ (wherein $R_0$ represents a hydrogen atom, or a substituted or unsubstituted monovalent organic group); when $X_6$ is a nitrogen atom, $X_6$ may be bonded to $R_1$ for forming a ring structure; when $X_7$ is a nitrogen atom, $X_7$ may be bonded to $R_2$ for forming a ring structure; and $R_1$ and $R_2$ each independently represent a hydrogen atom, a substituted or unsubstituted aryl group, a substituted or unsubstituted alkyl group, a substituted or unsubstituted cycloalkyl group, a substituted or unsubstituted aralkyl group or a group selected from the group consisting of the following general formula (4),

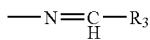
(4)

wherein, in the formula, $R_3$ represents a substituted or unsubstituted aryl group, a substituted or unsubstituted alkyl group, or a substituted or unsubstituted cycloalkyl group;

[4] an electrophotographic photoconductor containing at least one kind of the compounds as described in any one of [1] to [3];

[5] an organic transistor containing at least one kind of the compounds as described in any one of [1] to [3];

[6] an organic solar cell containing at least one kind of the compounds as described in any one of [1] to [3]; and

[7] an organic electroluminescent device containing at least one kind of the compounds as described in any one of [1] to [3].

The novel compound obtained by the present invention is superior in the ability of electron transport. When the compound is used for an organic electronic device, an organic electronic device having high sensitivity and high durability which is also superior in electrical properties, repeating stability and thin film stability is obtained.

The novel compound of the present invention is useful in various organic electronic devices including an organic electrophotographic photoconductor, an organic transistor, an organic solar cell and an organic electroluminescent device, and is capable of providing the organic electronic devices.

BEST MODE FOR CARRYING OUT THE INVENTION

Figure 1:
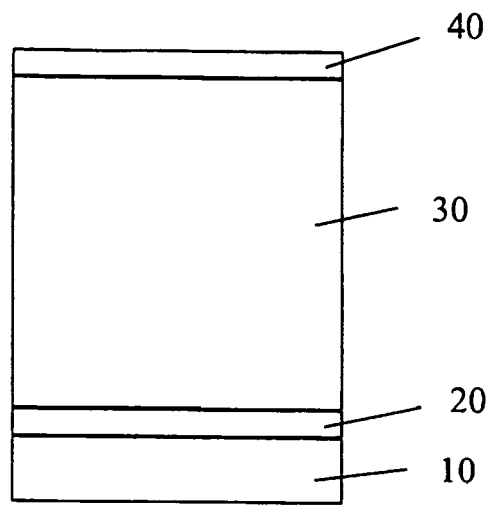
FIG. 1 is a schematic cross-sectional view of the electrophotographic photoconductor according to the present invention.

The present invention will be described in more detail below.

The novel compound of the present invention refers to a compound having a structure wherein structural units represented by the general formula (1) are bonded to one another without a linking group,

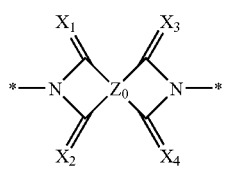
(1)

wherein, in the formula, $X_1$ to $X_4$ each independently represent an oxygen atom, a sulfur atom or $NR_0$ (wherein $R_0$ represents a hydrogen atom, or a substituted or unsubstituted monovalent organic group); $Z_0$ represents a tetravalent organic group; and * represents a bonding position.

The novel compound of the present invention may have a structure wherein structural units represented by the above general formula (1) are bonded to one another without a linking group, and the number of structural units to be bonded or the number of structures itself with structural units bonded thereto is not particularly limited either.

$X_1$ to $X_4$ represented by the general formula (1) each independently represent an oxygen atom, a sulfur atom or $NR_0$ (wherein $R_0$ represents a hydrogen atom, or a substituted or unsubstituted monovalent organic group).

Herein, $R_0$ represents a hydrogen atom, or a substituted or unsubstituted monovalent organic group. Examples of the monovalent organic group include an aryl group, an alkyl group, a cycloalkyl group and an aralkyl group.

The aryl group is not particularly limited, but examples thereof preferably include a substituted or unsubstituted carboncyclic aromatic group having 6 to 30 carbon atoms and a substituted or unsubstituted heterocyclic aromatic group having 3 to 25 carbon atoms, more preferably a substituted or unsubstituted carboncyclic aromatic group having 6 to 25 carbon atoms and a substituted or unsubstituted heterocyclic aromatic group having 4 to 12 carbon atoms, and further preferably a substituted or unsubstituted carboncyclic aromatic group having 6 to 22 carbon atoms and a substituted or unsubstituted heterocyclic aromatic group having 4 to 10 carbon atoms. Concrete examples thereof include a phenyl group, a naphthyl group, an anthryl group, a biphenyl group, a thienyl group, a bithienyl group, a furyl group, a pyridyl group and the like.

The alkyl group is not particularly limited, but examples thereof include a straight chain or branched alkyl group having 1 to 25 carbon atoms and preferably having 1 to 16 carbon atoms. Concrete examples thereof include straight chain alkyl groups such as a methyl group, an ethyl group, an n-propyl group, an n-butyl group, an n-pentyl group, an n-hexyl group, an n-heptyl group, an n-octyl group and a decyl group, and branched alkyl groups such as an i-propyl group, an s-butyl group, a t-butyl group, a methylpropyl group, a dimethylpropyl group, an ethylpropyl group, a diethylpropyl group, a methylbutyl group, a dimethylbutyl group, a methylpentyl group, a dimethylpentyl group, a methylhexyl group, a dimethylhexyl group and the like.

The cycloalkyl group is not particularly limited, but examples thereof include cycloalkyl groups having 1 to 25 carbon atoms and preferably having 1 to 10 carbon atoms. Concrete examples include groups having a same type ring from cyclopropane to cyclodecane; and an alicyclic ring having an alkyl substituent such as methylcyclopentane, dimethylcyclopentane, methylcyclohexane, dimethylcyclohexane, trimethylcyclohexane, tetramethylcyclohexane, ethylcyclohexane, diethylcyclohexane and the like.

The aralkyl group is not particularly limited, but preferable examples thereof include aralkyl groups having 6 to 14 carbon atoms. Concrete examples include a benzyl group, a 1-phenylethyl group, a 3-phenylpropyl group, a 4-phenylbutyl group, a 5-phenylpentyl group, a 6-phenylhexyl group, a benzhydryl group, a trityl group, a phenethyl group and the like.

Furthermore, an aryl group, an alkyl group, a cycloalkyl group and an aralkyl group corresponding to $R_0$ may have a substituent. Concrete examples of the substituent include an alkyl group, an alkoxy group, an alkylthio group, an alkoxyalkyl group, a halogenated alkyl group, a halogen atom and the like. Incidentally, the substitution position of these substituents is not particularly limited.

As the alkyl group, preferably used is an alkyl group which may have a substituent of 1 to 10 carbon atoms. Concrete examples thereof include straigh chain alkyl groups such as a methyl group, an ethyl group, an n-propyl group and an n-butyl group; and branched alkyl groups such as an i-propyl group, an s-butyl group and a t-butyl group.

As the alkoxy group, preferably used is an alkoxy group which may have a substituent of 1 to 10 carbon atoms. Concrete examples thereof include a methoxy group, an ethoxy group, a propoxy group, an isopropoxy group and the like.

As the alkylthio group, preferably used is an alkylthio group which may have a substituent of 1 to 10 carbon atoms. Concrete examples thereof include a methylthio group, an ethylthio group, a propylthio group, an isopropylthio group and the like.

The alkoxyalkyl group has a structure wherein an alkoxyl group is substituted at an alkyl group, and is preferably an alkoxyalkyl group having 1 to 20 carbon atoms and more preferably an alkoxyalkyl group having 1 to 10 carbon atoms. Concrete examples thereof include a methoxymethyl group, an ethoxymethyl group, a butoxymethyl group, an ethoxyethyl group, a butoxyethyl group, a 2-methoxyethyl group and the like. The substitution position of the alkoxyl group on the alkyl group is not particularly limited, and the alkoxyl group may be on any of carbon atoms of alkyl chains, for example, in the middle, at the end or the like of the alkyl group.

The halogenated alkyl group has a structure wherein a halogen atom is substituted at an alkyl group, and is preferably a halogenated alkyl group having 1 to 20 carbon atoms and more preferably a halogenated alkyl group having 1 to 10 carbon atoms. Concrete examples thereof include a trifluoromethyl group, a 2,2,2-trifluoroethyl group, a 2-fluoroethyl group, a 2-chloroethyl group and the like. The halogen atom may be selected from any of a fluorine atom, a chlorine atom, a bromine atom and an iodine atom, but a fluorine atom and a chlorine atom are preferable. The number of halogen atoms is not particularly limited, but it is 1 or more. For example, all hydrogen atoms may be substituted with halogen atoms like perfluoro-.

Examples of the halogen atom include a fluorine atom, a chlorine atom, a bromine atom and an iodine atom. Preferably used are a fluorine atom and a chlorine atom.

$Z_0$ represented by the general formula (1) represents a tetravalent organic group. The tetravalent organic group is not particularly limited, but suitable examples thereof include an alicyclic group, an aliphatic group, an aromatic group, or an aromatic group wherein a plurality of aromatic groups are directly bonded or bonded by a crosslinking member such as a carbonyl group, a sulfonic group, a sulfoxide group, an ether group, a sulfide group or the like.

The alicyclic group is not particularly limited, but preferably used is an alicyclic group having 4 to 25 carbon atoms and preferably having 1 to 10 carbon atoms. Concrete examples thereof include a cyclobutanetetrayl group, a cyclopentanetetrayl group, a cyclohexanetetrayl group, a bicyclohexanetetrayl group and the like.

The aliphatic group is not particularly limited, but preferably used is an aliphatic group having 4 to 25 carbon atoms and preferably having 4 to 10 carbon atoms. Concrete examples thereof include a butanetetrayl group, a pentanetetrayl group, a hexanetetrayl group and the like.

The aromatic group is not particularly limited, but examples thereof preferably include a substituted or unsubstituted carboncyclic aromatic group having 6 to 30 carbon atoms and a substituted or unsubstituted heterocyclic aromatic group having 3 to 25 carbon atoms, more preferably a substituted or unsubstituted carboncyclic aromatic group having 6 to 25 carbon atoms and a substituted or unsubstituted heterocyclic aromatic group having 4 to 12 carbon atoms, and further preferably a substituted or unsubstituted carboncyclic aromatic group having 6 to 22 carbon atoms and a substituted or unsubstituted heterocyclic aromatic group having 4 to 10 carbon atoms.

"*" represented by the general formula (1) represents a bonding position of a constitutional unit.

A bonding state of the structural units represented by the general formula (1) may be an oligomer or a polymer. In case of an oligomer, the number of structural units to be bonded is preferably from 2 to 10 and more preferably from 2 to 6. When the bonding number is too large, it might be difficult to separate oligomer as a single compound so that such the number might possibly be undesirable in view of securing stabilized performance. Furthermore, in case of a polymer, the number of structural units to be bonded is preferably from 100 to 1,000 and more preferably from 200 to 800.

Concrete examples of structural units represented by the general formula (1) can be exemplified, but are not limited to these structural units.

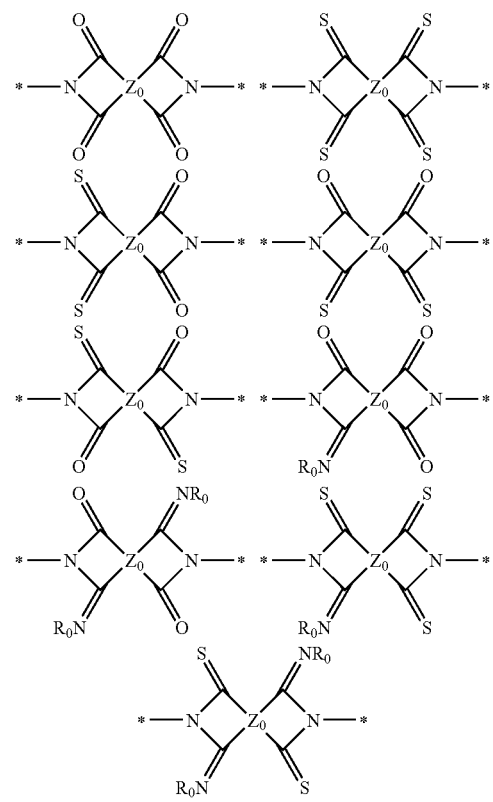

In the above concrete examples, the following examples are more preferable.

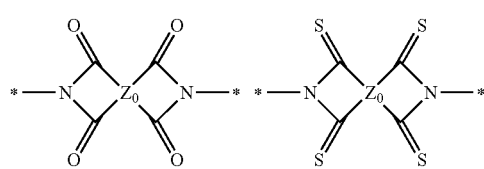

-continued

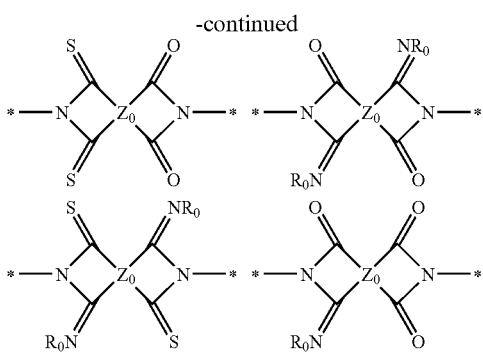

In the concrete examples of structural units represented by the general formula (1), examples comprising structural units represented by the following general formula (2) are particularly preferable.

wherein, in the formula, $Z_1$ represents a tetravalent organic group; $X_5$ represents an oxygen atom, a sulfur atom or $NR_0$ (wherein $R_0$ represents a hydrogen atom, or a substituted or unsubstituted monovalent organic group); and * represents a bonding position.

Herein, at least one of the structural units represented by the general formula (2) may be contained in a compound having a structure wherein structural units represented by the general formula (1) are bonded to one another without a linking group, and structural units are not particularly limited (all structural units may, of course, be any of those represented by the general formula (2)).

$X_5$ in the general formula (2) represents an oxygen atom, a sulfur atom or $NR_0$ (wherein $R_0$ represents a hydrogen atom, or a substituted or unsubstituted monovalent organic group). $R_0$ herein is the same as $R_0$ in $X_1$ to $X_4$ of the aforementioned general formula (1).

$Z_1$ in the general formula (2) represents a tetravalent organic group. The tetravalent organic group is not particularly limited, but preferable examples thereof include an alicyclic group, an aliphatic group, an aromatic group, or an aromatic group wherein a plurality of aromatic groups are directly bonded or bonded to one another by a crosslinking member such as a carbonyl group, a sulfonic group, a sulfoxide group, an ether group, a sulfide group or the like.

The alicyclic group is not particularly limited, but preferably used is an alicyclic group having 4 to 25 carbon atoms and preferably having 4 to 10 carbon atoms. Concrete examples thereof include a cyclobutanetetrayl group, a cyclopentanetetrayl group, a cyclohexanetetrayl group, a bicyclohexanetetrayl group and the like.

The aliphatic group is not particularly limited, but preferably used is an aliphatic group having 4 to 25 carbon atoms and preferably having 4 to 10 carbon atoms. Concrete examples thereof include a butanetetrayl group, a pentanetetrayl group, a hexanetetrayl group and the like.

The aromatic group is not particularly limited, but examples thereof preferably include a substituted or unsubstituted carboncyclic aromatic group having 6 to 30 carbon atoms and a substituted or unsubstituted heterocyclic aromatic group having 3 to 25 carbon atoms, more preferably a substituted or unsubstituted carboncyclic aromatic group having 6 to 25 carbon atoms and a substituted or unsubstituted heterocyclic aromatic group having 4 to 12 carbon atoms, and further preferably a substituted or unsubstituted carboncyclic aromatic group having 6 to 22 carbon atoms and a substituted or unsubstituted heterocyclic aromatic group having 4 to 10 carbon atoms.

Furthermore, "*" represented by the general formula (2) represents a bonding position of a constitutional unit.

In concrete examples of the constitutional unit represented by the general formula (2) and the compound comprising the constitutional unit, compounds represented by the following general formula (3) are particularly preferable,

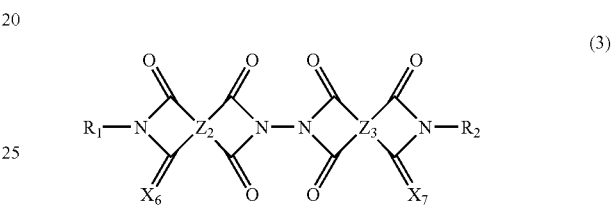

wherein, in the formula, $Z_2$ and $Z_3$ each independently represent a tetravalent organic group constituting a tetracarboxylic acid and its derivatives; $X_6$ and $X_7$ each independently represent an oxygen atom, a sulfur atom or $NR_0$ (wherein $R_0$ represents a hydrogen atom, or a substituted or unsubstituted monovalent organic group); when $X_6$ is a nitrogen atom, $X_6$ may be bonded to $R_1$ for forming a ring structure; when $X_7$ is a nitrogen atom, $X_7$ may be bonded to $R_2$ for forming a ring structure; or $R_1$ and $R_2$ each independently represent a hydrogen atom, a substituted or unsubstituted aryl group, a substituted or unsubstituted alkyl group, a substituted or unsubstituted cycloalkyl group, a substituted or unsubstituted aralkyl group or a group selected from the group consisting of the following general formula (4),

wherein, in the formula, $R_3$ represents a substituted or unsubstituted aryl group, a substituted or unsubstituted alkyl group, or a substituted or unsubstituted cycloalkyl group.

A compound represented by the general formula (3) will be explained in more detail.

First, $Z_2$ and $Z_3$ in the compound represented by the general formula (3) are explained. $Z_2$ and $Z_3$ are each independently a tetravalent organic group constituting a tetracarboxylic acid and its derivatives. Examples of the tetravalent organic group include an alicyclic group, an aliphatic group, an aromatic group, or an aromatic group wherein a plurality of aromatic groups are directly bonded or bonded to one another by a crosslinking member such as a carbonyl group, a sulfonic group, a sulfoxide group, an ether group, a sulfide group or the like.

The alicyclic group is not particularly limited, but preferably used is an alicyclic group having 4 to 25 carbon atoms and preferably having 4 to 10 carbon atoms. Concretely, for example, in a tetravalent organic group constituting a tetracarboxylic acid and its derivatives, when the tetracarboxylic acid and its derivatives are tetracarboxylic dianhydrides, and the tetravalent organic group is an alicyclic group, i.e., concrete examples of the tetracarboxylic dianhydride having an alicyclic group include 1,2,3,4-cyclobutane tetracarboxylic dianhydride, 1,2-dimethyl-1,2,3,4-cyclobutane tetracarboxylic dianhydride, 1,3-dimethyl-1,2,3,4-cyclobutane tetracarboxylic dianhydride, 1,2,3,4-tetramethyl-1,2,3,4-cyclobutane tetracarboxylic dianhydride, 1,2,3,4-cyclopentane tetracarboxylic dianhydride, 1,2,4,5-cyclohexane tetracarboxylic dianhydride, 3,3',4,4'-dicyclohexyl tetracarboxylic dianhydride, cis-3,7-dibutylcycloocta-1,5-diene-1,2,5,6-tetracarboxylic dianhydride, 2,3,5-tricarboxycyclopentyl acetic dianhydride, 3,5,6-tricarboxy-2-carboxynorbornane-2:3,5:6-dianhydride, 3,4-dicarboxy-1,2,3,4-tetrahydro-1-naphthalene succinic dianhydride, 2,3,4,5-tetrahydrofuran tetracarboxylic dianhydride and the like.

The aliphatic group is not particularly limited, but preferably used is an aliphatic group having 4 to 25 carbon atoms and preferably having 4 to 10 carbon atoms. Concretely, for example, in a tetravalent organic group constituting a tetracarboxylic acid and its derivatives, when the tetracarboxylic acid and its derivatives are tetracarboxylic dianhydride, and the tetravalent organic group is an aliphatic group, i.e., concrete examples of the tetracarboxylic dianhydride having an aliphatic group include butane tetracarboxylic dianhydride, pentane tetracarboxylic dianhydride and the like.

The aromatic group is not particularly limited, but examples thereof preferably include a substituted or unsubstituted carboncyclic aromatic group having 6 to 30 carbon atoms and a substituted or unsubstituted heterocyclic aromatic group having 3 to 25 carbon atoms, more preferably a substituted or unsubstituted carboncyclic aromatic group having 6 to 25 carbon atoms and a substituted or unsubstituted heterocyclic aromatic group having 4 to 12 carbon atoms, and further preferably a substituted or unsubstituted carboncyclic aromatic group having 6 to 22 carbon atoms and a substituted or unsubstituted heterocyclic aromatic group having 4 to 10 carbon atoms.

Concretely, for example, in a tetravalent organic group constituting a tetracarboxylic acid and its derivatives, when the tetracarboxylic acid and its derivatives are tetracarboxylic acid dianhydride, and the tetravalent organic group is an aromatic group, i.e., concrete examples of the tetracarboxylic dianhydride having an aromatic group include pyromellitic dianhydride, 3,3',4,4'-benzophenone tetracarboxylic dianhydride, 3,3',4,4'-biphenylsulfone tetracarboxylic dianhydride, 1,2,5,6-naphthalene tetracarboxylic dianhydride, 1,4,5,8-naphthalene tetracarboxylic dianhydride, 2,3,6,7-naphthalene tetracarboxylic dianhydride, 2,3,6,7-anthracene tetracarboxylic dianhydride, 1,2,5,6-anthracene tetracarboxylic dianhydride, 3,3',4,4'-biphenylether tetracarboxylic dianhydride, 3,3',4,4'-dimethyl diphenylsilane tetracarboxylic dianhydride, 3,3',4,4'-tetraphenylsilane tetracarboxylic dianhydride, 1,2,3,4-furan tetracarboxylic dianhydride, 4,4'-bis(3,4-dicarboxyphenoxy)diphenylsulfide dianhydride, 4,4'-bis(3,4-dicarboxyphenoxy)diphenylsulfone dianhydride, 4,4'-bis(3,4-dicarboxyphenoxy)diphenylpropane dianhydride, 3,3',4,4'-perfluoroisopropylidene diphthalic dianhydride, 3,3',4,4'-biphenyl tetracarboxylic dianhydride, 2,3,3',4-biphenyl tetracarboxylic dianhydride, 2,3,4,5-pyridine tetracarboxylic dianhydride, 2,6-bis(3,4-dicarboxyphenyl)pyridine dianhydride, bis(phthalic acid)phenylphosphine oxide dianhydride, p-phenylene-bis(triphenyl phthalic acid)dianhydride, m-phenylene-bis(triphenyl phthalic acid)dianhydride, bis(triphenyl phthalic acid)-4,4'-diphenyl ether dianhydride, bis(triphenyl phthalic acid)-4,4'-diphenylmethane dianhydride and the like.

However, such compounds are excluded, wherein any one of $Z_2$ and $Z_3$ is a perylene derivative. When any one of $Z_2$ and $Z_3$ is a perylene derivative, that compound has low compatibility with the binder polymer used in an electrophotographic photoconductor, resulting in a problem of precipitation, or the amount capable of dispersing in a photosensitive layer is limited, resulting in an increase of the hopping distance, so there occurs a problem such that electron mobility becomes lowered under low electric field.

Furthermore, a tetravalent organic group constituting a tetracarboxylic acid and its derivatives corresponding to $Z_2$ and $Z_3$ may have a substituent. Concrete examples of the substituent include an alkyl group, an alkoxy group, an alkylthio group, an aryl group, an aryloxy group, an arylthio group, a halogenated alkyl group, a halogen atom, a carboxyl group which may be esterified, a cyano group and the like. Incidentally, the substitution position of these substituents is not particularly limited.

As the alkyl group, preferably used is an alkyl group which may have a substituent having 1 to 10 carbon atoms. Concrete examples thereof include a straight chain alkyl group such as a methyl group, an ethyl group, an n-propyl group and an n-butyl group; and a branched alkyl group such as an i-propyl group, an s-butyl group and a t-butyl group.

As the alkoxy group, preferably used is an alkoxy group which may have a substituent having 1 to 10 carbon atoms. Concrete examples thereof include a methoxy group, an ethoxy group, a propoxy group, an isopropoxy group and the like.

As the alkylthio group, preferably used is an alkylthio group which may have a substituent having 1 to 10 carbon atoms. Concrete examples thereof include a methylthio group, an ethylthio group, a propylthio group, an isopropylthio group and the like.

As the aryl group, preferably used is an aryl group comprising a carboncyclic aromatic group which may have a substituent having 6 to 30 carbon atoms and a heterocyclic aromatic group which may have a substituent having 3 to 25 carbon atoms. Concrete examples thereof include a phenyl group, a naphthyl group, a biphenyl group, a thienyl group, a bithienyl group and the like.

As the aryloxy group, preferably used is an aryloxy group comprising a carboncyclic aromatic group which may have a substituent having 6 to 30 carbon atoms and a heterocyclic aromatic group which may have a substituent having 3 to 25 carbon atoms. Concrete examples thereof include a phenyloxy group, a naphthyloxy group, a biphenyloxy group, a thienyloxy group, a bithienyloxy group, a pyridyloxy group and the like.

As the arylthio group, preferably used is an arylthio group comprising a carboncyclic aromatic group which may have a substituent having 6 to 30 carbon atoms and a heterocyclic aromatic group which may have a substituent having 3 to 25 carbon atoms. Concrete examples thereof include a phenylthio group, a naphthylthio group, a biphenylthio group, a thienylthio group, a bithienylthio group, a pyridylthio group and the like.

The halogenated alkyl group has a structure wherein a halogen atom is substituted at an alkyl group, and examples thereof preferably include a halogenated alkyl group having 1 to 20 carbon atoms and more preferably a halogenated alkyl group having 1 to 10 carbon atoms. Concrete examples thereof include a trifluoromethyl group, a 2,2,2-trifluoroethyl group, a 2-fluoroethyl group, a 2-chloroethyl group and the like. The halogen atom may be selected from any of a fluorine atom, a chlorine atom, a bromine atom and an iodine atom, but a fluorine atom and a chlorine atom are preferable. The number of halogen atoms is not particularly limited, but it is 1 or more. For example, all hydrogen atoms may be substituted with halogen atoms like perfluoro derivatives.

Examples of the halogen atom include a fluorine atom, a chlorine atom, a bromine atom and an iodine atom. Preferably used are a fluorine atom and a chlorine atom.

Next, $X_6$ and $X_7$ in the compound represented by the general formula (3) will be explained. $X_6$ and $X_7$ each independently represent an oxygen atom, a sulfur atom or $NR_0$ (wherein $R_0$ represents a hydrogen atom, or a substituted or unsubstituted monovalent organic group). When $X_6$ is a nitrogen atom, $X_6$ may be bonded to $R_1$ for forming a ring structure, and when $X_7$ is a nitrogen atom, $X_7$ may be bonded to $R_2$ for forming a ring structure.

$R_0$ herein is the same as $R_0$ in $X_1$ to $X_4$ of the aforementioned general formula (1). Furthermore, when $X_6$ is a nitrogen atom, $X_6$ may be bonded to $R_1$ for forming a ring structure, and when $X_7$ is a nitrogen atom, $X_7$ may be bonded to $R_2$ for forming a ring structure. In such cases, they may be bonded by a single bond or through a linking group.

Examples of the linking group include an alkylene group, an arylene group, an ester group, a carbonyl group, an ether group, an amino group, a thioether group, a sulfonic group, a sulfoxide group or a sulfide group and the like.

The alkylene group is not particularly limited, but preferably used is an alkylene group having 1 to 6 carbon atoms. Concrete examples thereof include a methylene group, an ethylene group, a propylene group, a butylene group and the like.

The arylene group is not particularly limited, but preferably used is an arylene group having 1 to 20 carbon atoms. Concrete examples thereof include a phenylene group, a naphthylene group, a phenanthrylene group, a biphenylyl group, a thienylene group, a pyridylene group, a pyrazylene group, a pyrimidylene group and the like. Furthermore, $R_1$ and $R_2$ in the compound represented by the general formula (3) will be explained. $R_1$ and $R_2$ each independently represent a hydrogen atom, a substituted or unsubstituted aryl group, a substituted or unsubstituted alkyl group, a substituted or unsubstituted cycloalkyl group, a substituted or unsubstituted aralkyl group and a group selected from the group consisting of the following general formula (4). (In the formula, $R_3$ represents a substituted or unsubstituted aryl group, a substituted or unsubstituted alkyl group, and a substituted or unsubstituted cycloalkyl group.)

(4)

The aryl group is not particularly limited, but examples thereof preferably include a substituted or unsubstituted carboncyclic aromatic group having 6 to 30 carbon atoms and a substituted or unsubstituted heterocyclic aromatic group having 3 to 25 carbon atoms, more preferably a substituted or unsubstituted carboncyclic aromatic group having 6 to 25 carbon atoms and a substituted or unsubstituted heterocyclic aromatic group having 4 to 12 carbon atoms, and further preferably a substituted or unsubstituted carboncyclic aromatic group having 6 to 22 carbon atoms and a substituted or unsubstituted heterocyclic aromatic group having 4 to 10 carbon atoms. Concrete examples include a phenyl group, a naphthyl group, an anthryl group, a biphenyl group, a thienyl group, a bithienyl group, a furyl group, a pyridyl group and the like.

The alkyl group is not particularly limited, but preferably used is a straight chain or branched alkyl group having 1 to 25 carbon atoms and preferably having 1 to 16 carbon atoms. Concrete examples thereof include a straight chain alkyl group such as a methyl group, an ethyl group, an n-propyl group, an n-butyl group, an n-pentyl group, an n-hexyl group, an n-heptyl group, an n-octyl group and a decyl group; and a branched alkyl group such as an i-propyl group, an s-butyl group, a t-butyl group, a methylpropyl group, a dimethylpropyl group, an ethylpropyl group, a diethylpropyl group, a methylbutyl group, a dimethylbutyl group, a methylpentyl group, a dimethylpentyl group, a methylhexyl group, a dimethylhexyl group and the like.

The cycloalkyl group is not particularly limited, but preferably used is a cycloalkyl group having 1 to 25 carbon atoms and preferably having 1 to 10 carbon atoms. Concrete examples thereof include a same type ring from cyclopropane to cyclodecane; and a groups having alkyl substituents such as methylcyclopentane, dimethylcyclopentane, methylcyclohexane, dimethylcyclohexane, trimethylcyclohexane, tetramethylcyclohexane, ethylcyclohexane, diethylcyclohexane and the like.

The aralkyl group is not particularly limited, but preferably used is an aralkyl group having 6 to 14 carbon atoms. Concrete examples thereof include a benzyl group, a 1-phenylethyl group, a 3-phenylpropyl group, a 4-phenylbutyl group, a 5-phenylpentyl group, a 6-phenylhexyl group, a benzhydryl group, a trityl group, a phenethyl group and the like.

Furthermore, $R_3$ in the general formula (4) represents a substituted or unsubstituted aryl group, a substituted or unsubstituted alkyl group, or a substituted or unsubstituted cycloalkyl group, but $R_3$ is the same as those described in $R_1$ and $R_2$ above.

Further, an aryl group, an alkyl group, a cycloalkyl group and an aralkyl group corresponding to $R_1$ and $R_2$ may have a substituent. Concrete examples of the substituent include an alkyl group, an alkoxy group, an alkylthio group, a hydroxyalkyl group, an alkoxyalkyl group, a monoalkylaminoalkyl group, a dialkylaminoalkyl group, a halogenated alkyl group, an alkoxycarbonylalkyl group, a carboxyalkyl group, an alkanoyloxyalkyl group, an aminoalkyl group, a halogen atom, an amino group, a hydroxy group, a carboxyl group which may be esterified, a cyano group and the like. Incidentally, the substitution position of these substituents is not particularly limited.

As the alkyl group, preferably used is an alkyl group which may have a substituent having 1 to 10 carbon atoms. Concrete examples thereof include a straight chain alkyl group such as a methyl group, an ethyl group, an n-propyl group and an n-butyl group; and a branched alkyl group such as an i-propyl group, an s-butyl group and a t-butyl group.

As the alkoxy group, preferably used is an alkoxy group which may have a substituent having 1 to 10 carbon atoms. Concrete examples thereof include a methoxy group, an ethoxy group, a propoxy group, an isopropoxy group and the like.

As the alkylthio group, preferably used is an alkylthio group which may have a substituent having 1 to 10 carbon atoms. Concrete examples thereof include a methylthio group, an ethylthio group, a propylthio group, an isopropyl thio group and the like.

The hydroxyalkyl group has a structure wherein a hydroxyl group is substituted at an alkyl group, and preferably used is a hydroxyalkyl group having 1 to 20 carbon atoms and more preferably used is a hydroxyalkyl group having 1 to 10 carbon atoms. Concrete examples thereof include a hydroxymethyl group, a hydroxyethyl group, a hydroxypropyl group, a hydroxybutyl group, a 2-hydroxyethyl group and the like.

The alkoxyalkyl group has a structure wherein an alkoxyl group is substituted at an alkyl group, and preferably used is an alkoxyalkyl group having 1 to 20 carbon atoms and more preferably used is an alkoxyalkyl group having 1 to 10 carbon atoms. Concrete examples thereof include a methoxymethyl group, an ethoxymethyl group, a butoxymethyl group, an ethoxyethyl group, a butoxyethyl group, a 2-methoxyethyl group and the like. The substitution position of the alkoxyl group on the alkyl group is not particularly limited, and the alkoxyl group may be on any of carbon atoms of alkyl chains, for example, in the middle, at the end or the like of the alkyl group.

The monoalkylaminoalkyl group has a structure wherein one alkyl group having 1 to 10 carbon atoms is substituted on a nitrogen atom of an aminoalkyl group having 1 to 10 carbon atoms. Concrete examples thereof include an N-methylaminomethyl group, an N-methylaminoethyl group, an N-propyl aminopropyl group and the like.

The dialkylaminoalkyl group has a structure wherein two alkyl groups having 1 to 10 carbon atoms are substituted on a nitrogen atom of an aminoalkyl group having 1 to 10 carbon atoms. Concrete examples thereof include an N,N-dimethylaminomethyl group, an N-ethyl-N-methylaminoethyl group, an N,N-dipropylaminopropyl group and the like.

The halogenated alkyl group has a structure wherein a halogen atom is substituted at an alkyl group, and preferably used is a halogenated alkyl group having 1 to 20 carbon atoms and more preferably used is a halogenated alkyl group having 1 to 10 carbon atoms. Concrete examples thereof include a trifluoromethyl group, a 2,2,2-trifluoroethyl group, a 2-fluoroethyl group, a 2-chloroethyl group and the like. The halogen atom may be selected from any of a fluorine atom, a chlorine atom, a bromine atom and an iodine atom, but preferably used are a fluorine atom and a chlorine atom. The number of halogen atoms is not particularly limited, but it is 1 or more. For example, all hydrogen atoms may be substituted with halogen atoms like perfluoro derivatives.

As the alkoxycarbonylalkyl group, preferably used is an alkoxycarbonylalkyl group having 1 to 20 carbon atoms and more preferably used is an alkoxycarbonylalkyl group having 1 to 10 carbon atoms. Concrete examples thereof include a methoxycarbonylmethyl group, an ethoxycarbonylmethyl group, an n-propoxycarbonylmethyl group, an n-butoxycarbonylmethyl group, a methoxycarbonylethyl group, a methoxycarbonylpropyl group and the like.

The carboxyalkyl group has a structure wherein a carboxyl group is substituted at an alkyl group, and preferably used is a carboxyalkyl group having 1 to 20 carbon atoms and more preferably used is a carboxyalkyl group having 1 to 10 carbon atoms. Concrete examples thereof include a carboxymethyl group, a 2-carboxyethyl group and the like.

As the alkanoyloxyalkyl group, preferably used is an alkanoyloxyalkyl group having 1 to 20 carbon atoms and more preferably used is an alkanoyloxyalkyl group having 1 to 10 carbon atoms. Concrete examples thereof include an acetoxymethyl group, a propionyloxymethyl group, a butyryloxymethyl group, an isobutyryloxymethyl group, a 1-acetoxyethyl group and the like.

The aminoalkyl group has a structure wherein an amino group is substituted at an alkyl group, and preferably used is an aminoalkyl group having 1 to 20 carbon atoms, and more preferably used is an aminoalkyl group having 1 to 10 carbon atoms. Concrete examples thereof include an aminomethyl group, an aminoethyl group, an aminopropyl group and the like.

Examples of the halogen atom include a fluorine atom, a chlorine atom, a bromine atom and an iodine atom. Preferably used are a fluorine atom and a chlorine atom. Concrete examples of the compound represented by the above general formula (1) are hereinafter mentioned, though not limited to these compounds.

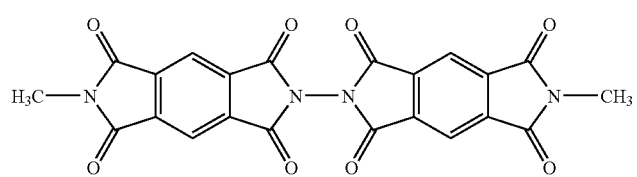

(1)

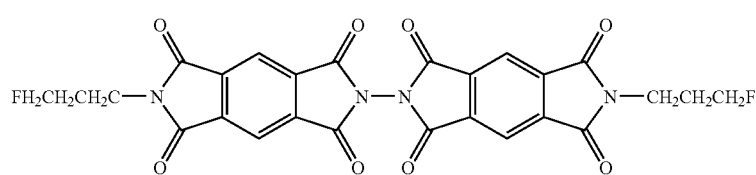

(2)

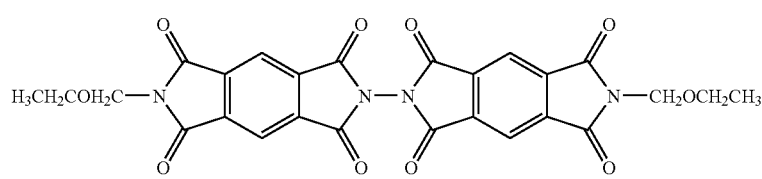

(3)

-continued
(4)
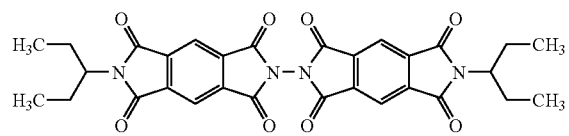
(5)
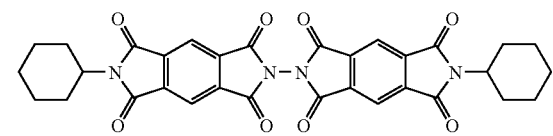
(6)
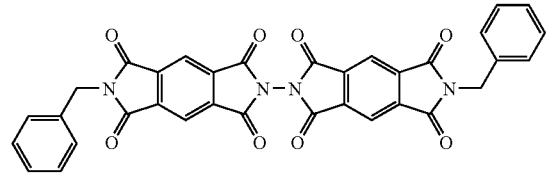
(7)
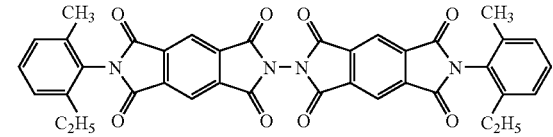
(8)
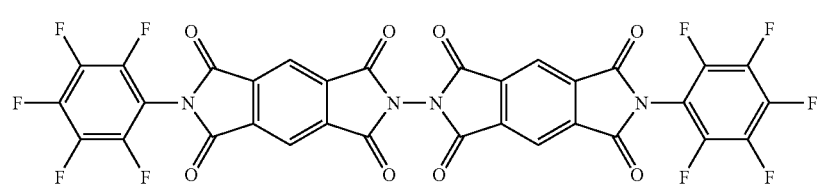
(9)
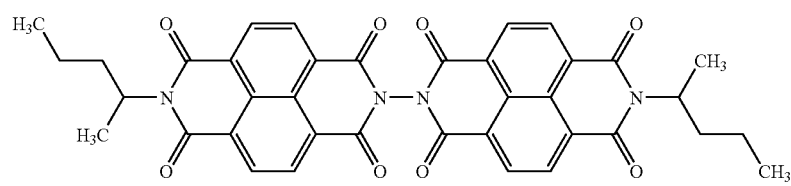
(10)
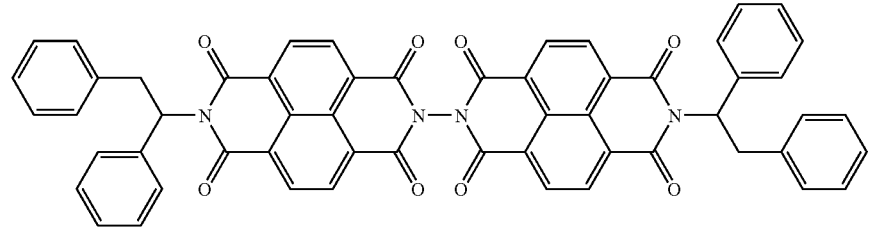
(11)
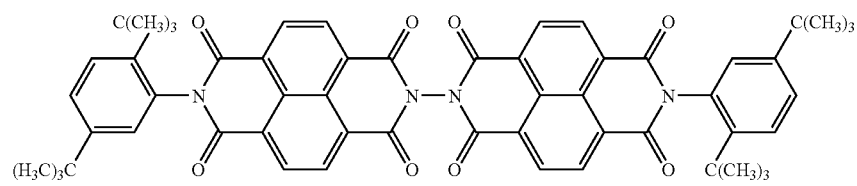
(12)
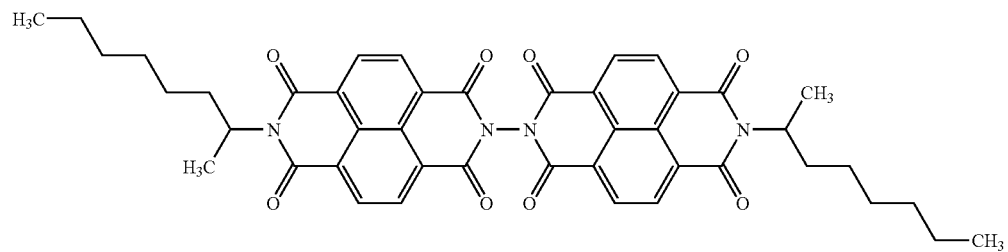
(13)
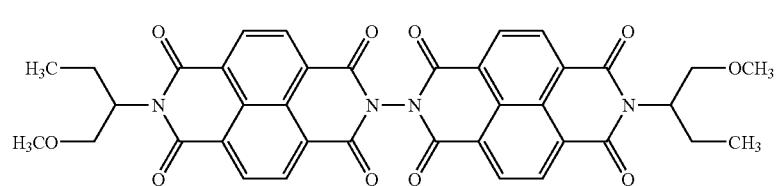

-continued
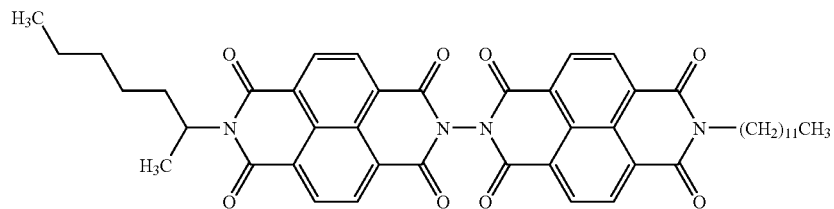
(14)
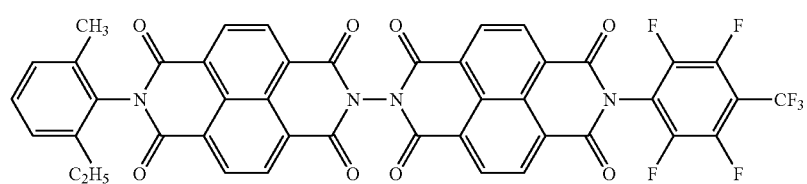
(15)
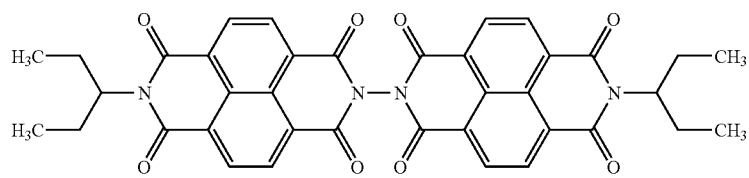
(16)
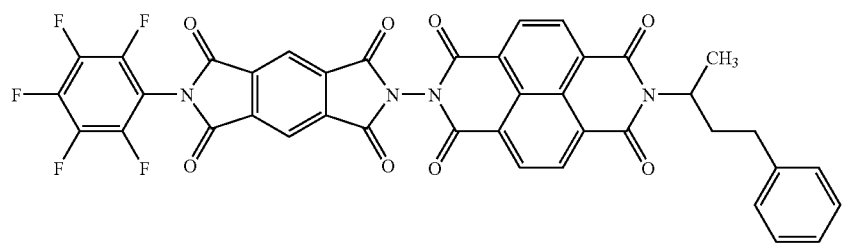
(17)
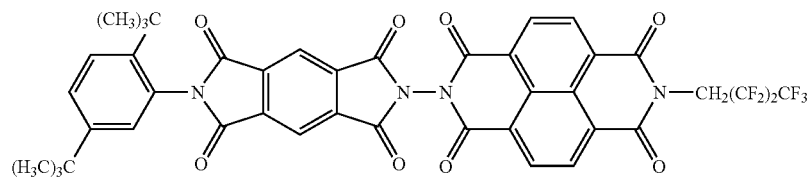
(18)
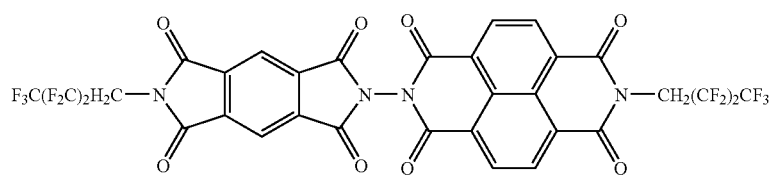
(19)
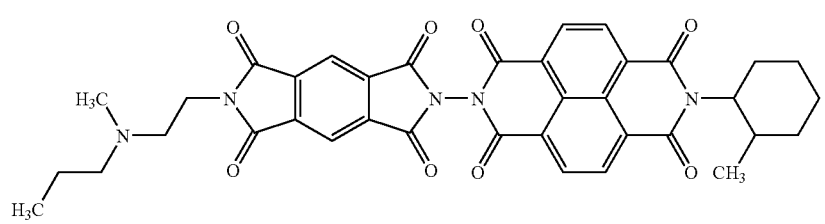
(20)
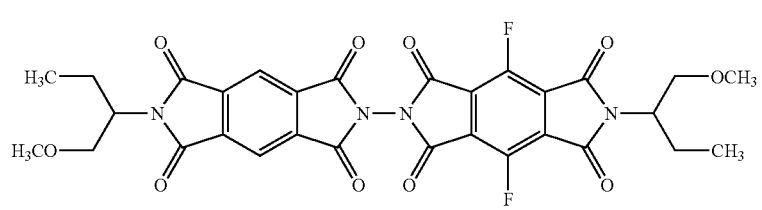
(21)

-continued
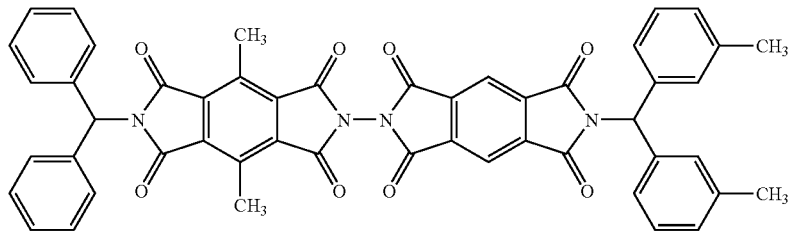
(22)
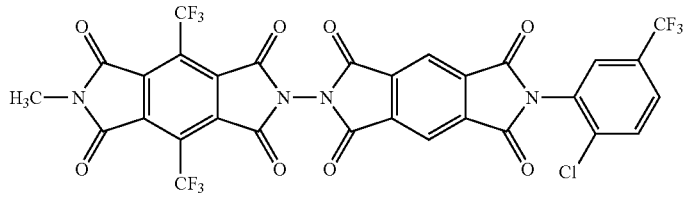
(23)
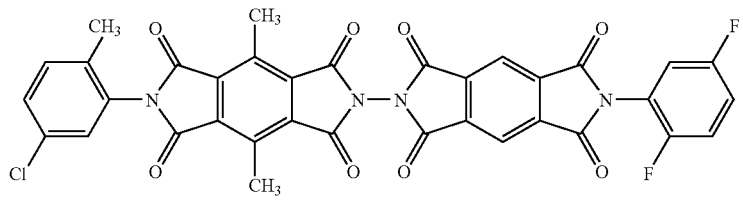
(24)
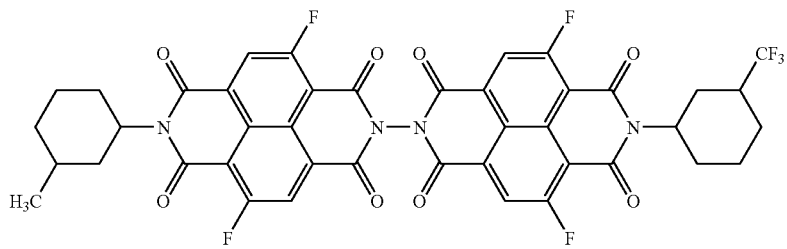
(25)
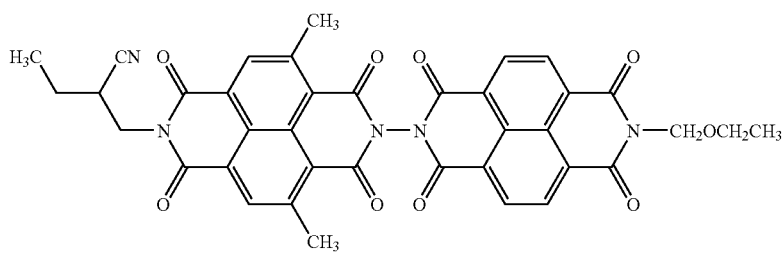
(26)
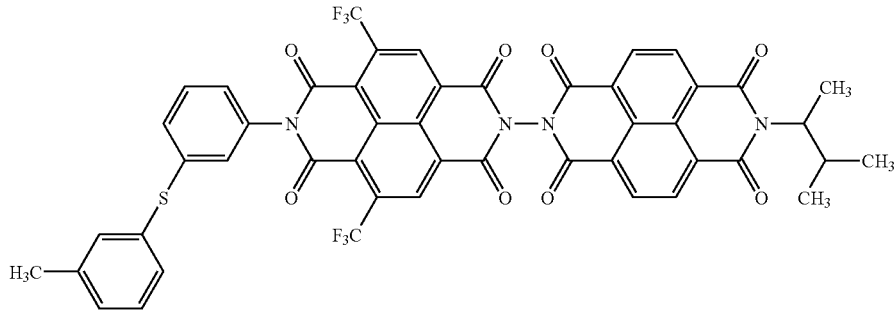
(27)

-continued
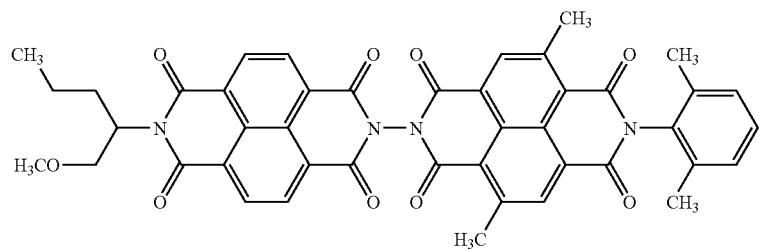
(28)
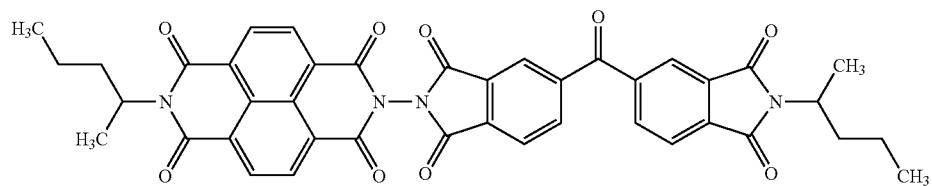
(29)
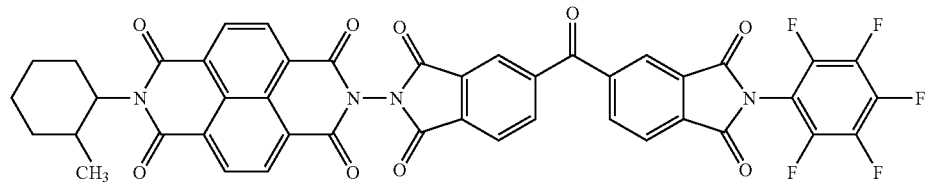
(30)
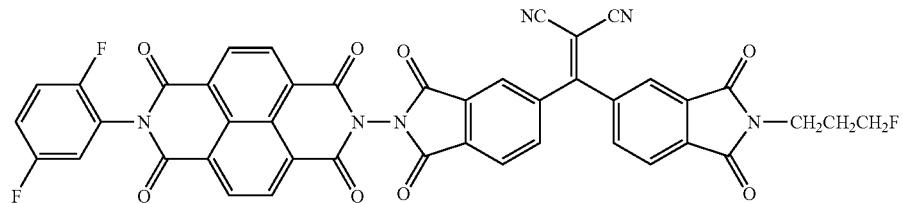
(31)
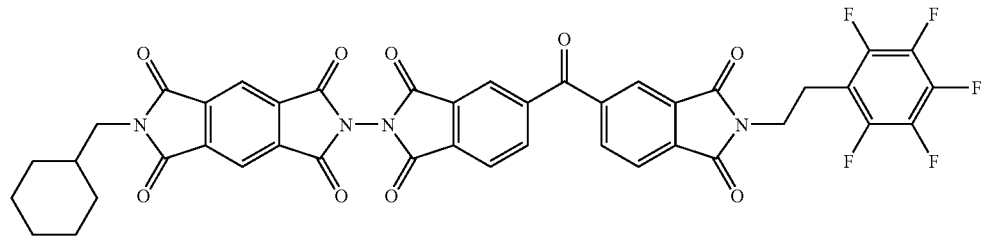
(32)
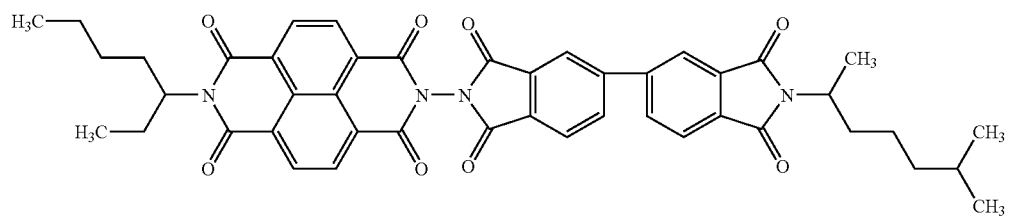
(33)
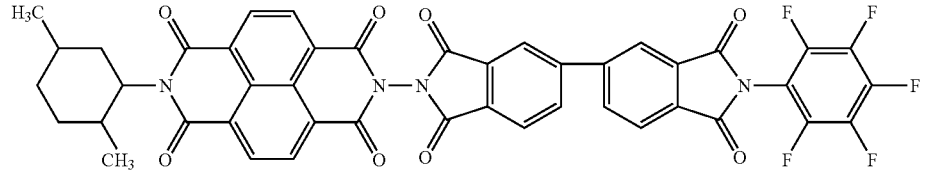
(34)

-continued
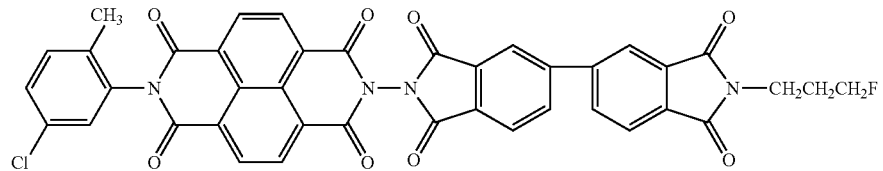 (35)
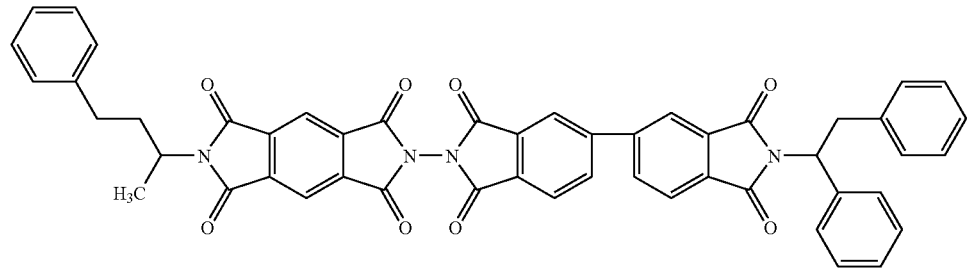 (36)
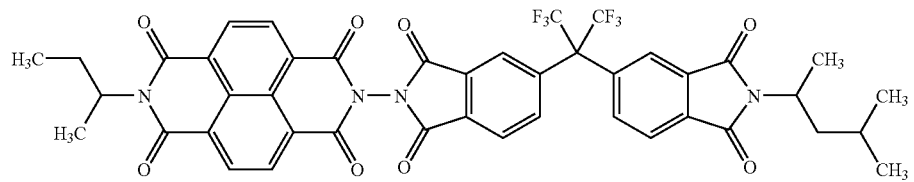 (37)
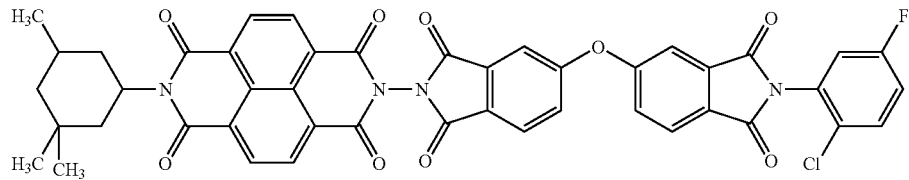 (38)
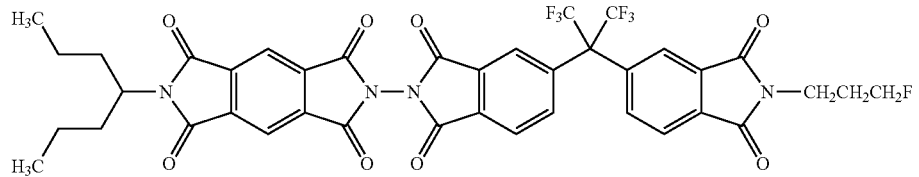 (39)
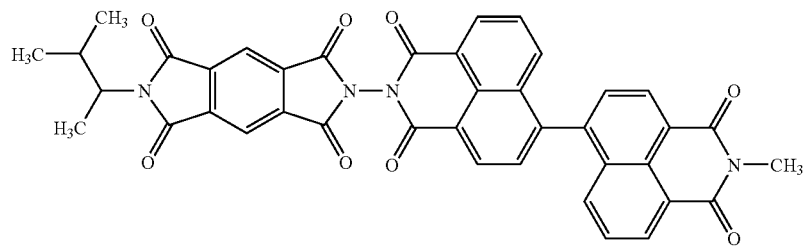 (40)
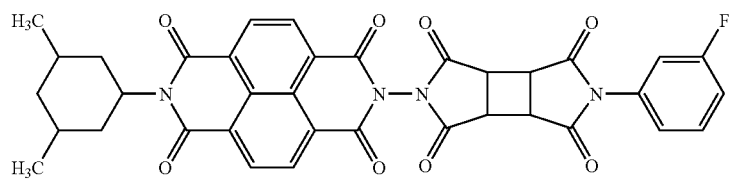 (41)

-continued
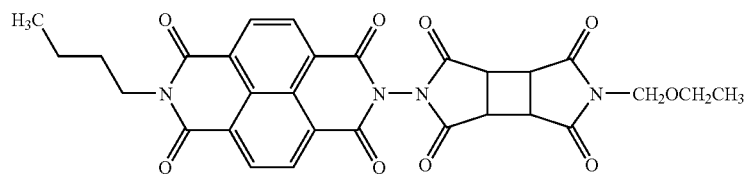
(42)
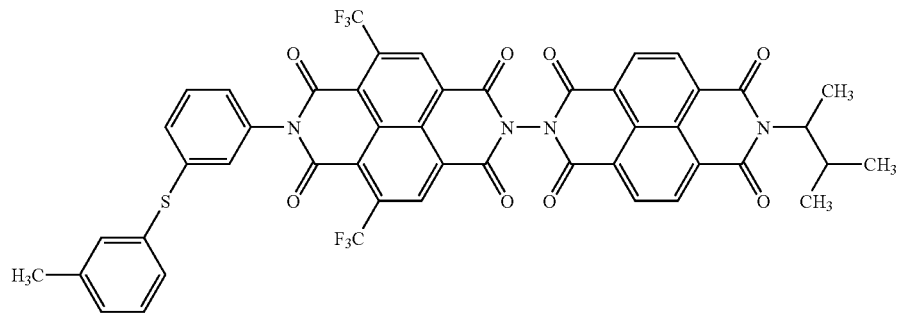
(43)
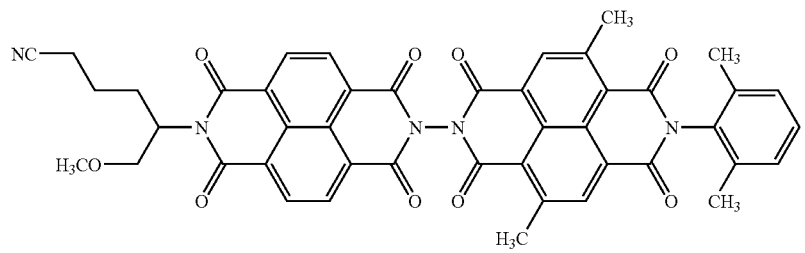
(44)
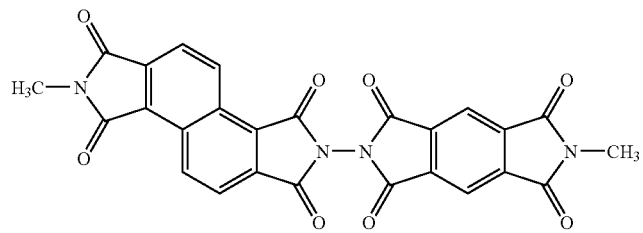
(45)
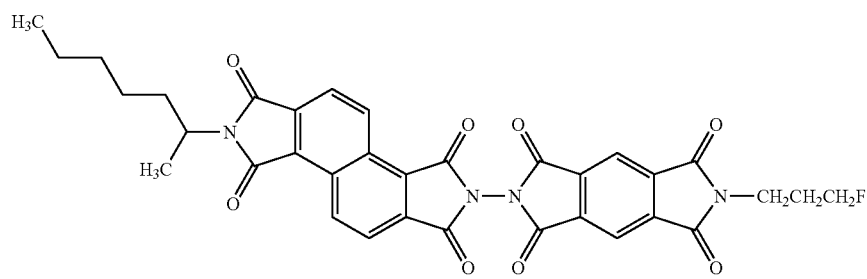
(46)
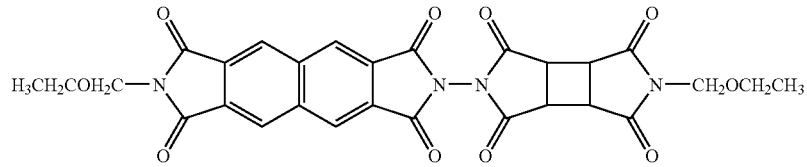
(47)
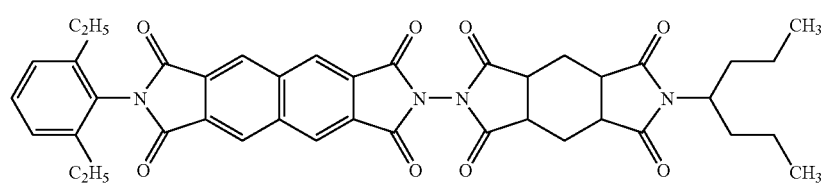
(48)

-continued
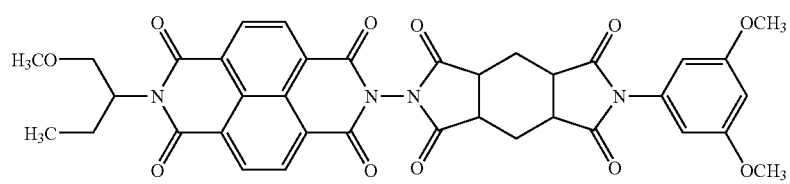
(49)
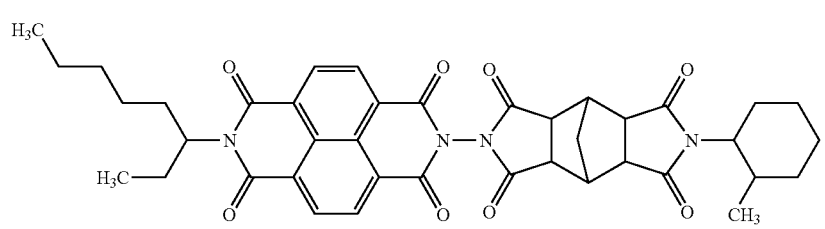
(50)
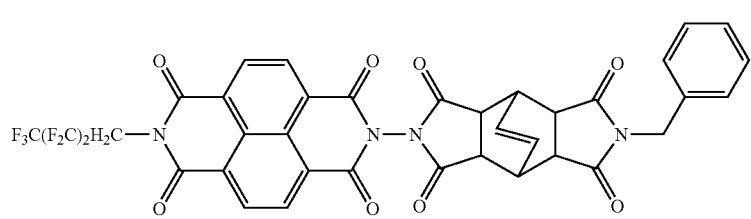
(51)
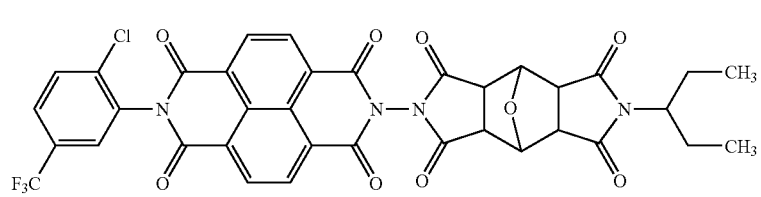
(52)
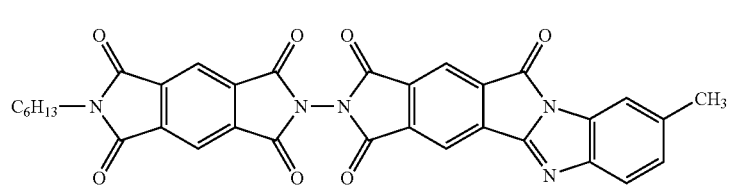
(53)
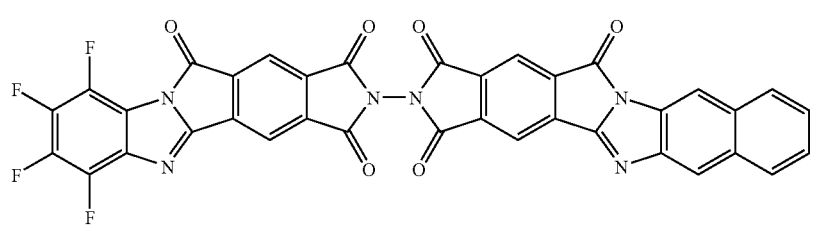
(54)
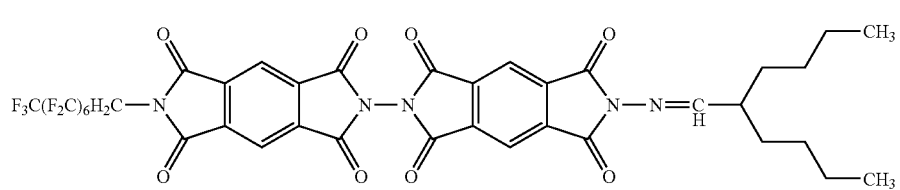
(55)
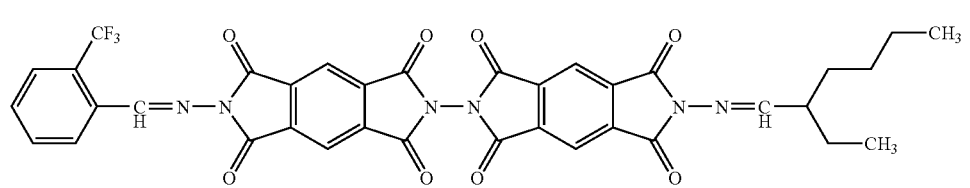
(56)

-continued
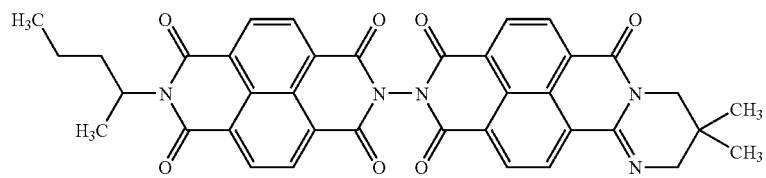
(57)
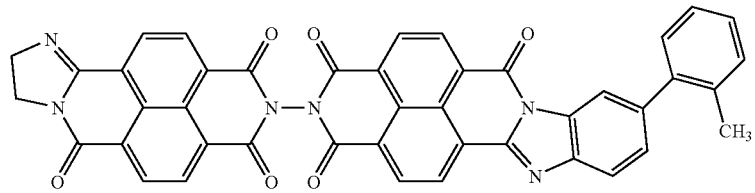
(58)
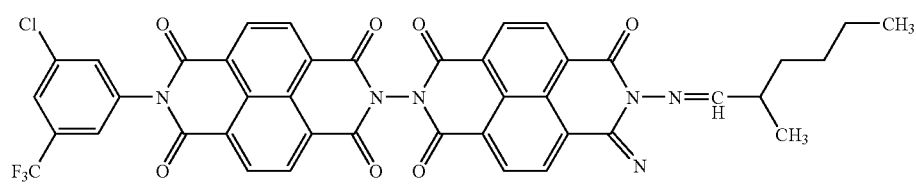
(59)
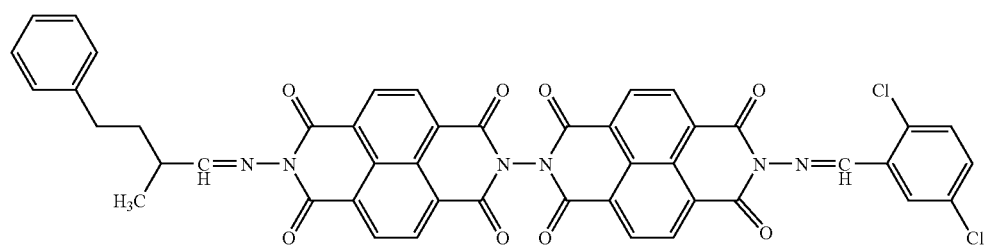
(60)
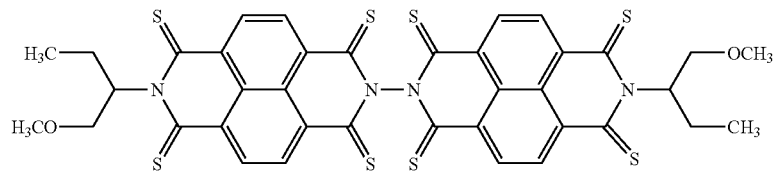
(61)
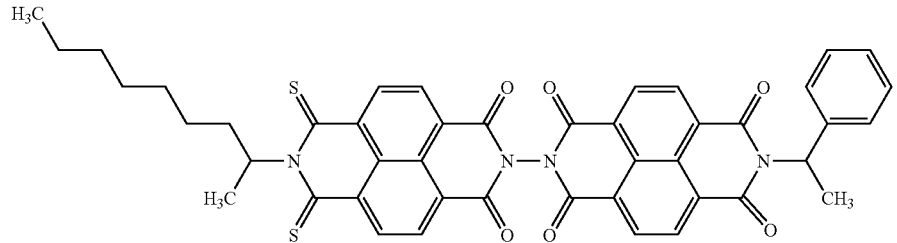
(62)
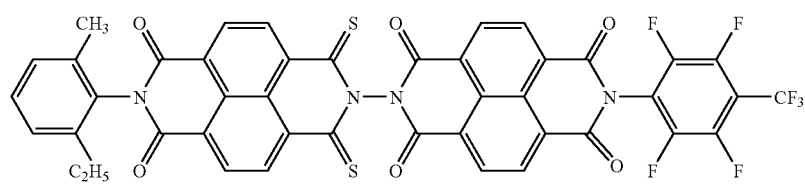
(63)
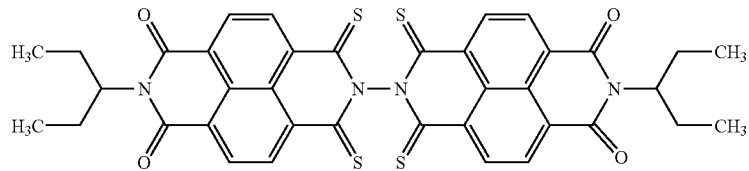
(64)

-continued
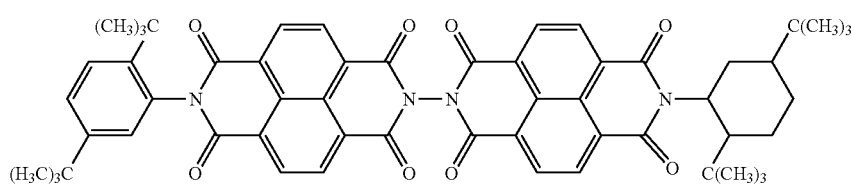
(65)
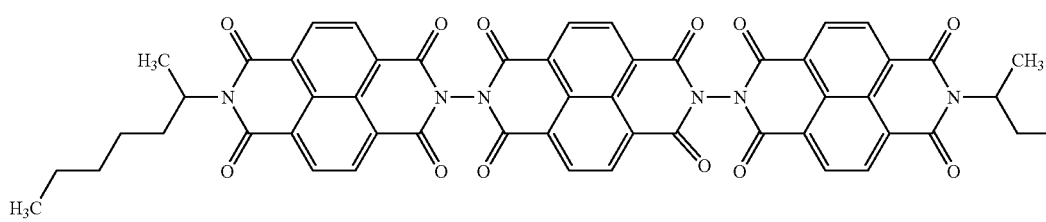
(66)
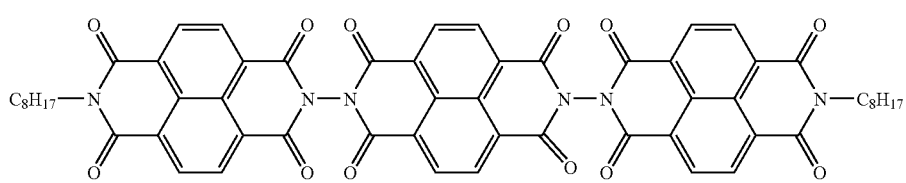
(67)
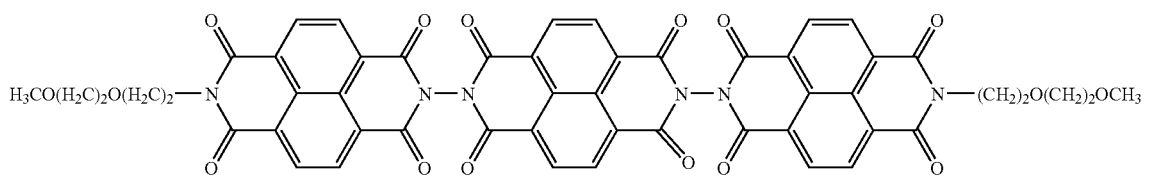
(68)
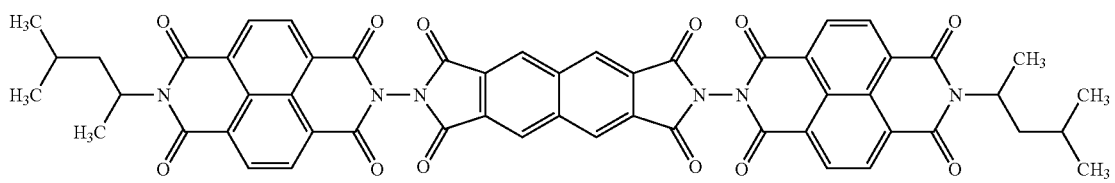
(69)
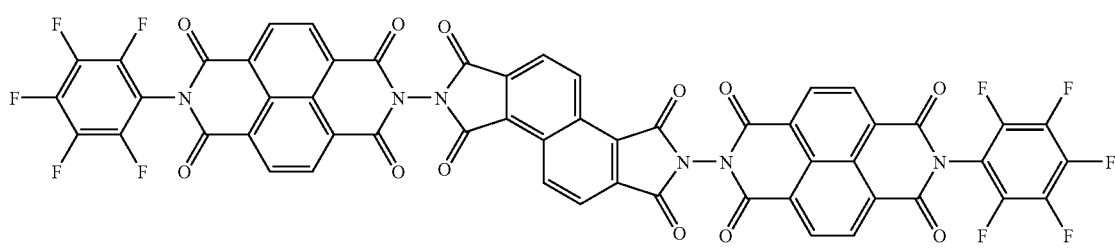
(70)
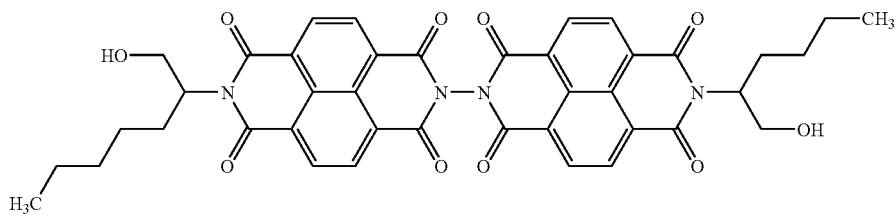
(71)
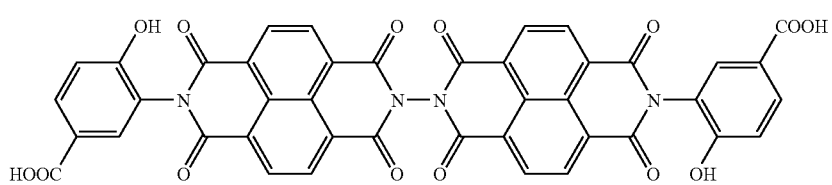
(72)

Production methods of the novel compound of the present invention, more specifically, the compound represented by the general formula (3) will be described hereinafter. The synthesis method of the tetracarboxylic acid derivative represented by the general formula (3) is not particularly limited, but the tetracarboxylic acid derivative is synthesized as in, for example, the following reaction formulae (schemes 1 and 2) according to known synthesis methods (for example, Japanese Patent Laid-Open No. 2001-265031, J. Am. Chem. Soc., 120, 3231 (1998), J. Tetrahedron Letters, 42, 3559 (2001), Japanese Patent Laid-Open No. 1975-69674 or the like). Namely, when naphthalene is selected as an aryl moiety, a method of preparing monoimide derivatives by reacting a naphthalene carboxylic acid or its anhydride with amines, a method of reacting a naphthalene carboxylic acid or its anhydride with amines by adjusting PH of a naphthalene carboxylic acid or its anhydride using a buffering agent or the like is used.

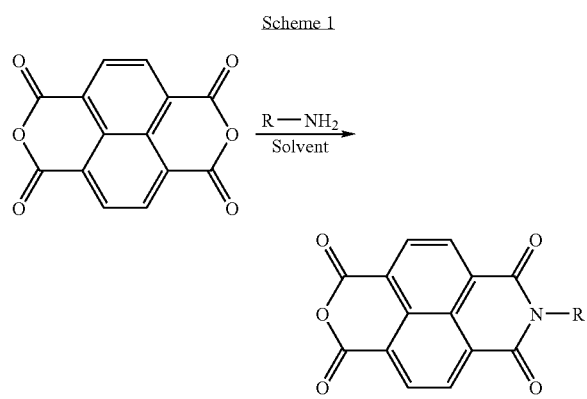

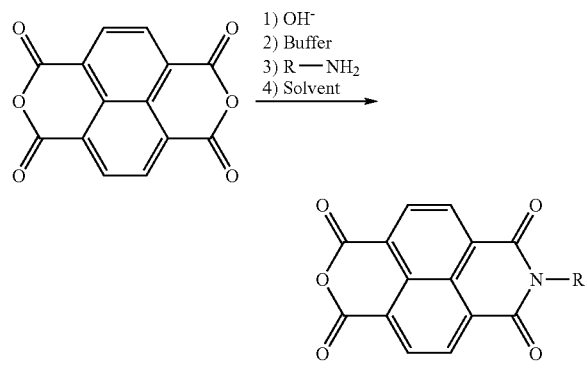

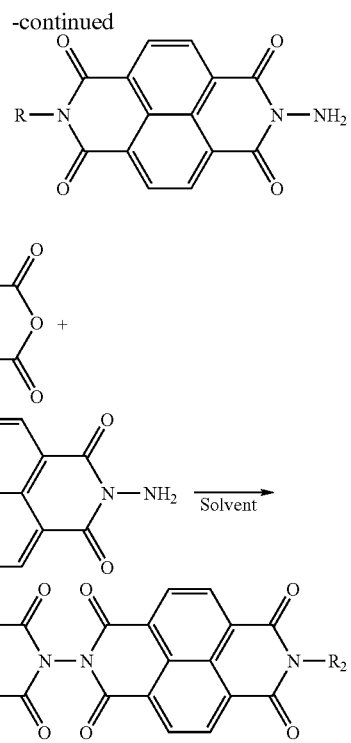

Preparing monoimide derivatives is carried out without a solvent or in the presence of a solvent. Examples of the solvent include benzene, toluene, xylene, chloronaphthalene, acetic acid, pyridine, picoline, dimethylformamide, dimethylacetamide, dimethylethylene urea, dimethyl sulfoxide and the like. Such solvents that do not react with a raw material or a reactant and are reacted at a temperature of from 50° C. to 250° C. are used.

To adjust pH, a buffering agent prepared by mixing a basic aqueous solution such as lithium hydroxide, sodium hydroxide, potassium hydroxide and the like with an acid such as a phosphoric acid and the like is used.

A synthesis method for a N-amine derivative from a monoimide arylcarboxylic acid derivative is not particularly limited, but the synthesis can be carried out by known synthesis methods (for example, J. Am. Chem. Soc., 118, 81 (1996) and the like). Preparing N-amine derivatives is carried out without a solvent or in the presence of a solvent. Examples of the solvent include benzene, toluene, xylene, chloronaphthalene, acetic acid, pyridine, picoline, dimethylformamide, dimethylacetamide, dimethylethylene urea, dimethyl sulfoxide and the like. Such solvents that do not react with a raw material or a reactant and are reacted at a temperature of from 50° C. to 250° C. are used.

The dehydration reaction of a monoimidized carboxylic acid derivative with an N-aminated carboxylic acid derivative is carried out without a solvent or in the presence of a solvent. Examples of the solvent include benzene, toluene, xylene, chloronaphthalene, bromonaphthalene, acetic anhydride and the like. Such solvents that do not react with a raw material or a reactant and are reacted at a temperature of from 50° C. to 250° C. are used.

Any reaction may be carried out without a catalyst or in the presence of a catalyst and is not particularly limited. For example, a molecular sieve, a benzene sulfonic acid, a p-toluene sulfonic acid or the like can be used as a dehydrating agent.

Embodiments of the organic electrophotographic photoconductor of the present invention will be explained with reference to the drawings. FIG. 1 is a schematic view illustrating an example of the photoconductor according to the present invention. In FIG. 1, 10 refers to a conductive substrate, 20 refers to an under coat layer, 30 refers to a photosensitive layer, and 40 refers to a protecting layer. The under coat layer 20 and the protecting layer 40 are provided depending on the intended use. The photosensitive layer 30 combines the charge generation function and charge transport function, which includes a single-layered type having one layer serving both functions or a dual-layered type having two separate layers of a charge generation layer and a charge transport layer.

The electrophotographic photoconductor of the present invention can be applied to any of the single-layered type and the dual-layered type, whereas the effect resulting from the use of the novel compound (1) of the present invention is remarkably exhibited in the single-layered photoconductor. The single-layered photoconductor is provided with at least a single photosensitive layer comprising the novel compound (1) as an electron transporting agent, a charge generating agent and a polymeric binder on the conductive substrate. This photosensitive layer of the single-layered type can correspond to any of positive charging and negative charging with a single structure, but positive charging which does not need to employ negative charged corona discharge is preferably used. The single-layered photoconductor has advantages in that productivity is excellent due to a simple layer structure, defects in a coated film of the photosensitive layer can be prevented, and optical properties can be improved because of a small interlayer interface.

On the other hand, the dual-layered type photoconductor is a layered product of a charge generation layer containing a charge generating agent and a charge transport layer containing a charge transporting agent on the conductive base in the successive order or in the reverse order. However, a film thickness of the charge generation layer is very thin as compared to that of the charge transport layer. So, in order to protect the layer, it is preferable to form a charge generation layer on the conductive base on which a charge transport layer is then formed.

The conductive substrate 10 serves as an electrode for the photoconductor and at the same time comprises a supporting body of other respective layers, and may have any shape of a cylinder, a plate or a film. As materials, there can be mentioned, for example, a simple metal such as iron, aluminum, copper, tin, platinum, stainless steel, nickel and the like, plastic materials subjected to conductive treatment with the above metal subjected to deposition or lamination, or glass coated with aluminum iodide, tin oxide, indium oxide or the like.

The under coat layer 20 can be placed depending on the intended use and comprises a layer having a polymer as a main component or an oxide film such as alumite and the like, which is placed as needed for the purposes of prevention of undesired charge injection into the photosensitive layer from the conductive substrate, coating of defects on the base surface, improved adhesion of the photosensitive layer or the like. Examples of the polymeric binder for the under coat layer include polycarbonate (PC), polyester, polyvinyl poly(vinyl acetal), poly(vinyl butyral), poly(vinyl chloride), poly(vinyl acetate), polyethylene, polypropylene, polystyrene, an acrylic resin, polyurethane, an epoxy resin, a melamine resin, a silicone resin, polyamide, polyacetal, polyarylate, polysulfone, polymers of methacrylate, copolymers of methacrylate and the like. These compounds can be properly used in combination thereof. Further, the polymeric binder may contain metal oxides such as silicone oxide(silica), titanium oxide, zinc oxide, calcium oxide, aluminum oxide(alumina), zirconium oxide and the like; metal sulfides such as barium sulfide, calcium sulfide and the like; metal nitrides such as silicon nitride, aluminum nitride and the like; metal oxide particles or the like.

The film thickness of the under coat layer is different depending on the combined composition of the under coat layer, but can be arbitrarily set in the ranges in which bad influence such as an increase of residual potential may not be exerted when used repeatedly and continuously.

The photosensitive layer 30 is mainly composed of two layers such as a charge generation layer and a charge transport layer in case it is a dual-layered type, while it is composed of one layer in case it is a single-layered type. The charge generation layer is formed by vacuum deposition of an organic photoconductive substance or by coating a material containing particles of an organic photoconductive substance dispersed in a polymeric binder, which serves to receive light and generate charges. Further, it is important to have high charge generation efficiency and at the same time injecting properties of the generated charges to the charge transport layer. It is preferable to achieve good injection even under low electric field because dependency on the electric field is low.

The charge generation layer comprises a charge generating agent as a main component, and, in addition thereto, a charge transporting agent or the like can be added. As the charge generating agent, there can be used, for example, phthalocyanine pigments, azo pigments, anthantrone pigments, perylene pigments, perynone pigments, squarylium pigments, thiapyrylium pigments, quinacridone pigments or the like. Further, these pigments may be used in combination thereof. In particular, as azo pigments, preferably used are bisazo pigments and trisazo pigments, as perylene pigments, preferably used is N,N'-bis(3,5-dimethylphenyl)-3,4:9,10-perylene bis(carboxyimide), and as phthalocyanine pigments, preferably used are metal-free phthalocyanine, copper phthalocyanine and titanyl phthalocyanine, and more preferably used are X-type metal-free phthalocyanine, τ-type metal-free phthalocyanine, ε-type copper phthalocyanine, α-type titanyl phthalocyanine, β-type titanyl phthalocyanine, Y-type titanyl phthalocyanine and amorphous titanyl phthalocyanine.

Furthermore, the above-exemplified charge generating agents are used singly or in combination of two or more kinds, in order to have an absorption wavelength at the desired region. In the above-exemplified charge generating agents, in particular, a digital optical image recording device such as a laser beam printer, facsimile or the like using a light source including a semiconductor laser requires a photoconductor having a sensitivity at a wavelength region of not less than 700 nm. So, for example, phthalocyanine pigments such as metal-free phthalocyanine, titanyl phthalocyanine or the like are suitably used.

On the other hand, since an analog optical image recording device such as an electrostatic copier or the like using a white light source including a halogen lamp and the like requires a photoconductor having a sensitivity at a visible region, perylene pigments, bisazo pigments or the like are suitably used.

As the polymeric binder for the charge generation layer, various polymeric binders that have been used for a photosensitive layer from the past can be used. Examples thereof include poly(vinyl acetal), poly(vinyl butyral), poly(vinyl chloride), poly(vinyl acetate), a silicone resin, polycarbonate (PC), polyester, polyethylene, polypropylene, polystyrene, an acrylic resin, polyurethane, an epoxy resin, a melamine resin, polyamide, polyacetal, polyarylate, polysulfone, polymers of methacrylate, copolymers of methacrylate and the like. These polymeric binders can be suitably used in combination thereof.

The electron transport layer refers to a film comprising a material with a charge transporting agent dispersed in a polymeric binder, and exerts the function of maintaining charges of a photoconductor as an insulator layer at a dark place and the function of transporting charges injected from the charge generation layer at the time of receiving light.

As the charge transporting agent, there can be used, for example, a hole transporting agent such as a hydrazone compound, a pyrazoline compound, a pyrazolone compound, an oxadiazole compound, an oxazole compound, an arylamine compound, a benzidine compound, a stilbene compound, a styryl compound, polyvinylcarbazole, polysilane and the like; or an electron transporting agent such as succinic anhydride, maleic anhydride, dibromosuccinic anhydride, phthalic anhydride, 3-nitrophthalic anhydride, 4-nitrophthalic anhydride, pyromellitic anhydride, pyromellitic acid, trimellitic acid, trimellitic anhydride, phthalimide, 4-nitrophthalimide, tetracyanoethylene, tetracyanoquinodimethane, chloranil, bromanil, o-nitrobenzoic acid, trinitrofluorenone, quinone, diphenoquinone, naphthoquinone, anthraquinone, stilbenequinone and the like. For example, compounds of structural formulae represented by the following structural formulae (A-1) to (A-15) are used, but the compounds are not limited thereto.

(A-1)
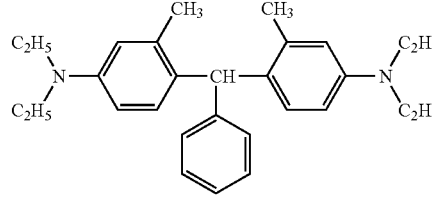

(A-2)
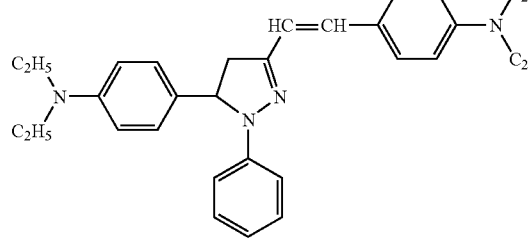

(A-3)
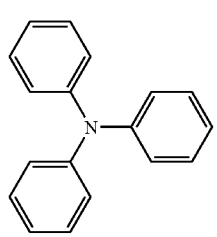

-continued (A-4)
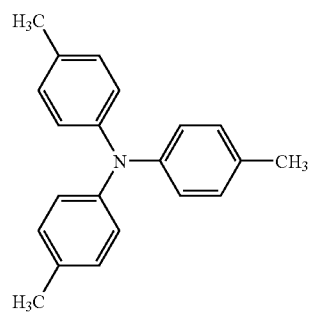

(A-5)
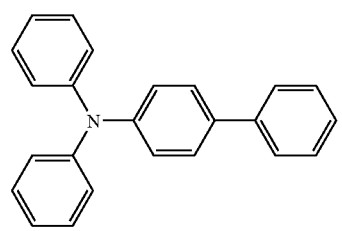

(A-6)
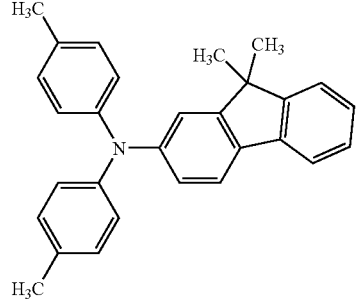

(A-7)
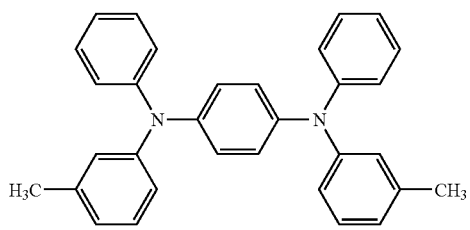

(A-8)
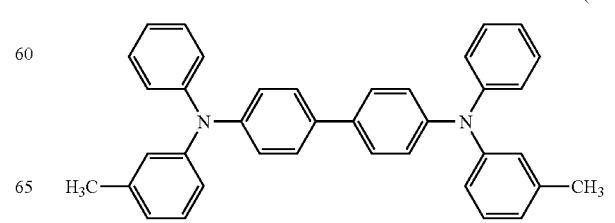

-continued

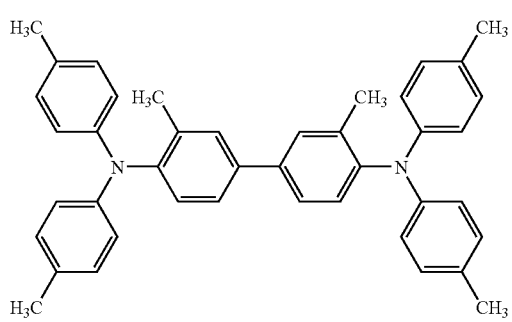
(A-9)

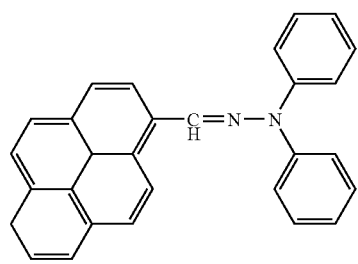
(A-10)

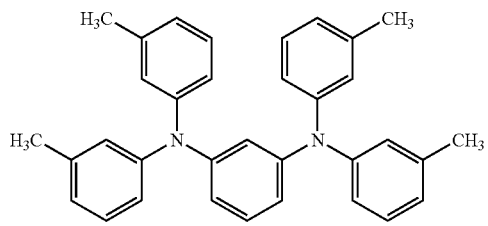
(A-11)

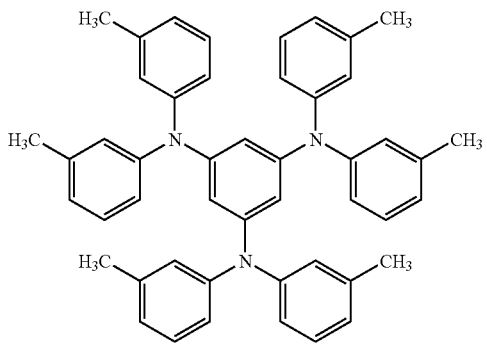
(A12)

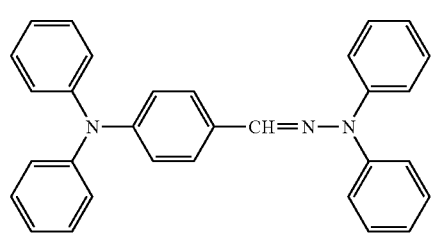
(A13)

-continued

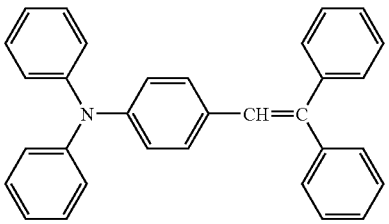
(A-14)

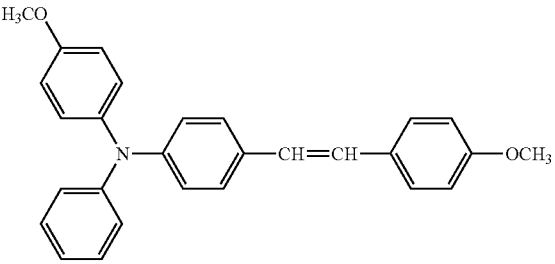
(A-15)

As the polymeric binder for the charge transport layer, various polymeric binders that have been used for a photosensitive layer from the past can be used. Examples thereof include polycarbonate (PC), polyester, poly(vinyl acetal), poly(vinyl butyral), poly(vinyl chloride), poly(vinyl acetate), polyethylene, polypropylene, polystyrene, an acrylic resin, polyurethane, an epoxy resin, a melamine resin, a silicone resin, polyamide, polyacetal, polyarylate, polysulfone, polymers of methacrylate, copolymers of methacrylate and the like. It is possible to use these polymeric binders suitably in combination thereof. In particular, suitably used are polycarbonate resins or polyester resins comprising one or two or more kinds of the following structural units (B-1) to (B-3).

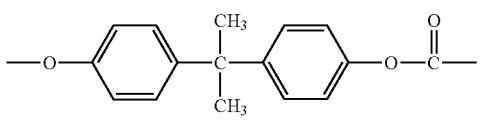
(B-1)

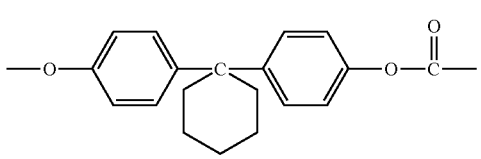
(B-2)

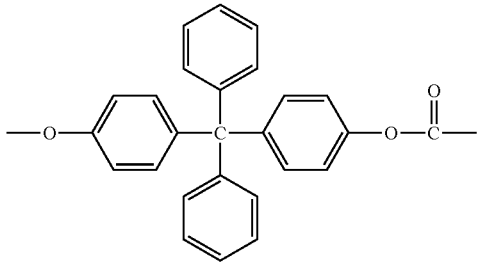
(B-3)

In these photosensitive layers, various known additives can also be contained, in addition to the above respective components, in the ranges in which electrophotographic properties are not adversely affected. Concretely, degradation inhibitors such as antioxidants, radical trapping agents, singlet quenchers, UV absorbers and the like, softening agents, plasticizers, surface modifiers, dispersion stabilizers, waxes, acceptors, donors and the like can be combined. Further, in order to improve a sensitivity of the photosensitive layer, for example, known sensitizers such as terephenyl, halonaphthoquinones, acenaphthylene and the like may be used together with the charge generating agent.

The protecting layer 40 can be placed as needed for the purposes of enhancing the printing durability and the like, and comprises a layer having a polymeric binder as a main component or an inorganic thin film such as amorphous carbon or the like. Further, the polymeric binder may contain metal oxides such as silicone oxide(silica), titanium oxide, zinc oxide, calcium oxide, aluminum oxide(alumina), zirconium oxide and the like; metal sulfides such as barium sulfide, calcium sulfide and the like; metal nitrides such as silicon nitride, aluminum nitride and the like; metal oxide particles; fluorine type resin particles such as a tetrafluoroethylene resin and the like; a fluorine type comb-shaped graft polymerization resin or the like, for the purposes of increased conductivity, reduced friction coefficient, giving of smoothness and the like. Furthermore, for the purpose of giving the ability of electron transport, an electron transporting substance, an electron accepting substance used for the above photosensitive layer or the novel compound of the present invention may also be contained.

Next, a method of producing the electrophotographic photoconductor of the present invention will be explained. The single-layered photoconductor according to the present invention is formed by properly dissolving or dispersing the novel compound represented by the general formula (1) (electron transporting material), a charge generating material, a polymeric binder, and a hole transporting material as needed for obtaining a coating solution, applying the coating solution on the conductive base, and drying the resultant.

The charge generating material in the above single-layered photoconductor may be combined in a ratio of from 0.01 to 50 weight parts, and preferably from 0.1 to 30 weight parts, based on 100 weight parts of the polymeric binder. The electron transporting material may be combined in a ratio of from 5 to 150 weight parts, and preferably from 10 to 100 weight parts, based on 100 weight parts of the polymeric binder. The hole transporting material may be combined in a ratio of from 5 to 500 weight parts, and preferably from 25 to 200 weight parts, based on 100 weight parts of the polymeric binder. Further, when the electron transporting material and hole transporting material are used together, the total amount of the electron transporting material and hole transporting material may be properly from 20 to 500 weight parts, and preferably from 30 to 200 weight parts, based on 100 weight parts of the polymeric binder.

The film thickness of the photosensitive layer in the single-layered photoconductor is preferably in the range of 5 to 80 μm and more preferably from 10 to 50 μm, in order to practically maintain effective surface potential.

The dual-layered type photoconductor in the present invention is produced by forming a charge generation layer containing a charge generating material on the conductive base by means of vapor deposition, coating or the like, applying a coating solution comprising the novel compound represented by the general formula (1) (electron transporting material) and the polymeric binder on this charge generation layer, and drying the resultant for forming a charge transport layer.

In the above dual-layered type photoconductor, the charge generating material and the polymeric binder constituting the charge generation layer can be used in various proportions, but the charge generating material is properly combined in a ratio of from 5 to 1,000 weight parts and preferably from 30 to 500 weight parts, based on 100 weight parts of the polymeric binder. When the hole transporting material is contained in the charge generation layer, the proportion of the hole transporting material is properly from 10 to 500 weight parts and preferably from 50 to 200 weight parts, based on 100 weight parts of the polymeric binder.

The electron transporting material and the polymeric binder constituting the charge transport layer can be used in various proportions in the ranges in which transfer of charges is not prevented and they are not crystallized. However, in order to easily transport charges generated at the charge generation layer by light irradiation, the electron transporting material is properly combined in a ratio of from 10 to 500 weight parts and preferably from 25 to 200 weight parts, based on 100 weight parts of the polymeric binder. When other electron transporting material having a prescribed oxidation reduction potential is contained in the charge transport layer, the proportion of the other electron transporting material is properly from 0.1 to 40 weight parts and preferably from 0.5 to 20 weight parts, based on 100 weight parts of the polymeric binder.

The thickness of the photosensitive layer in the dual-layered type photoconductor is from about 0.01 to 5 μm and preferably from about 0.1 to 3 μm for the charge generation layer, and from about 5 to 80 μm and preferably from about 10 to 50 μm for the charge transport layer. A barrier layer may be formed between the conductive substrate and the photosensitive layer in the single-layered photoconductor in the ranges in which the properties of the photoconductor are not prevented. A barrier layer may be formed between the conductive substrate and the charge transport layer, between the conductive substrate and the charge transport layer or between the charge generation layer and the charge transport layer in the dual-layered type photoconductor, in the ranges in which the properties of the photoconductor are not prevented. Furthermore, a protecting layer may be formed on a surface of the photoconductor.

When the above photosensitive layer is formed by a coating method, the above-exemplified charge generating material, the charge transporting material, the polymeric binder and the like may be dispersed and mixed for adjusting a dispersion liquid using known methods such as a roll mill, a ball mill, an attritor, a paint shaker, an ultrasonic dispersion machine or the like, along with a suitable solvent. The resulting dispersion liquid was applied on the photosensitive layer and the resultant was dried according to the known methods.

As a solvent for preparing the above dispersion, several organic solvents can be used. Examples thereof include alcohols such as methanol, ethanol, isopropanol, butanol and the like; aliphatic hydrocarbons such as n-hexane, octane, cyclohexane and the like; aromatic hydrocarbons such as benzene, toluene, xylene and the like; halogenated hydrocarbons such as dichloromethane, dichloroethane, chloroform, carbon tetrachloride, chlorobenzene and the like; ethers such as dimethyl ether, diethyl ether, tetrahydrofuran, ethylene glycol dimethyl ether, diethylene glycol dimethyl ether and the like; ketones such as acetone, methyl ethyl ketone, cyclohexanone and the like; esters such as ethyl acetate, methyl acetate and the like; dimethyl formaldehyde, dimethylformamide, dimethyl sulfoxide and the like. These solvents are used singly or in combination of two or more kinds.

Figure 2:
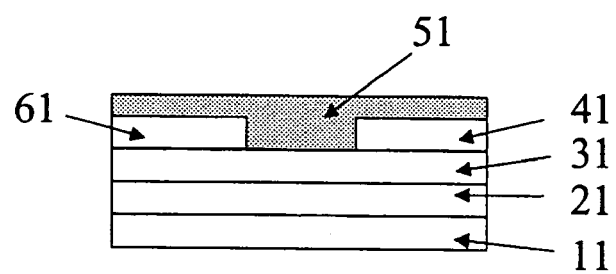
FIG. 2 is a schematic cross-sectional view illustrating an example of the organic thin film transistor according to the present invention.
Figure 3:
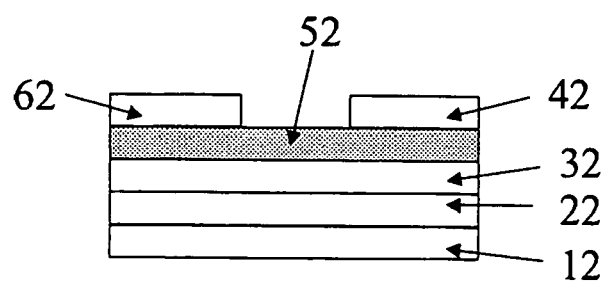
FIG. 3 is a schematic cross-sectional view illustrating another example of the organic thin film transistor according to the present invention.

Embodiments of the organic thin film transistor of the present invention will be explained with reference to the drawings. FIG. 2 is a schematic view illustrating an example of the organic TFT according to the present invention. This organic TFT is provided with a gate electrode 21 prepared on a substrate 11, an insulator layer 31 stacked on the gate electrode, a source electrode 61 and a drain electrode 41 formed at prescribed intervals thereon in parallel at the same time, and an organic thin film layer 51 formed thereon (bottom contact structure). Or, as shown in FIG. 3, a gate electrode 22 is formed on a substrate 12, an insulator layer 32 is stacked on the gate electrode, an organic thin film layer 52 is further stacked thereon, and a source electrode 62 and a drain electrode 42 are formed thereon in parallel at the same time (top contact structure).

In the organic TFT having such a structure, the organic thin film layer forms a channel region, and the current flowing between the source electrode and the drain electrode is controlled by the voltage applied on the gate electrode for on/off operations.

The organic thin film layer comprising the novel compound represented by the general formula (1) may be subjected to doping treatment. Doping herein refers to the action of introducing an electron accepting molecule (acceptor) or an electron donating molecule (donor) as impurities into the thin film. Therefore, a thin film subjected to doping comprises the novel compound represented by the general formula (1) and a dopant. As a dopant used in the present invention, either an acceptor or a donor can be used.

Any donor dopants can be used for the donor dopant of the present invention as far as they serve to donate electrons to the organic compound molecule of the organic thin film layer. Particularly suitable examples thereof include alkali metals such as Li, Na, K, Rb, Cs and the like; alkali earth metals such as Ca, Sr, Ba and the like; rare-earth metals such as Y, La, Ce, Pr, Nd, Sm, Eu, Gd, Tb, Dy, Ho, Er, Yb and the like; ammonium ion, $R_4P^+$, $R_4As^+$, $R_3S^+$, acetylcholine and the like.

Any acceptor dopants can be used for the acceptor dopant in the present invention as far as they serve to eliminate electrons from the organic compound molecule of the organic thin film layer. Particularly suitable examples thereof include halogens such as $Cl_2$, $Br_2$, $I_2$, ICl, $ICl_3$, IBr, IF and the like; Lewis acids such as $PF_5$, $AsF_5$, $SbF_5$, $BF_3$, $BCl_3$, $BBr_3$, $SO_3$ and the like; protonic acids such as HF, HCl, $HNO_3$, $H_2SO_4$, $HClO_4$, $FSO_3H$, $ClSO_3H$, $CF_3SO_3H$ and the like; organic acids such as acetic acid, formic acid, amino acid and the like; transition metal compounds such as $FeCl_3$, FeOCl, $TiCl_4$, $ZrCl_4$, $HfCl_4$, $NbF_5$, $NbCl_5$, $TaCl_5$, $MoCl_5$, $WF_5$, $WCl_6$, $UF_6$, $LnCl_3$ (Ln=Lanthanide such as La, Ce, Nd, Pr or the like, and Y) and the like; and electrolytic anion such as $Cl^-$, $Br^-$, $I^-$, $ClO_4^-$, $PF_6^-$, $AsF_5^-$, $SbF_6^-$, $BF_4^-$, sulfonate anion and the like.

Doping these dopants may be carried out by employing either a method in which a thin organic semiconductor film is previously prepared and subsequently, the dopants are incorporated, or a method in which dopants are incorporated during preparation of a thin organic semiconductor film. Listed as former methods may be a gas phase doping in which gaseous dopants are employed, a liquid phase doping in which doping is carried out while the thin film comes into contact with a dopant solution or liquid dopant, or a solid phase doping in which diffusion doping is carried out while the thin film comes into contact with a solid dopant. Further, in the liquid phase doping, it is possible to adjust the doping efficiency by carrying out electrolysis. In the latter methods, either a mixed solution or a dispersion, consisting of organic semiconductors and dopants, may be coated and subsequently dried. For example, when a vacuum deposition method is used as a method for forming an organic thin film to be described below, dopants can be incorporated by achieving co-deposition of dopants with organic semiconductor compounds together. Meanwhile, when a thin film is prepared by employing a sputtering method as a method for forming an organic thin film to be described below, dopants can be incorporated in the thin film through sputtering, utilizing the two-dimensional target of the organic semiconductor compounds and the dopants. Still further, as other methods, it is possible to use any of chemical doping methods such as electrochemical doping, photoinitiated doping and the like, or the physical doping methods such as an ion injection method and the like.

A method for forming the organic thin film according to the present invention is not particularly limited, and thin film forming methods which have been generally known from the past can be used. Concretely, it is possible to employ any of dry film forming methods such as a vacuum deposition method, a sputtering method, a plasma method, an ionized deposition method, an ion plating method, a cluster ion beam method and the like; or solution coating methods such as a spin coating method, a dip coating method, a flow coating method, a casting method, a bar coating method, a roll coating method, an ink jet printing method and the like. For the organic thin film layer used in the organic TFT comprising the compound represented by the above general formula (1), preferably used are a dip coating method, a spin coating method, a casting method, a bar coating method, a roll coating method and the like of a solution dissolved in a solvent.

The film thickness of the organic thin film layer in the present invention is not particularly limited. However, in general, when the film thickness is too small, it is easy to cause defects such as pinhole or the like. On the contrary, when the thickness is too large, channel length might get longer in some cases or high applied voltage might be needed in some cases depending on the structure of TFT. In such a case, the drive speed or on/off ratio becomes deteriorated. Accordingly, it is preferable to set the film thickness usually in the range of several nm to 1 μm.

Meanwhile, the substrate in the present invention is not particularly limited, and any substrates may be used. In generally suitably used is a plastic sheet or the like, in addition to glass including quartz or silicon wafer. Examples of the plastic sheet include a substrate comprising polyethylene terephthalate (PET), polyethylene naphthalate (PEN), polyethersulfone (PES), polyetherimide, polyether ether ketone, polyphenylenesulfide, polyarylate, polyimide, polycarbonate (PC), cellulose triacetate (TAC), cellulose acetate propionate (CAP) or the like.

Materials which can be used for the source, drain, and gate electrodes in the present invention are not particularly limited as long as they are electrically conductive materials. Examples thereof include fluorine-doped zinc oxide, carbon, graphite, glassy carbon, silver paste, carbon paste and the like, in addition to metals or alloys such as indium tin oxide alloy (ITO), tin oxide (NESA), gold, silver, platinum, copper, indium, aluminum, magnesium, nickel, chromium, iron, tin, tantalum, palladium, tellurium, iridium, ruthenium, germanium, tungsten, lithium, beryllium, sodium, potassium, calcium, zinc, magnesium/indium alloy, magnesium/copper alloy, magnesium/silver alloy, magnesium/aluminum alloy, aluminum/lithium alloy, aluminum/scandium/lithium alloy, sodium/potassium alloy and the like. Particularly preferably used are platinum, gold, silver, copper, aluminum, indium, ITO and carbon. Alternatively, suitably employed are electrically conductive polymers, known in the art, such as electrically conductive polyaniline, electrically conductive polypyrrole, electrically conductive polythiophene, and complexes of polyethylenedioxy thiophene (PEDOT) and polystyrene sulfonic acid (PSS) which increase electrical conductivity upon being doped. In the aforementioned materials, for the source and drain electrodes, preferably used are materials with smaller electric resistance at the surface in contact with the organic thin film layer.

Examples of the method for forming electrodes include a method in which an electrode is prepared in such a manner that a photolithographic method or a lift-off method, known in the art, is applied to electrically conductive thin film, which has been formed by employing evaporation, sputtering method or the like while employing the aforementioned compounds as a raw material, and a method in which etching is conducted by employing a resist which has been prepared by employing thermal transfer, ink jet printing or the like onto a foil of metal such as aluminum, copper or the like. Further, an electrically conductive polymer solution or dispersion, or a minute electrically conductive particle dispersion may be subjected directly to patterning by employing ink jet printing. The electrode may also be formed in such a manner that a coated film is subjected to lithograph, laser ablation or the like. In addition, a method may also be employed in which ink comprising either an electrically conductive polymer or minute electrically conductive particles, or electrically conductive paste is subjected to patterning by employing any of the printing methods such as letter press, intaglio printing, lithography, screen printing or the like.

Various insulation materials can be employed for a material used as an insulator layer of the gate insulation layer in the present invention. However, particularly preferably used are inorganic oxide films or organic compound films with a high dielectric constant. Examples of the inorganic oxide include silicon oxide, silicon nitride, aluminum oxide, tantalum oxide, titanium oxide, tin oxide, vanadium oxide, barium strontium titanate, barium zirconate titanate, lead zirconate titanate, lead lanthanum titanate, strontium titanate, barium titanate, barium magnesium fluoride, bismuth titanate, strontium bismuth titanate, strontium bismuth tantalate, bismuth tantalate niobate, tantalum pentoxide, titanium dioxide, yttrium trioxide and the like. Of these, preferably used are silicon oxide, silicon nitride, aluminum oxide, tantalum oxide and titanium oxide.

Examples of the method for forming the inorganic oxide film include dry processes such as a vacuum deposition method, a molecular beam epitaxy, an ion cluster beam method, a low energy ion beam method, an ion plating method, a CVD method, a sputtering method, an atmospheric pressure plasma method and the like; and wet processes using coating methods such as a spray coating method, a spin coating method, a blade coating method, a dip coating method, a casting method, a roll coating method, a bar coating method, a die coating method and the like as well as methods employing patterning such as printing, ink jet printing and the like. It is possible to employ any of these methods depending on materials.

As the organic compound film used for the gate insulation layer, there can also be used, for example, polyimide, polyamide, polyester, polyacrylate, photoradical polymerization type photocurable resin, photocationic polymerization type photocurable resin, a copolymer containing an acrylonitrile ingredient, poly(vinyl phenol), poly(vinyl alcohol), a novolac resin, poly(vinylidene fluoride) (PVF), cyanoethyl pullulan and the like. As a method for forming the organic compound film, preferably used are the above wet processes.

Embodiments of the organic electroluminescent device of the present invention will be explained.

The organic electroluminescent device is usually composed of one organic thin film layer or a plurality of organic thin film layers formed between a pair of electrodes. In a single-layered device, a light-emitting layer is formed between a pair of electrodes. The light-emitting layer contains at least one kind of light-emitting material, and in addition thereto, it may also contain a hole injecting and transporting material for transporting holes injected from the anode to the light-emitting material, or an electron injecting and transporting material for transporting electrons injected from the cathode to the light-emitting material. In a multi-layered device, the organic electroluminescent device is stacked in one of multi-layered structures such as (A) anode/hole injecting and transporting layer/light-emitting layer/cathode, (B) anode/light-emitting layer/electron injecting and transporting layer/cathode and (C) anode/hole injecting and transporting layer/light-emitting layer/electron injecting and transporting layer/cathode In addition, the organic electroluminescent device can also be of a multi-layered structure such that a hole blocking layer is stacked between the light-emitting layer and the electron injecting and transporting layer, i.e., (D) anode/hole injecting and transporting layer/light-emitting layer/hole blocking layer/electron injecting and transporting layer/cathode.

In the organic electroluminescent device of the present invention, device structure is not limited thereto. In the respective devices, it is possible to form a plurality of layers such as a hole injecting and transporting layer, a light-emitting layer, and an electron injecting and transporting layer. In addition, in the respective devices, it is possible to form a mixed layer of a hole injecting and transporting material and a light-emitting material between the hole injecting and transporting layer and the light-emitting layer, and/or a mixed layer of a light-emitting material and an electron injecting and transporting material between the light-emitting layer and the electron injecting and transporting layer.

The novel compound of the general formula (1) can be used in any one of the above structures. The novel compound of the general formula (1) can be used as an electron injecting and transporting material in any of the electron injecting and transporting layer or the hole blocking layer. The electron injecting and transporting material of the present invention has the function of injecting electrons to the organic layer from the cathode and the function of transporting the injected electrons for injecting electrons to the light-emitting layer. Therefore, the electron injecting and transporting material can be used in any electron injecting and transporting layer even when the electron injecting and transporting layer is formed of two or more layers.

A thin film formed by the novel compound of the general formula (1) is amorphous, so that it is advantageous for the storage of the thin film for a long time and for the light emission life when the device is driven. Further, the novel compound of the general formula (1) has excellent adhesion to a metal electrode and has a low affinity of the thin film for electrons, so that it is advantageous in the injection of electrons from the cathode. Therefore, when the electron injecting and transporting layer is formed of two layers or more, it is further advantageous to use the novel compound of the general formula (1) in the electron injecting and transporting layer located on the metal electrode (cathode) side.

Herein, the hole injecting and transporting layer, the light-emitting layer, and the electron injecting and transporting layer may be formed of two layers or more respectively.

Examples of the hole injecting and transporting material include compounds which have the function of injecting holes from the anode, have the function of injecting holes to the light-emitting layer or the light-emitting material, prevent the movement of excitons generated in the light-emitting layer to the electron injecting and transporting layer or the electron injecting and transporting material, and have the excellent capability of forming a thin film. Specific examples thereof include phthalocyanine derivatives, naphthalocyanine derivatives, porphyrin derivatives, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and an electrically conductive polymer such as poly(vinylcarbazole), polysilane, polythiophene, polyaniline and the like. However, the hole injecting and transporting material is not limited to the above materials. The hole injecting and transporting materials may be used singly or in mixture of a plurality thereof.

In the hole injecting and transporting material which can be used in the organic electroluminescent device of the present invention, more effective hole injecting and transporting materials are tertiary aromatic amine derivatives or phthalocyanine derivatives. Concrete examples of the tertiary aromatic amine derivative include, though not restrict to, triphenylamine, tritolylamine, tolyldiphenylamine, N,N'-diphenyl-N,N'-bis(3-methylphenyl)-1,1'-biphenyl-4,4'-diamine (TPD), 4,4'-bis[N-(1-naphthyl)-N-phenyl-amino] biphenyl (α-NPD), N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane and the like, or oligomer or polymer having a tertiary aromatic amine moiety.

Examples of the phthalocyanine (Pc) derivative include phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc and the like. However, the phthalocyanine (Pc) derivative is not limited thereto.

When the compound according to the present invention is used for a hole blocking layer, examples of the electron injecting and transporting material which can be used include compounds which have the function of injecting electrons from the cathode, have the function of injecting electrons to the light-emitting layer or the light-emitting material, prevent the movement of excitons generated in the light-emitting layer to the hole injecting and transporting layer or the hole injecting and transporting material, and have the excellent capability of forming a thin film. Specific examples thereof include quinoline metal complex, oxadiazole, benzothiazole metal complex, benzoxazole metal complex, benzoimidazole metal complex, fluorenone, anthraquinodimethane, diphenoquinone, thiopyran dioxide, oxadiazole, thiadiazole, tetrazole, perylenetetracarboxylic acid, fluorenilidene methane, anthraquinodimethane, anthrone, derivatives of these and the like. The electron injecting and transporting materials may be used singly or in mixture of a plurality thereof.

When the compound according to the present invention and other electron injecting and transporting materials are used together, the proportion of the compound according to the present invention occupied in the electron injecting and transporting layer is preferably adjusted to from about 0.1 to 60 weight %.

In the organic electroluminescent device of the present invention, more effective electron injecting and transporting materials are metal complex compounds. In these compounds, for example, suitably used are organic aluminum complexes represented by the general formulae (a) to (c), (Q) 3-Al                                            (a)

wherein, in the formula, Q represents a substituted or unsubstitued 8-quinolinolato ligand, (Q) 2-Al—O-L                            (b)

wherein, in the formula, Q represents a substituted 8-quinolinolato ligand; O-L represents a phenolato ligand; and L represents a hydrocarbon group having 6 to 24 carbon atoms containing a phenyl portion, and (Q) 2-Al—O—Al-(Q)2                     (c)

wherein, in the formula, Q represents a substituted 8-quinolinolato ligand.

Concrete examples of the organoaluminum complex having a substituted or unsubstituted 8-quinolinolato ligand include tris(8-quinolinolato)aluminum, tris(4-methyl-8-quinolinolato)aluminum, tris(5-methyl-8-quinolinolato)aluminum, tris(3,4-dimethyl-8-quinolinolato)aluminum, tris(4,5-dimethyl-8-quinolinolato)aluminum, tris(4,5-dimethyl-8-quinolinolato)aluminum, bis(2-methyl-8-quinolinolato) (phenolato)aluminum, bis(2-methyl-8-quinolinolato) (2-methylphenolato)aluminum, bis(2-methyl-8-quinolinolato) (3-methylphenolato)aluminum, bis(2-methyl-8-quinolinolato) (4-methylphenolato)aluminum, bis(2-methyl-8-quinolinolato) (2-phenylphenolato)aluminum, bis(2-methyl-8-quinolinolato) (3-phenylphenolato)aluminum, bis(2-methyl-8-quinolinolato) (4-phenylphenolato)aluminum, bis(2-methyl-8-quinolinolato) (2,3-dimethylphenolato) aluminum, bis(2-methyl-8-quinolinolato) (2,6-dimethylphenolato)aluminum, bis(2-methyl-8-quinolinolato) (3,4-dimethylphenolato)aluminum, bis(2-methyl-8-quinolinolato) (3,5-dimethylphenolato) aluminum, bis(2-methyl-8-quinolinolato) (3,5-di-tert-butylphenolato) aluminum, bis(2-methyl-8-quinolinolato) (2,6-diphenylphenolato)aluminum, bis(2-methyl-8-quinolinolato) (2,4,6-triphenylphenolato)aluminum, bis(2-methyl-8-quinolinolato) (2,4,6-trimethylphenolato)aluminum, bis(2-methyl-8-quinolinolato) (2,4,5,6-tetramethylphenolato) aluminum, bis(2-methyl-8-quinolinolato) (1-naphtholato) aluminum, bis(2-methyl-8-quinolinolato) (2-naphtholato) aluminum, bis(2,4-dimethyl-8-quinolinolato) (2-phenylphenolato)aluminum, bis(2,4-dimethyl-8-quinolinolato) (3-phenylphenolato)aluminum, bis(2,4-dimethyl-8-quinolinolato) (4-phenylphenolato)aluminum, bis(2,4-dimethyl-8-quinolinolato) (3,5-dimethylphenolato)aluminum, bis(2,4-dimethyl-8-quinolinolato) (3,5-di-tert-butylphenolato)aluminum, bis(2-methyl-8-quinolinolato)aluminum-µ-oxo-bis(2-methyl-8-quinolinolato) aluminum,bis(2,4-dimethyl-8-quinolinolato)aluminum-µ-oxo-bis(2,4-dimethyl-8-quinolinolato)aluminum, bis(2-methyl-4-ethyl-8-quinolinolato)aluminum-µ-oxo-bis(2-methyl-4-ethyl-8-quinolinolato)aluminum, bis(2-methyl-4-methoxy-8-quinolinolato)aluminum-µ-oxo-bis(2-methyl-4-methoxy-8-quinolinolato)aluminum, bis(2-methyl-5-cyano-8-quinolinolato)aluminum-µ-oxo-bis(2-methyl-5-cyano-8-quinolinolato)aluminum, bis(2-methyl-5-trifluoromethyl-8-quinolinolato)aluminum-µ-oxo-bis(2-methyl-5-trifluoromethyl-8-quinolinolato)aluminum and the like. Of course, these organometallic complexes may be used singly or in mixture of a plurality thereof.

Examples of the light-emitting material or doping material which can be used for the organic electroluminescent device of the present invention include, though not restricted to, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinylanthracene, diaminocarbazole, triphenylamine, benzidine type triphenylamine, styrylamine type triphenylamine, diamine type triphenylaminepyran, thiopyran, polymethine, merocyanine, imidazole-chelated oxynoid compounds, quinacridone, rubrene, and derivatives of these.

Examples of the light-emitting material which can be used for the organic electroluminescent device of the present invention include phosphorescent (triplet emission) compounds. Concrete examples thereof include tris(2-phenylpyrimidyl)iridium complex, tris[2-(2'-fluorophenyl)pyridyl]iridium complex, bis(2-phenylpyridyl)acetylacetonato iridium complex, bis[2-(2',4'-difluorophenyl)pyridyl]acetylacetonato iridium complex, 2,3,7,8,12,13,17,18-octaethyl-21H, 23H porphyrin platinum complex and the like.

The electrically conductive material used for the anode of the organic electroluminescent device suitably has a work function of greater than 4 eV. Examples thereof include carbon, aluminum, vanadium, iron, cobalt, nickel, tungsten, silver, gold, platinum, palladium, alloys thereof, metal oxides such as indium tin oxide (ITO), tin oxide (NESA) and the like, electrically conductive polymers, known in the art, such as polythiophene, polypyrrole or the like, complexes such as polyethylenedioxy thiophene (PEDOT), polystyrene sulfonic acid (PSS), and the like. These electrically conductive materials may be used singly or in mixture of a plurality thereof.

The anode may be of a single-layered structure or a multi-layered structure.

The electrical sheet resistance of the anode is preferably set to several hundreds of $\Omega/\square$ and more preferably from about 5 to 50 $\Omega/\square$.

The thickness of the anode is different depending on the electrically conductive material in use, but is generally set to from about 5 to 1,000 nm and more preferably from about 10 to 500 nm.

The electrically conductive material used for the cathode suitably has a work function of smaller than 4 eV. Examples thereof include magnesium, calcium, tin, lead, titanium, yttrium, lithium, lithium fluoride, ruthenium, manganese and alloys thereof. Typical examples of the alloys include, though not restricted to, lithium/indium, magnesium/silver, magnesium/indium, lithium/aluminum and the like. The proportion of the alloys is controlled by the heating temperature, atmosphere and vacuum degree, and the suitable proportion is selected. The electrically conductive material may be used singly or in mixture of a plurality thereof.

The cathode may be of a single-layered structure or a multi-layered structure.

The electrical sheet resistance of the cathode is preferably set to not more than several hundreds of $\Omega/\square$. The thickness of the cathode is different depending on the electrically conductive material in use, but is generally set to from about 5 to 1,000 nm and more preferably from about 10 to 500 nm.

A method for forming electrodes (anode, cathode) of the organic electroluminescent device according to the present invention is not particularly limited, and thin film forming methods which have been generally known from the past can be used. Concretely, it is possible to employ any of dry film forming methods such as a vacuum deposition method, a sputtering method, a plasma method, an ionized deposition method, an ion plating method, a cluster ion beam method and the like; and solution coating methods such as a spin coating method, a dipping method, a flow coating method, a casting method, a bar coating method, an ink jet printing method and the like.

For the effective light emission of the organic electroluminescent device, at least one of the electrodes is desirably transparent in the light emission wavelength region of the device. Further, the substrate is desirably transparent. The transparent electrode is set using the above electrically conductive material such that a predetermined transparency is secured according to a deposition method or a sputtering method. The electrode of a light emission surface preferably has a light transmittance of not less than 50% and more preferably not less than 70%. The substrate is not limited so long as it has mechanical and thermal strength and is transparent. Examples thereof include glass substrates and substrates of transparent polymers such as polyethylene, polyether sulfone, polypropylene and the like.

When the organic electroluminescent device is formed of a multi-layered structure, the multi-layered structure can serve to prevent a quenching-induced decrease in the brightness and the device lifetime. In the above multi-layered structure, a light-emitting material, a doping material, a hole injecting and transporting material and an electron injecting and transporting material for injecting a carrier can also be used in combination of two or more kinds as required. Further, each of the hole injecting and transporting layer, the light-emitting layer, and the electron injecting and transporting layer may be formed of two layers or more, and a device structure in which holes or electrons are effectively injected from the electrodes and transported in the layers is selected.

A method for forming each layer (hole injecting and transporting layer, light-emitting layer, and electron injecting and transporting layer) of the organic electroluminescent device according to the present invention is not particularly limited, and thin film forming methods which have been generally known from the past can be used. Concretely, it is possible to employ any of dry film forming methods such as a vacuum deposition method, a sputtering method, a plasma method, an ionized deposition method, an ion plating method, a cluster ion beam method and the like; and solution coating methods such as a spin coating method, a dipping method, a flow coating method, a casting method, a bar coating method, an ink jet printing method and the like.

The film thickness is not particularly limited, but each layer is required to have an appropriate thickness. When the film thickness is too large, inefficiently, a high applied voltage is required to achieve predetermined emission of light. When the film thickness is too small, the layer is liable to have a pinhole and the like so that sufficient light emission brightness is hardly obtained even when an electric field is applied. In generally, the thickness is preferably from about 1 nm to 1 µm and more preferably from about 10 nm to 0.2 µm.

When each layer is formed by a vacuum deposition method, the conditions for vacuum deposition are not particularly limited, but each layer is preferably formed under vacuum of about $10^{-5}$ Torr at a boat temperature (deposition source temperature) of from about 50° C. to 600° C., a substrate temperature of from about −50° C. to 300° C., and a deposition rate of from about 0.005 to 50 nm/sec.

When each layer of the hole injecting and transporting layer, the light-emitting layer, and the electron injecting and transporting layer is formed by the vacuum deposition method using a plurality of compounds, it is preferable to conduct co-deposition by separately controlling temperatures of boats filled with the compounds. In this case, the organic electroluminescent device with excellent properties in general can be produced by continuously forming each layer of the hole injecting and transporting layer, the light-emitting layer, and the electron injecting and transporting layer under vacuum.

When each layer is formed by a solution coating method, materials constituting each layer, or the materials and a binder polymer are dissolved or dispersed in a solvent to form a coating solution. Examples of the binder polymer that can be used in each layer of the hole injecting and transporting layer, the light-emitting layer, and the electron injecting and transporting layer include insulating polymers such as polystyrene, polycarbonate, polyarylate, polyester, polyamide, polyimide, polyurethane, polysiloxane, polysulfone, poly(methyl methacrylate), poly(methyl acrylate), cellulose and the like; photoconductive polymers such as poly(vinylcarbozole) (PVK), polysilane and the like; and electrically conductive polymers such as polythiophene, polypyrrole, polyaniline and the like. The binder polymers may be used singly or in mixture of a plurality thereof.

When each layer is formed by a solution coating method, materials constituting each layer, or the materials and the binder polymer are dissolved or dispersed in an appropriate organic solvent (for example, hydrocarbon solvents such as hexane, octane, decane, toluene, xylene, ethylbenzene, 1-methylnaphthalene and the like; ketone solvents such as acetone, methyl ethyl ketone, methyl isobutyl ketone, cyclohexanone and the like; halogenated hydrocarbon solvents such as dichloromethane, chloroform, tetra chloromethane, dichloroethane, trichloroethane, tetrachloroethane, chlorobenzene, dichlorobenzene, chlorotoluene and the like; ester solvents such as ethyl acetate, butyl acetate, amyl acetate and the like; alcohol solvents such as methanol, propanol, butanol, pentanol, hexanol, cyclohexanol, ethyleneglycol monomethyl ether, ethyleneglycol monoethyl ether, ethylene glycol and the like; ether solvents such as dibutyl ether, tetrahydrofuran, dioxane, anisole and the like; polar solvents such as N,N-dimethylformamide, N,N-dimethylacetamide, 1-methyl-2-pyrrolidone, 1-methyl-2-imidazolidinone, dimethyl sulfoxide and the like) and/or in water to form a coating solution, and a thin film can be formed by various coating methods.

Incidentally, the dispersion method is not particularly limited. The dispersion can be conducted in the form of fine particles using a ball mill, a sand mill, a paint shaker, an attritor, a homogenizer or the like.

The concentration of the coating solution is not particularly limited, and can be set at a range suitable for providing a desired thickness according to a coating method to be performed. The concentration of the solution is generally from about 0.1 to 50 weight % and preferably from about 1 to 30 weight %. By the way, in case of using the binder polymer, the amount thereof is not particularly limited, but is generally set to from about 5 to 99.9 weight %, preferably from about 10 to 99.9 weight %, and more preferably from about 15 to 90 weight %, based on materials constituting each layer (to form a single-layered device, based on the total amount of the respective components).

In order to prevent the formed device from brining into contact with oxygen or moisture, it is preferable to form a protecting layer (sealing layer), and it is possible to protect the device by sealing the same in an inactive substance (for example, paraffin, liquid paraffin, silicone oil, fluorocarbon oil, zeolite-containing fluorocarbon oil or the like).

Examples of the material used in the protecting layer include organic polymer materials (for example, a fluorinated resin, an epoxy resin, a silicone resin, an epoxy silicone resin, polystyrene, polyester, polycarbonate, polyamide, polyimide, polyamideimide, poly-p-xylene, polyethylene, and polyphenylene oxide), inorganic materials (for example, a diamond thin film, an amorphous silica, an electric insulating glass, a metal oxide, metal nitride, a metal carbide, and a metal sulfide), photocurable resins and the like. Further, the materials used in the protecting layer may be used singly or in mixture of a plurality thereof. The protecting layer may be of a single-layered structure or a multi-layered structure.

The organic electroluminescent device of the present invention can be usually used as a direct current driving-type device, and can also be used as an alternating current driving-type device. In addition, the organic electroluminescent device of the present invention may be a passive driving type such as a segment type, a passive matrix driving type or the like, or an active driving type such as a TFT (thin film transistor) type, an MIM (metal-insulator-metal) type or the like. A drive voltage is usually from 2 to 30 V. The organic electroluminescent device of the present invention can be used in, for example, panel type light sources (for example, back light such as watch, liquid crystal panel and the like), various light-emitting devices (for example, substitution of light-emitting device such as LED and the like), various display devices [for example, information display devices (PC monitor, display devices for cellular phones and portable terminals)], various marks, various sensors and the like.

Embodiments of the organic solar cell of the present invention will be explained hereinafter.

The organic solar cell of the present invention is usually composed of one organic thin film layer or a plurality of organic thin film layers formed between a pair of electrodes. In a single-layered device, an active layer is formed between a pair of electrodes. Herein, the active layer is formed in mixture of at least an organic p-type semiconductor and an organic n-type semiconductor. In a multi-layered device, the organic solar cell is stacked in one of multi-layered structures such as (A) electrode/organic p-type semiconductor layer/active layer/electrode, (B) electrode/active layer/organic n-type semiconductor layer/electrode, (C) electrode/organic p-type semiconductor layer/active layer/organic n-type semiconductor layer/electrode. Herein, the organic p-type semiconductor layer or the organic n-type semiconductor layer may be respectively formed of two layers or more.

The novel compound of the general formula (1) can be used in any of the above structures. The novel compound of the general formula (1) can be used as an electron transporting material in any one of the active layer and the organic n-type semiconductor layer. The electron transporting material of the present invention has the function of injecting electrons to the organic n-type semiconductor layer from the active layer and the function of transporting the injected electrons for injecting electrons to the electrode, and the electron transporting material can be used in any organic n-type semiconductor layer even when the organic n-type semiconductor layer is formed of two or more layers.

Examples of the organic p-type semiconductor includes compounds which have the ability of transporting holes from the active layer and the ability of injecting holes to the electrode. Specific examples thereof include phthalocyanine derivatives, naphthalocyanine derivatives, porphyrin derivatives, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and an electrically conductive polymer such as poly (vinylcarbazole) (PVK), polysilane, polythiophene, polyaniline and the like. However, the organic p-type semiconductor is not limited to the above materials. The organic p-type semiconductor may be used singly or in mixture of a plurality thereof.

When the compound according to the present invention is used for the active layer, examples of the organic n-type semiconductor which can be used include compounds which have the ability of transporting electrons from the active layer, and the ability of injecting electrons to the electrode. Specific examples thereof include quinoline metal complex, benzothiazole metal complex, benzoxazole metal complex, benzimidazole metal complex, 2,4,7-trinitrofluorenone, anthraquinodimethane, diphenoquinone, naphthoquinone, anthraquinone, stilbenequinone, thiopyran dioxide, oxadiazole, thiadiazole, tetrazole, perylenetetracarboxylic acid, fluorenilidene methane, anthraquinodimethane, anthrone, fullerene, silole, and derivatives of these. The organic n-type semiconductor is not limited to the above materials. The organic n-type semiconductor may be used singly or in mixture of a plurality thereof.

A method for forming the organic thin film according to the present invention is not particularly limited, and thin film forming methods which have been generally known from the past can be used. Concretely, it is possible to employ any of dry film forming methods such as a vacuum deposition method, a sputtering method, a plasma method, an ionized deposition method, an ion plating method, a cluster ion beam method and the like; or solution coating methods such as a spin coating method, a dipping method, a flow coating method, a casting method, a bar coating method, an ink jet printing method and the like.

The film thickness of the organic thin film layer in the present invention is not particularly limited. However, in general, when the film thickness is too small, light absorption efficiency might be lowered. On the contrary, when the thickness is too large, carriers generated at the active layer might be lost before transported to the electrode in some cases. In such a case, as a result, the conversion efficiency is deteriorated. Accordingly, it is preferable to set the film thickness usually in the range of several nm to 1 μm.

When each layer is formed by a vacuum deposition method, the conditions for vacuum deposition are not particularly limited, but each layer is preferably formed under vacuum of about $10^{-5}$ Torr at a boat temperature (deposition source temperature) of from about 50° C. to 600° C., a substrate temperature of about from −50° C. to 300° C., and a deposition rate of from about 0.005 to 50 nm/sec.

When each layer of the organic p-type semiconductor layer, the active layer and the organic n-type semiconductor layer is formed by the vacuum deposition method using a plurality of compounds, it is preferable to conduct co-deposition by separately controlling temperatures of boats filled with the compounds.

When each layer is formed by a solution coating method, materials constituting each layer, or the materials and a binder polymer are dissolved or dispersed in a solvent to form a coating solution. Examples of the binder polymer which can be used in each layer of the organic p-type semiconductor layer, the active layer and the organic n-type semiconductor layer include insulating polymers such as polystyrene, polycarbonate, polyarylate, polyester, polyamide, polyimide, polyurethane, polysiloxane, polysulfone, poly(methyl methacrylate), poly(methyl acrylate), cellulose and the like; photoconductive polymers such as poly(vinylcarbazole), polysilane and the like; and electrically conductive polymers such as polythiophene, polypyrrole, polyaniline and the like. The binder polymers may be used singly or in mixture of a plurality thereof.

When each layer is formed by a solution coating method, materials constituting each layer, or the materials and the binder polymer are dissolved or dispersed in an appropriate organic solvent (for example, hydrocarbon solvents such as hexane, octane, decane, toluene, xylene, ethylbenzene, 1-methylnaphthalene and the like; ketone solvents such as acetone, methyl ethyl ketone, methyl isobutyl ketone, cyclohexanone and the like; halogenated hydrocarbon solvents such as dichloromethane, chloroform, tetrachloromethane, dichloroethane, trichloroethane, tetrachloroethane, chlorobenzene, dichlorobenzene, chlorotoluene and the like; ester solvents such as ethyl acetate, butyl acetate, amyl acetate and the like; alcohol solvents such as methanol, propanol, butanol, pentanol, hexanol, cyclohexanol, ethyleneglycol monomethyl ether, ethyleneglycol monoethyl ether, ethylene glycol and the like; ether solvents such as dibutyl ether, tetrahydrofuran, dioxane, anisole and the like; polar solvents such as N,N-dimethylformamide, N,N-dimethylacetamide, 1-methyl-2-pyrrolidone, 1-methyl-2-imidazolidinone, dimethyl sulfoxide and the like) and/or in water to form a coating solution, and a thin film can be formed by various coating methods.

Incidentally, the dispersion method is not particularly limited. The dispersion can be conducted in the form of fine particles using a ball mill, a sand mill, a paint shaker, an attritor, a homogenizer or the like.

A material which can be used for the electrode in the present invention is used in combination of an electrode material having a high work function and an electrode material having a low work function. By combining the electrode material having a high work function with the electrode material having a low work function, the organic thin film can be provided with built-in electric field. Typical examples of the electrode material having a high work function include carbon, aluminum, vanadium, iron, cobalt, nickel, tungsten, silver, gold, platinum, palladium, alloys of these, metal oxides such as indium tin oxide alloy (ITO), tin oxide (NESA) and the like, electrically conductive polymers, known in the art, such as polythiophene, polypyrrole and the like, complexes such as polyethylenedioxy thiophene (PEDOT), polystyrene sulfonic acid (PSS) and the like. The electrode materials are not restricted the above materials. These electrode materials may be used singly or in mixture of a plurality thereof.

Examples of the electrode material having a low work function include magnesium, calcium, tin, lead, titanium, yttrium, lithium, fluorinated lithium, ruthenium, manganese, and alloys of these. Typical examples of the alloy include, though not restricted to, lithium/indium alloy, magnesium/silver alloy, magnesium/indium alloy, lithium/aluminum alloy and the like. The proportion of the alloy is controlled by the heating temperature, atmosphere and vacuum degree, and the suitable proportion is selected. These electrode materials may be used singly or in mixture of a plurality thereof.

The thickness of the electrode is different depending on the electrically conductive materials in use, but is usually from 1 to 500 nm, and preferably from 10 to 200 nm. When the film thickness is too small, the sheet resistance of the electrode becomes too large and it is unable to sufficiently transport the generated light electric charges to outside circuits. When it is too large, a transmittance of the irradiated light might be worsened, resulting in deteriorating the conversion efficiency.

EXAMPLES

The present invention is now more specifically illustrated below with reference to Examples. However, the present invention is not limited to these Examples. Monoimide monoanhydride derivative that is a starting material of the following Examples was adjusted according to the method as described in J. Am. Chem. Soc., 120, 3231 (1998) or by slightly changing the process as described therein.

Example 1

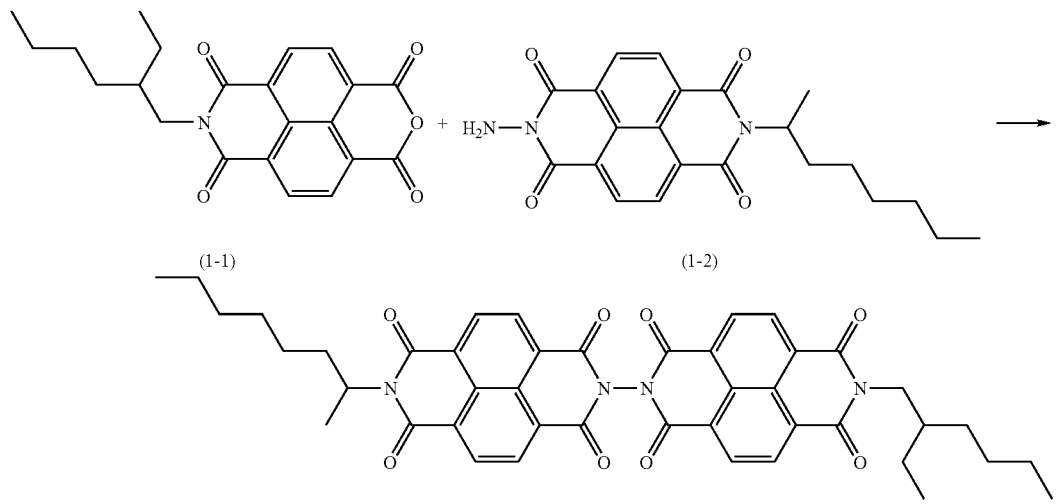

First Step: Synthesis of Naphthalene Monoimide Derivative (1-1)

8.0 g of a naphthalene-1,4,5,8-tetracarboxylic dianhydride and 50 ml of dehydrated DMF were introduced into a reactor. The reactor was heated to reflux. 3.85 g of 2-ethylhexylamine dissolved in 30 ml of dehydrated DMF was added dropwise into the reactor while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired naphthalene monoimide derivative (1-1). Yield: 3.89 g.

Second Step: Synthesis of Naphthalene Monoimide Monohydrazone Derivative (1-2)

12.0 g of a naphthalene-1,4,5,8-tetracarboxylic dianhydride and 60 ml of dehydrated DMF were introduced into a reactor. The reactor was heated to reflux. 5.78 g of 2-aminooctane dissolved in 30 ml of dehydrated DMF was added dropwise into the reactor while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to a naphthalene monoimide derivative. Yield: 7.98 g.

5.0 g of the resulting naphthalene monoimide derivative and 50 ml of dehydrated DMF were introduced and dissolved. Then, 0.48 g of hydrazine monohydrate was added dropwise thereto and the resultant was reacted at room temperature for 4 hours. Methanol was added dropwise thereto for precipitating a crystal. The crystal was filtered off, washed with methanol and dried to obtain a naphthalene monoimide monohydrazone derivative (1-2).

Yield: 3.56 g.

Third Step 3.0 g of the naphthalene monoimide derivative (1-1), 2.0 g of the naphthalene monoimide monohydrazone derivative (1-2) and 50 ml of dehydrated DMI were introduced into a reactor. In the reactor, these were reacted at 190° C. for 22 hours. The resultant was cooled and extracted to obtain an organic layer, and the organic layer was concentrated to obtain a solid.

The resulting solid was purified by column chromatography and further purified by recrystallization to obtain a light yellow solid. Yield: 1.14 g. When the melting point was measured, it was 210.9° C. As a result of mass spectrometry according to FD-MS, M/z was 755, from which it was identified as the desired product.

Example 2

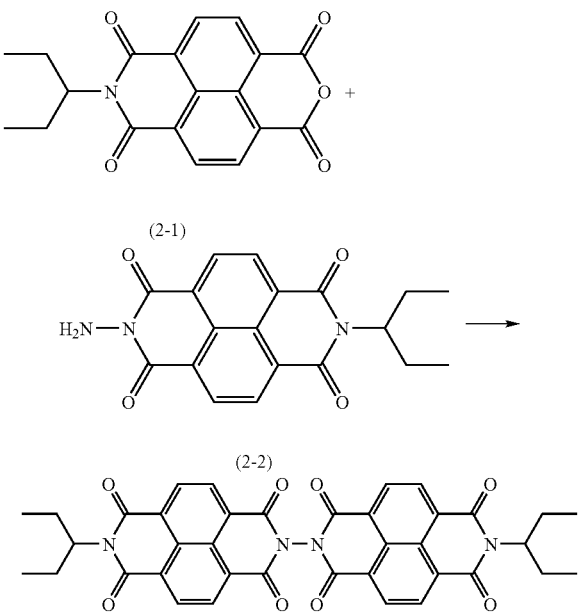

First Step: Synthesis of Naphthalene Monoimide Derivative (2-1)

27.0 g of a naphthalene-1,4,5,8-tetracarboxylic dianhydride and 250 ml of dehydrated DMF were introduced into a reactor. The reactor was heated to reflux. 9.0 g of 3-aminopentane dissolved in 100 ml of dehydrated DMF was added dropwise into the reactor for 30 minutes while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired product of a light yellow monoimide derivative (2-1). Yield: 13.3 g.

Second Step: Synthesis of Naphthalene Monoimide Monohydrazone Derivative (2-2)

10.0 g of the naphthalene monoimide derivative (2-1) obtained as above and 100 ml of dehydrated DMF were introduced and dissolved. Then, 1.65 g of hydrazine monohydrate was added dropwise thereto over 2 minutes and the resultant was reacted at room temperature for 1.5 hours. The precipitated crystal was filtered off, washed with methanol and dried to obtain a naphthalene monoimide monohydrazone derivative (2-2). Yield: 8.27 g.

Third Step 1.92 g of the naphthalene monoimide derivative (2-1), 2.0 g of the naphthalene monoimide monohydrazone derivative (2-2) and 100 ml of dehydrated DMF were introduced into a reactor. In the reactor, these were reacted under reflux for 58 hours. The precipitated crystal was filtered off, and then dissolved in toluene and hexane was added thereto for precipitating to obtain the desired product. Yield: 1.7 g.

When the melting point was measured, it was 366° C. As a result of mass spectrometry according to FD-MS, M/z was 670, from which it was identified as the desired product.

Example 3

First Step: Synthesis of Naphthalene Monoimide Derivative (3-1)

42.0 g of a naphthalene-1,4,5,8-tetracarboxylic dianhydride and 400 ml of dehydrated DMF were introduced into a reactor. The reactor was heated to reflux. 18.9 g of 2-heptylamine dissolved in 100 ml of dehydrated DMF was added dropwise into the reactor over 50 minutes while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired product of a light yellow monoimide derivative (3-1). Yield: 25.3 g.

Second Step: Synthesis of Naphthalene Monoimide Monohydrazone Derivative (3-2)

A naphthalene monoimide monohydrazone derivative (3-2) was produced in the same manner as in the second step of Example 2.

Third Step 2.66 g of the naphthalene monoimide monohydrazone derivative (3-2), 3.32 g of the naphthalene monoimide derivative (3-1) and 120 ml of dehydrated DMF were introduced into a reactor. In the reactor, these were reacted under reflux for 51 hours. After cooling, the resulting mixture was concentrated under a reduced pressure and the residue was purified by silica gel column chromatography to obtain the desired product. Yield: 2.3

When the melting point was measured, it was 268.9° C. As a result of mass spectrometry according to FD-MS, M/z was 698, from which it was identified as the desired product.

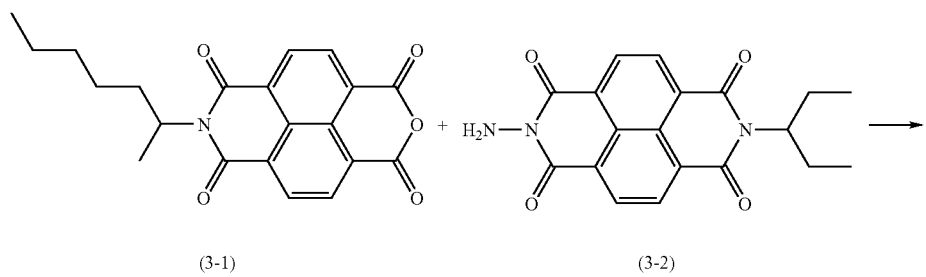

(3-1)    (3-2)

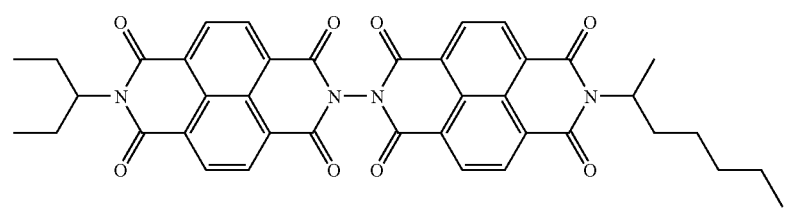

Example 4

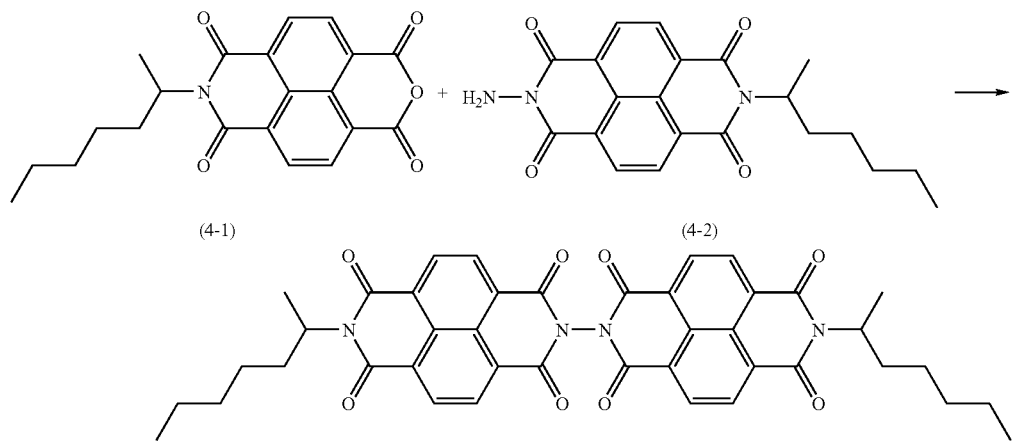

First Step: Synthesis of Naphthalene Monoimide Derivative (4-1)

A naphthalene monoimide derivative (4-1) was produced in the same manner as in the first step of Example 3.

Second Step: Synthesis of Naphthalene Monoimide Monohydrazone Derivative (4-2)

10.0 g of the naphthalene monoimide derivative (4-1) and 100 ml of dehydrated DMF were introduced and dissolved. Then, 1.52 g of hydrazine monohydrate was added dropwise thereto over 2 minutes and the resulting mixture was reacted at room temperature for 1.5 hours. Methanol was added dropwise thereto for precipitating a crystal. The crystal was filtered off, washed with methanol and dried to obtain a naphthalene monoimide monohydrazone derivative (4-2). Yield: 9.1 g.

Third Step 3.23 g of the naphthalene monoimide derivative (4-1), 2.8 g of the naphthalene monoimide monohydrazone derivative (4-2) and 120 ml of dehydrated DMF were introduced into a reactor. In the reactor, these were reacted under reflux for 51 hours. After cooling, the resulting mixture was concentrated under a reduced pressure and the residue was purified by column chromatography to obtain the desired product. Yield: 3.5 g.

When the melting point was measured, it was 227.4° C. As a result of mass spectrometry according to FD-MS, M/z was 726, from which it was identified as the desired product.

Example 5

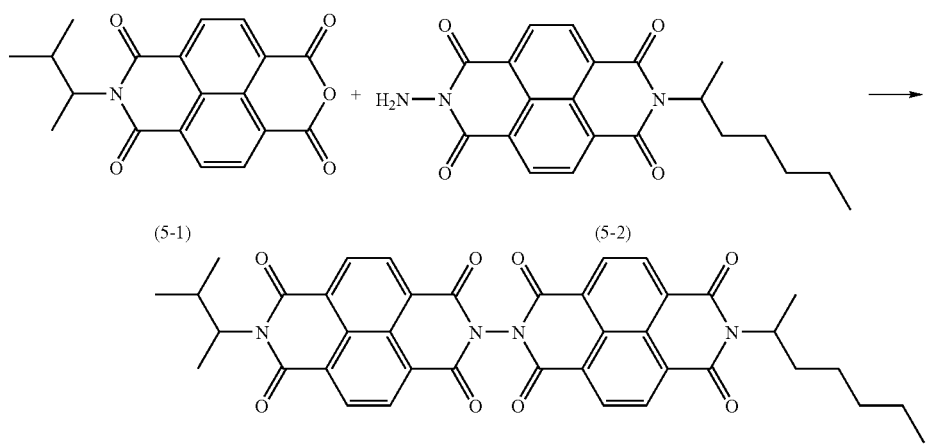

First Step: Synthesis of Naphthalene Monoimide Derivative (5-1)

10.0 g of a naphthalene-1.,4,5,8-tetracarboxylic dianhydride and 50 ml of dehydrated DMF were introduced into a reactor. The reactor was heated to reflux. 3.25 g of 1,2-dimethylpropylamine dissolved in 30 ml of dehydrated DMF was added dropwise into the reactor while stirring. After the dropwise addition was completed, the resultant was further heated to reflux for 6 hours. After cooling, the resulting mixture was concentrated under a reduced pressure. The residue was diluted with-toluene and the insoluble portion was filtered off. The filtrate was purified by silica gel column chromatography to obtain the desired product of a light orange monoimide derivative (5-1). Yield: 2.09 g.

Second Step: Synthesis of Naphthalene Monoimide Monohydrazone Derivative (5-2)

A naphthalene monoimide monohydrazone derivative (5-2) was produced in the same manner as in the second step of Example 4.

Third Step 1.00 g of the naphthalene monoimide derivative (5-1), 0.95 g of the naphthalene monoimide monohydrazone derivative (5-2) and 40 ml of dehydrated DMI were introduced into a reactor. In the reactor, these were reacted under reflux for 25 hours. After cooling, the resulting mixture was concentrated under a reduced pressure and the residue was purified by column chromatography to obtain the desired product. Yield: 0.89 g.

When the melting point was measured, it was 260.4° C. As a result of mass spectrometry according to FD-MS, M/z was 698, from which it was identified as the desired product.

Example 6

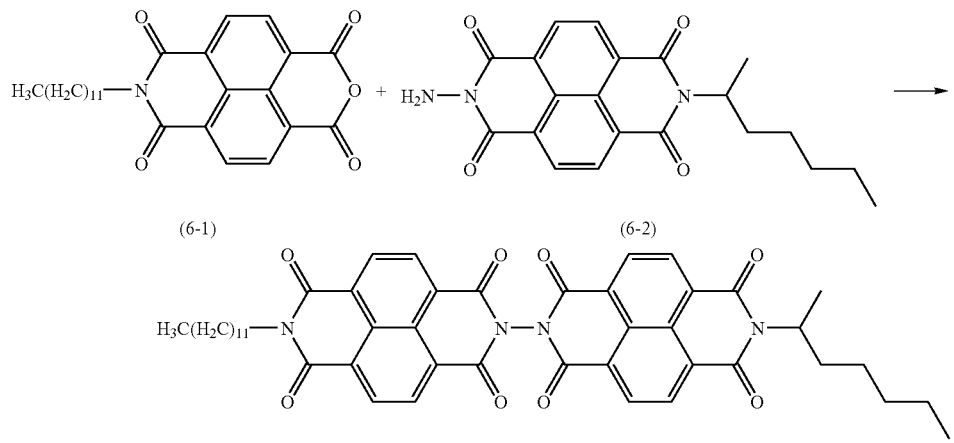

First Step: Synthesis of Naphthalene Monoimide Derivative (6-1)

27.68 g of a naphthalene-1,4,5,8-tetracarboxylic dianhydride and 250 ml of dehydrated DMF were introduced into a reactor. The reactor was heated to reflux. 21.03 g of dodecylamine dissolved in 110 ml of dehydrated DMF was added dropwise into the reactor over 50 minutes while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired product of a light yellow naphthalene monoimide derivative (6-1). Yield: 16.6 g.

Second Step: Synthesis of Naphthalene Monoimide Monohydrazone Derivative (6-2)

A naphthalene monoimide monohydrazone derivative (6-2) was produced in the same manner as in the second step of Example 4.

Third Step 2.51 g of the naphthalene monoimide monohydrazone derivative (6-2), 3.0 g of the naphthalene monoimide derivative (6-1) and 120 ml of dehydrated DMI were introduced into a reactor. In the reactor, these were reacted under reflux for 49 hours. After cooling, the precipitated crystal was filtered off, washed with DMF, washed with methanol, and dried. The crystal was dissolved in toluene and filtered through celite, and then concentrated, and crystallized from toluene/n-hexane to obtain the desired product. Yield: 2.55 g.

When the melting point was measured, it was 274.1° C. As a result of mass spectrometry according to FD-MS, M/z was 796, from which it was identified as the desired product.

Example 7

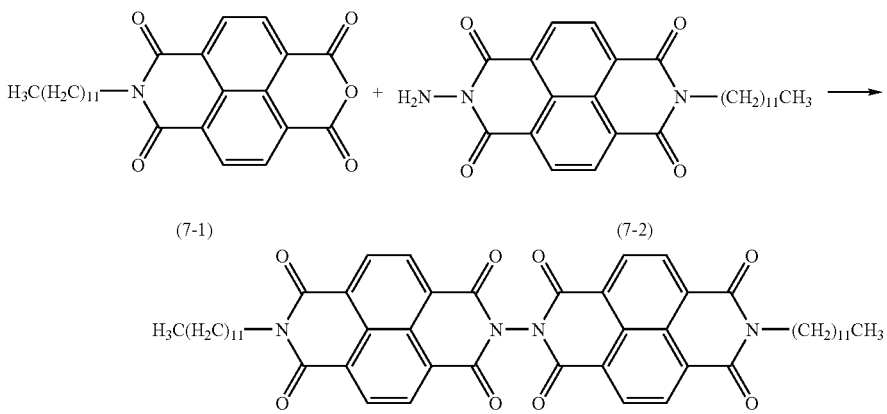

First Step: Synthesis of Naphthalene Monoimide Derivative (7-1)

A naphthalene monoimide derivative (7-1) was produced in the same manner as in the first step of Example 6.

Second Step: Synthesis of Naphthalene Monoimide Monohydrazone Derivative (7-2)

5.1 g of the naphthalene monoimide derivative (7-1) and 60 ml of dehydrated DMF were introduced, subjected to temperature elevation up to 70° C. and dissolved. Then, 0.65 g of hydrazine monohydrate was added dropwise thereto at 45° C. to 50° C. over 5 minutes, and the resulting mixture was heated up to 100° C. and reacted for 1.5 hours. After cooling, the precipitated crystal was filtered off, washed with methanol, and dried to obtain the desired product of a naphthalene monoimide monohydrazone derivative (7-2).

Yield: 4.76 g.

Third Step 2.83 g of the naphthalene monoimide derivative (7-1), 2.92 g of the naphthalene monoimide monohydrazone derivative (7-2) and 120 ml of dehydrated DMF were introduced into a reactor. In the reactor, these were reacted under reflux for 41 hours. After cooling, the precipitated crystal was filtered off, washed with DMF, washed with methanol, and dried. The crystal was dissolved in chloroform, purified by column chromatography, and crystallized from chloroform/n-hexane to obtain the desired product. Yield: 2.2 g.

When the melting point was measured, it was 297.7° C. As a result of mass spectrometry according to FD-MS, M/z was 866, from which it was identified as the desired product.

Example 8

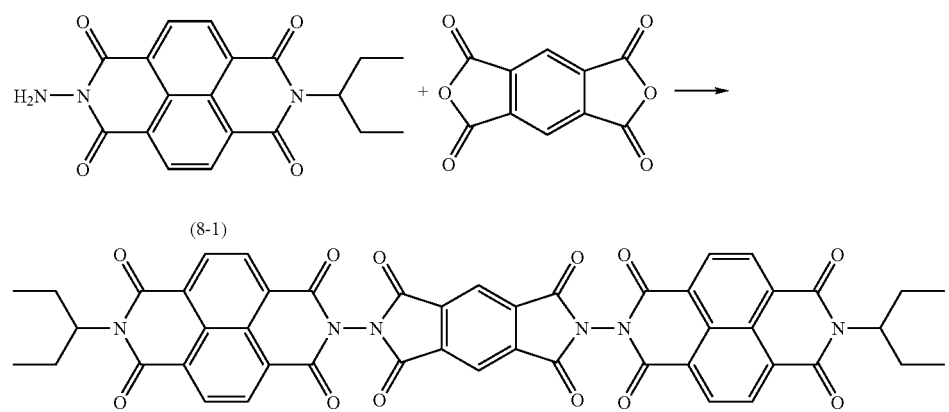

(8-1)

First Step: Synthesis of Naphthalene Monoimide Monohydrazone Derivative (8-1)

A naphthalene monoimide monohydrazone derivative (8-1) was produced in the same manner as in the second step of Example 2.

Second Step 3.0 g (8.54 mmole) of the naphthalene monoimide monohydrazone derivative (8-1), 0.93 g (0.5 molar ratio) of a pyromellitic anhydride and 100 ml of dehydrated DMF were introduced into a reactor. In the reactor, these were reacted under reflux for 31 hours. After cooling, methanol was introduced thereinto to precipitate a crystal. The crystal was filtered off and then recrystallized from chloroform to obtain the desired product. Yield: 2.07 g.

When the melting point was measured, it was not less than 400° C. As a result of mass spectrometry according to FD-MS, M/z was 884, from which it was identified as the desired product.

Example 9

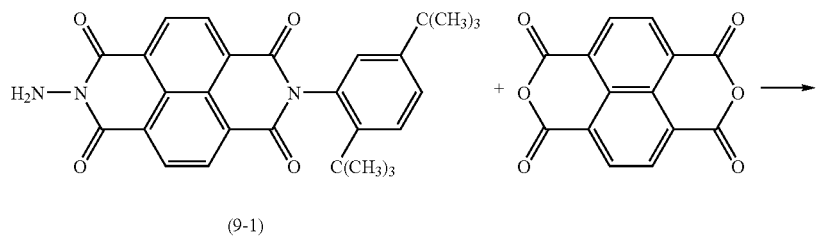

(9-1)

-continued

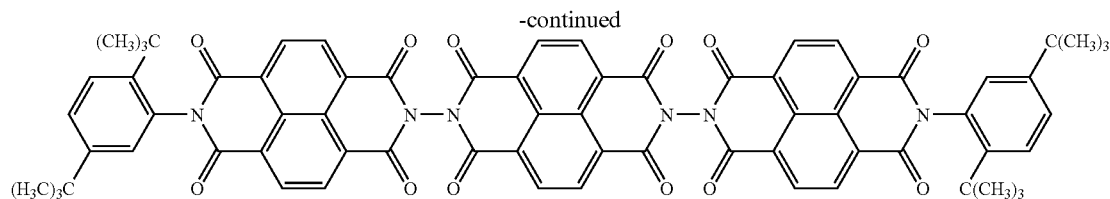

First Step: Synthesis of Naphthalene Monoimide Monohydrazone Derivative (9-1)

20.11 g of a naphthalene-1,4,5,8-tetracarboxylic dianhydride and 200 ml of dehydrated DMF were introduced into a reactor. The reactor was heated to reflux. 16.94 g of 2,4-di-t-butylaniline dissolved in 85 ml of dehydrated DMF was added dropwise into the reactor over 40 minutes while stirring. After the dropwise addition was completed, the resultant was further heated to reflux for 7 hours. After cooling, the resulting mixture was concentrated under a reduced pressure. The residue was diluted with 100 g of toluene and the insoluble portion was filtered off. This filtrate was purified by silica gel column chromatography. The recovered solution was concentrated until toluene was left in a small amount, and then a large quantity of hexane was added thereto and the resulting mixture was allowed to stand. Then, the crystal was filtered off to obtain the desired product of a light yellow monoimide derivative. Yield: 8.0 g.

7.0 g of the naphthalene monoimide derivative thus obtained was dissolved in 70 ml of dehydrated DMF. Next, 0.85 g of hydrazine monohydrate was added dropwise at room temperature over 10 minutes and the resulting mixture was reacted at room temperature for 3 hours. The precipitated crystal was filtered off, washed with methanol, and dried to obtain a naphthalene monoimide monohydrazone derivative (9-1). Yield: 4.58 g.

Second Step 4.5 g of the naphthalene monoimide monohydrazone derivative (9-1), 1.29 g of a naphthalene-1,4,5,8-tetracarboxylic dianhydride and 120 ml of DMI were introduced into a reactor. In the reactor, these were reacted at 180° C. to 190° C. for 20 hours. The reacted mass was cooled, and water was added dropwise thereto for precipitating a crystal. The crystal was washed with methanol and dried. The resulting crystal was dissolved in chloroform and the insoluble portion was filtered off. Then, the filtrate was purified by silica gel column chromatography. The resultant was concentrated until chloroform was left in a small amount, and crystallized from toluene/n-hexane. This operation was repeated once to obtain the desired product. Yield: 1.10 g.

When the melting point was measured, it was not less than 320° C. As a result of mass spectrometry according to FD-MS, M/z was 1,170, from which it was confirmed as the desired product.

Example 10

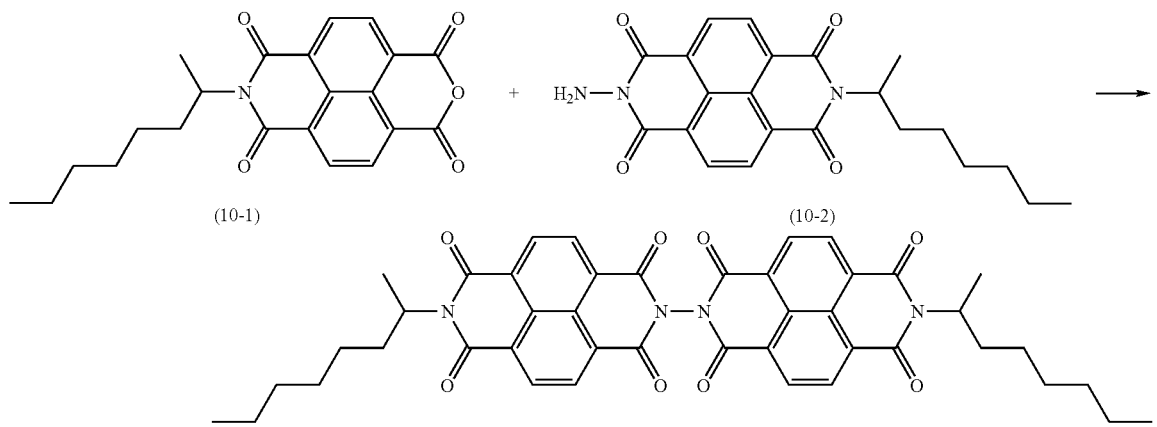

First Step: Synthesis of Naphthalene Monoimide Derivative (10-1)

39.55 g of a naphthalene-1,4,5,8-tetracarboxylic dianhydride and 500 ml of dehydrated DMF were introduced into a reactor. The reactor was heated to reflux. 20.0 g of 2-aminooctane dissolved in 80 ml of dehydrated DMF was added dropwise into the reactor over 45 minutes while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired product of a light yellow naphthalene monoimide derivative (10-1). Yield: 15.7 g.

Second Step: Synthesis of Naphthalene Monoimide Monohydrazone Derivative (10-2)

3.3 g of the naphthalene monoimide derivative (10-1) and 30 ml of dehydrated DMF were introduced, stirred and dissolved. Then, a mixed solution of 0.53 g of hydrazine monohydrate and 3 ml of dehydrated DMF was added dropwise thereto at 30° C. to 35° C. over 30 minutes, and then the resulting mixture was reacted under heating and refluxing for 1.5 hours. After cooling, DMF was concentrated and methanol was added to precipitate a crystal. The crystal was filtered, washed with methanol, and dried to obtain a naphthalene monoimide monohydrazone derivative (10-2).

Yield: 2.2 g.

Third Step 3.93 g of the naphthalene monoimide monohydrazone derivative (10-2), 3.8 g of the naphthalene monoimide derivative (10-1) and 120 ml of dehydrated DMF were introduced into a reactor. The reactor was reacted under reflux for 58 hours. After cooling, DMF was concentrated and the crystal was purified by silica gel column chromatography. The concentrated toluene was left in a small amount and n-hexane was added thereto, and the resultant was crystallized from toluene/n-hexane to obtain the desired product. Yield: 4.85 g.

When the melting point was measured, it was 217.7° C. As a result of mass spectrometry according to FD-MS, M/z was 754, from which it was identified as the desired product.

Example 11

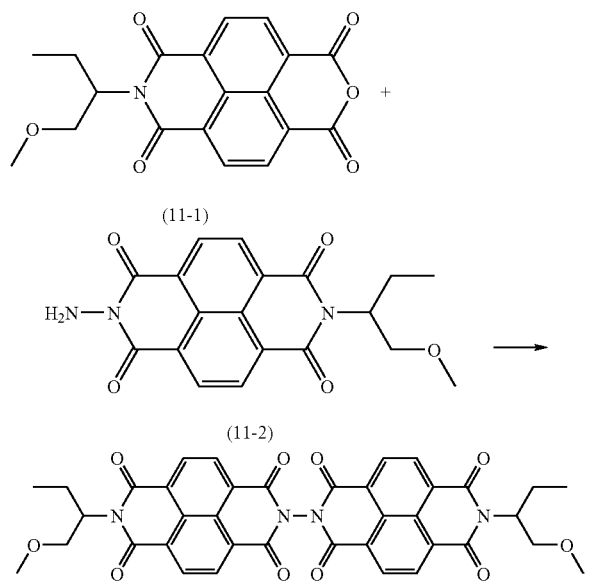

First Step: Synthesis of Naphthalene Monoimide Derivative (11-1)

26.82 g of a naphthalene-1,4,5,8-tetracarboxylic dianhydride and 250 ml of dehydrated DMF were introduced into a reactor. The reactor was heated to reflux. 10.52 g of 2-amino-1-methoxybutane dissolved in 50 ml of dehydrated DMF was added dropwise into the reactor over 45 minutes while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired product of a light yellow naphthalene monoimide derivative (11-1).

Yield: 12.9 g.

Second Step: Synthesis of Naphthalene Monoimide Monohydrazone Derivative (11-2)

7.0 g of the naphthalene monoimide derivative (11-1) obtained as above and 70 ml of dehydrated DMF were introduced, stirred and dissolved. Then, a mixed solution of 1.23 g of hydrazine monohydrate and 5 ml of dehydrated DMF was added dropwise thereto at 30° C. to 35° C. over 5 minutes, and then the resulting mixture was reacted under heating and refluxing for 1.5 hours. After cooling, methanol was added dropwise to precipitate a crystal. The crystal was filtered off, and then washed with methanol and dried to obtain a naphthalene monoimide monohydrazone derivative (11-2). Yield: 6.6 g.

Third Step 3.49 g of the naphthalene monoimide derivative (11-1), 3.3 g of the naphthalene monoimide monohydrazone derivative (11-2) and 120 ml of dehydrated DMF were introduced into a reactor. In the reactor, these were reacted under reflux for 53 hours. After cooling, DMF was concentrated under a reduced pressure and the crystal was purified by silica gel column chromatography. The concentrated toluene was left in a small amount and n-hexane was added thereto, and the resultant was crystallized from toluene/n-hexane to obtain the desired product. Yield: 3.7 g.

When the melting point was measured, it was 308.1° C. As a result of mass spectrometry according to FD-MS, M/z was 702, from which it was identified as the desired product.

Example 12

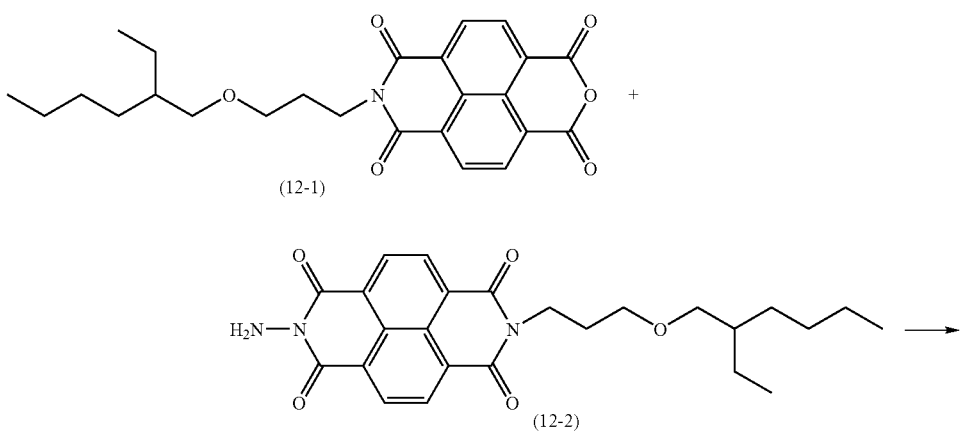

-continued

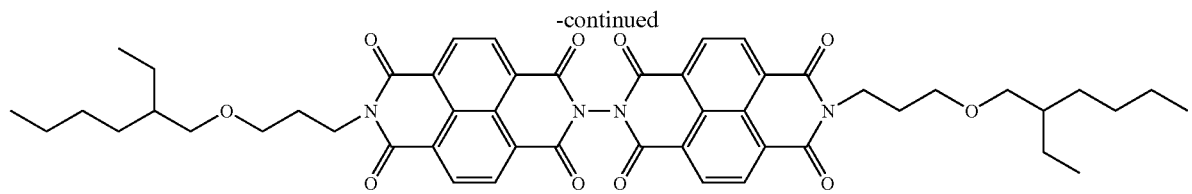

10

First Step: Synthesis of Naphthalene Monoimide Derivative (12-1)

26.82 g of a naphthalene-1,4,5,8-tetracarboxylic dianhydride and 250 ml of dehydrated DMF were introduced into a reactor. The reactor was heated to reflux. 19.5 g of 3-(2-ethylhexyloxy)propylamine dissolved in 50 ml of dehydrated DMF was added dropwise into the reactor over 45 minutes while stirring. After the dropwise addition was completed, the resultant was further heated to reflux for 6 hours. After cooling, the resulting mixture was concentrated under a reduced pressure. The residue was diluted with toluene and the insoluble portion was filtered off. The filtrate was purified by silica gel column chromatography to obtain the desired product of a light yellow naphthalene monoimide derivative (12-1).

Yield: 28.6 g.

Second Step: Synthesis of Naphthalene Monoimide Monohydrazone Derivative (12-2)

8.0 g of the naphthalene monoimide derivative (12-1) obtained as above and 70 ml of dehydrated DMF were introduced, stirred and dissolved. Then, a mixed solution of 0.99 g of hydrazine monohydrate and 5 ml of dehydrated DMF was added dropwise thereto at 30° C. to 35° C. over 5 minutes, and then the resulting mixture was reacted under heating and refluxing for 2 hours. After cooling, methanol was added dropwise to precipitate a crystal. The crystal was filtered off, and then washed with methanol and dried to obtain a naphthalene monoimide monohydrazone derivative (12-2). Yield: 7.2 g.

Third Step 3.5 g of the naphthalene monoimide derivative (12-1), 3.6 g of the naphthalene monoimide monohydrazone derivative (12-2) and 120 ml of dehydrated DMF were introduced into a reactor. In the reactor, these were reacted under reflux for 51 hours. After cooling, DMF was concentrated and the crystal was purified by silica gel column chromatography. The concentrated toluene was left in a small amount and n-hexane was added thereto, and the resultant was crystallized from toluene/n-hexane to obtain the desired product. Yield: 4.5 g.

When the melting point was measured, it was 234.2° C. As a result of mass spectrometry according to FD-MS, M/z was 870, from which it was identified as the desired product.

Example 13

Preparation and Evaluation of Single Layer Type Electrophotographic Photoconductor <Preparation of Single Layer Type Electrophotographic Photoconductor>

α-type $TiO_2$ phthalocyanine as a charge generating agent, the exemplified compound (A-8) as a hole transporting agent and the exemplified compound (4) as an electron transporting agent were selected. They were combined in the following ratio along with a polymeric binder and a solvent. The resulting mixture was mixed and dispersed with a ball mill for 50 hours. The dispersion was applied on a surface of a mirror surface-treated aluminum-made drum (conductive base material) having a diameter of 30 mm by the dip coating method and dried to prepare a single layer type electrophotographic photoconductor.

| (Components) | (Weight Parts) |
|---|---|
| Charge generating agent | 5 |
| Hole transporting agent | 50 |
| Electron transporting agent | 30 |
| Polymeric binder (polycarbonate) | 100 |
| Solvent (tetrahydrofuran) | 800 |

<Evaluation of Single Layer Type Electrophotographic Photoconductor>

In order to verify practicality of the resulting electrophotographic photoconductor, it was mounted on a commercial laser printer which employs a positive charging type electrophotographic photoconductor, under an environment of normal temperature and normal humidity (20° C. and 50% HR), 5,000 copies were continuously printed at lateral direction of A4 paper, and then printed samples were evaluated in terms of image quality and durability by visual observation. The results thereof were summarized in Table 1.

Example 14

Preparation and Evaluation of Organic Electrophotographic Photoconductor

A photoconductor was prepared in the same manner as in Example 13, except that the naphthalene tetracarboxylic acid derivative represented by the exemplified compound (16) was used instead of the electron transporting material (exemplified compound (4)) used in Example 13. The photoconductor was evaluated in the same manner as in Example 13. The results thereof were summarized in Table 1.

Comparative Example 1

Preparation and Evaluation of Organic Electrophotographic Photoconductor

A photoconductor was prepared in the same manner as in Example 13, except that a diphenoquinone compound (a product of Tokyo Kasei Kogyo Co., Ltd.) represented by the following formula (a) was used instead of the electron transporting material (exemplified compound (4)) used in Example 13. The photoconductor was evaluated in the same manner as in Example 13. The results thereof were summarized in Table 1.

TABLE 1

(a)

[Chemical structure: bis-quinone compound with (H₃C)₃C and C(CH₃)₃ substituents, and two =O groups]

| | Image quality of the first copy | Image quality of the 5,000th copy |
|---|---|---|
| Example 13 | Good | Good |
| Example 14 | Good | Good |
| Comparative Example 1 | Low density | Remarkably worsened density of image quality |

Example 15

Preparation and Evaluation of Dual-layered Type Electrophotographic Photoconductor <Preparation of Dual-Layered Type Electrophotographic Photoconductor>

100 weight parts of copper phthalocyanine as a charge generating agent, 100 weight parts of polyvinyl butyral as a polymeric binder and 2,000 weight parts of a solvent (tetrahydrofuran) were mixed and dispersed with a ball mill for 50 hours to prepare a coating solution for a charge generation layer. The coating solution was applied on a surface of an aluminum substrate that is a conductive base material by the dip coating method and dried up by hot air at 100° C. for 60 minutes to form a charge generation layer.

Subsequently, 100 weight parts of the exemplified compound (46) as an electron transporting agent, 100 weight parts of polycarbonate as a polymeric binder and 800 weight parts of a solvent (toluene) were mixed and dispersed with a ball mill for 50 hours to prepare a coating solution for an electron transport layer. The coating layer was applied on the charge generation layer by the dip coating method and dried up by hot air at 100° C. for 60 minutes to form a charge transport layer, thus preparing a dual-layered type electrophotographic photoconductor.

<Evaluation of Dual-Layered Type Electrophotographic Photoconductor>

In order to verify practicality of the resulting electrophotographic photoconductor, it was mounted on a commercial laser printer which employs a positive charging type electrophotographic photoconductor, under an environment of normal temperature and normal humidity (20° C. and 50% HR), 5,000 copies were continuously printed at lateral direction of A4 paper, and then printed samples were evaluated in terms of image quality and durability by visual observation. The results thereof were summarized in Table 2.

Comparative Example 2

<Evaluation of Organic Electrophotographic Photoconductor>

A photoconductor was prepared in the same manner as in Example 15, except that a compound (4H-thiopyran-1,1-dioxide derivative) represented by the following formula (b) was used instead of the electron transporting agent (exemplified compound (46)) used in Example 15. The photoconductor was evaluated in the same manner as in Example 15. The results thereof were summarized in Table 2.

TABLE 2

(b)

[Chemical structure: 4H-thiopyran-1,1-dioxide derivative with NC-C-CN dicyanomethylene group, phenyl and tolyl (CH₃-substituted phenyl) substituents, S with O₂]

| | Image quality of the first copy | Image quality of the 5,000th copy |
|---|---|---|
| Example 15 | Good | Good |
| Comparative Example 2 | Good | Remarkably worsened density of image quality from the 1,000th copy |

Example 16

Organic TFT Device

<Preparation and Evaluation of Device>

First, CrMo was formed into a CrMo film with a film thickness of 100 nm on a glass substrate by the sputtering method to prepare a gate electrode. Subsequently, on the gate electrode, oxide silicon ($SiO_2$) was formed into a $SiO_2$ film with a film thickness of 300 nm by the sputtering method to prepare an insulator layer.

Subsequently, according to the vacuum deposition method, the specific exemplified compound (14) was formed into a film with a film thickness of 300 nm to prepare an organic thin film layer. Furthermore, gold was formed into a film with a film thickness of 100 nm in the form of stripes on the organic thin film layer via a metal mask by the vacuum deposition method to form a source electrode and a drain electrode, thus obtaining an organic TFT.

A rectangular wave voltage with a frequency of 1-kHz and a maximum voltage of 20-V was applied to the gate electrode of the thus-prepared organic TFT and a 20-V direct-current voltage was applied between the source and the drain respectively. In this state, the time for the first response (the time from 10% change to 90% change of the whole change) was measured when the current between the source and drain electrodes was on. As a result, it was less than 1 μs.

Further, a gate voltage of 50 V was applied to the prepared organic TFT. As a result, an on-off ratio of the current between the source and drain electrodes was $4 \times 10^5$.

Example 17

Electron Injecting and Transporting Layer of Organic Electroluminescent Device

<Preparation of Device>

A glass substrate (a product of Hoya Corp.) patterned with ITO (1000 Å) to be an anode was used as a substrate. This substrate was subjected to ultrasonic cleaning successively using acetone, deionized water, a substrate cleaner (Semicoclean, grade EL, a product of Furuuchi Chemical Co., Ltd.), deionized water and isopropyl alcohol (IPA), and then from boiling IPA, the substrate was taken out and dried. In order to eliminate organic contaminant on the ITO surface, the substrate was further subjected to a UV ozone treatment.

The thus dried substrate was mounted on a temperature-controllable substrate holder disposed in a vacuum vapor deposition apparatus. Then, a mask for an organic compound layer was placed under vacuum, and a hole transporting layer (TPD) 600 Å, a light-emitting layer (aluminum quinolinol complex, Alq3) 400 Å and an electron injecting and transporting layer (exemplified compound (8)) 200 Å were successively stacked for forming a film by heating on a carbon crucible, as the organic compound layer.

Then, the mask was changed to a negative electrode under vacuum, and magnesium and silver were vapor codeposited such that the molar ratio became Mg/Ag=10/1 to form a film as a cathode. On the resultant electrode, silver was solely vapor deposited. Their respective film thicknesses were 2,000 Å and 1,000 Å. Each film constituting the device was formed under a vacuum of not more than $5\times10^{-7}$ Torr.

<Evaluation of Characteristics>

With respect to the organic electroluminescent device prepared according to the above method, inside of a chamber completely substituted with nitrogen, a relationship between the applied voltage and light-emitting luminance, and a relationship between the injected current density and light-emitting luminance were measured.

Under the conditions of a drive voltage of 10 V and a current density of 100 mA/cm$^2$, a luminance of 700 cd/m$^2$ was recognized.

Comparative Example 3

As a comparative example, a device of a multi-layered structure in which Alq3 was formed into a film with 200 Å as an electron injecting and transporting layer as in Example 17 was prepared.

Inside of a chamber completely substituted with nitrogen, a relationship between the applied voltage and light-emitting luminance, and a relationship between the injected current density and light-emitting luminance were measured. As a result, under the condition of a current density of 100 mA/cm$^2$, a luminance of 550 cd/m$^2$ was recognized.

Example 18

Organic Solar Cell

<Preparation of Device>

A glass substrate (a product of Hoya Corp.) containing patterned with ITO (1000 Å) to be a transparent electrode was used as a substrate. This substrate was subjected to ultrasonic cleaning successively using acetone, deionized water, a substrate cleaner (Semicoclean, grade EL, a product of Furuuchi Chemical Co., Ltd.), deionized water and isopropyl alcohol (IPA), and then from boiling IPA, the substrate was taken out and dried. In order to eliminate organic contaminant on the ITO surface, the substrate was further subjected to a UV ozone treatment.

The thus dried substrate was mounted on a temperature-controllable substrate holder disposed in a vacuum vapor deposition apparatus. Then, by heating on a carbon crucible under vacuum, a copper phthalocyanine pigment of 60 nm as an organic p-type semiconductor layer, a codeposition layer of a copper phthalocyanine pigment and the exemplified compound (66) of 30 nm as an active layer and C60 of 20 nm as an organic n-type semiconductor layer were successively stacked for forming a film.

Then, magnesium and silver were vapor codeposited such that the molar ratio became Mg/Ag=10/1 to form an electrode. On the resultant electrode, silver was solely vapor deposited to obtain an organic solar cell with an effective area of 0.1 cm$^2$. Their respective film thicknesses were 100 nm and 100 nm. Each film constituting the device was formed under a vacuum of not more than $5\times10^{-7}$ Torr.

<Evaluation of Characteristics>

With respect to the organic solar cell prepared according to the above method, light irradiated from a xenon lamp of 500 W (a product of Ushio Inc.) was passed through a spectrographic filter, and a device for obtaining an simulated sunlight was used. The intensity of the simulated sunlight was 100 mW/cm$^2$.

As for the organic solar cell, each electrode was connected to an alligator clip and the generated electricity was measured using a current-voltage tester. The tester was composed of a current meter, a function generator and a potentiostat.

As a result, solar cell characteristics showing a conversion efficiency of 1.4% were obtained.

The novel compound obtained by the present invention is superior in the capability of transporting electrons. When such a compound is used for an organic electronic device, an organic electronic device with high sensitivity and high durability which is excellent in electrical properties, repetition stability and thin-film stability as well is obtained.

The novel compound of the present invention is useful for various organic electronic devices including an electrophotographic photoconductor, an organic transistor, an organic solar cell and an organic electroluminescent device, and is capable of providing such organic electronic devices.

The invention claimed is:

1. A compound represented by the general formula (3),

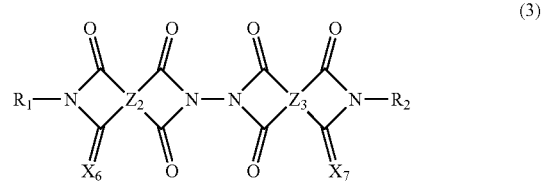

(3)

wherein, in the formula, $Z_2$ and $Z_3$ each independently represent a tetravalent organic group constituting an unsubstituted naphthalene tetracarboxylic acid or dianhydride or a substituted naphthalene tetracarboxylic acid or dianhydride wherein the substituent is selected from the group consisting of alkyl group, alkoxy group, alkylthio group, aryl group, aryloxy group, arylthio group, halogenated alkyl group, halogen atom, carboxyl group, esterified carboxyl group, and cyano group; $X_6$ and $X_7$ each independently represent an oxygen atom, a sulfur atom or NR$_0$ (wherein R$_0$ represents a hydrogen atom, a substituted or unsubstituted aryl group, a substituted or unsubstituted alkyl group, a substituted or unsubstituted cycloalkyl group, a substituted or unsubstituted aralkyl group); when $X_6$ is a nitrogen atom, $X_6$ may be bonded to R$_1$ for forming a ring structure; when $X_7$ is a nitrogen atom, $X_7$ may be bonded to R$_2$ for forming a ring structure; and R$_1$ and R$_2$ each independently represent a hydrogen atom, a substituted or unsubstituted aryl group a substituted or unsubstituted alkyl group, a substituted or unsubstituted cycloalkyl group, a substituted or unsubstituted aralkyl group or a group selected from the group consisting of the following general formula (4),

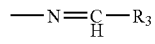 (4)

wherein, in the formula, $R_3$ represents a substituted or unsubstituted aryl group, a substituted or unsubstituted alkyl group, or a substituted or unsubstituted cycloalkyl group.

2. An electrophotographic photoconductor containing at least one compound as described in claim 1.

3. An organic transistor containing at least one compound as described in claim 1.

4. An organic solar cell containing at least one compound as described in claim 1.

5. An organic electroluminescent device containing at least one compound as described in claim 1.

* * * * *